United States Patent
Hoffman et al.

(10) Patent No.: US 11,358,957 B2
(45) Date of Patent: Jun. 14, 2022

(54) MICROBIOCIDAL OXADIAZOLE DERIVATIVES

(71) Applicant: SYNGENTA PARTICIPATIONS AG, Basel (CH)

(72) Inventors: Thomas James Hoffman, Stein (CH); Daniel Stierli, Stein (CH); Thomas Pitterna, Stein (CH); Ramya Rajan, Goa (IN)

(73) Assignee: SYNGENTA PARTICIPATIONS AG, Basel (CH)

( * ) Notice: Subject to any disclaimer, the term of this patent is extended or adjusted under 35 U.S.C. 154(b) by 292 days.

(21) Appl. No.: 16/489,805

(22) PCT Filed: Mar. 1, 2018

(86) PCT No.: PCT/EP2018/055042
§ 371 (c)(1),
(2) Date: Aug. 29, 2019

(87) PCT Pub. No.: WO2018/158365
PCT Pub. Date: Sep. 7, 2018

(65) Prior Publication Data
US 2020/0277287 A1    Sep. 3, 2020

(30) Foreign Application Priority Data

Mar. 3, 2017 (EP) .................................. 17159202
Mar. 10, 2017 (EP) .................................. 17160411
Dec. 1, 2017 (IN) ........................... 201711043196

(51) Int. Cl.
| | |
|---|---|
| *C07D 413/14* | (2006.01) |
| *C07D 417/14* | (2006.01) |
| *C07D 471/04* | (2006.01) |
| *A01N 43/82* | (2006.01) |
| *A01N 43/84* | (2006.01) |
| *A01N 43/90* | (2006.01) |

(52) U.S. Cl.
CPC ......... *C07D 413/14* (2013.01); *A01N 43/82* (2013.01); *A01N 43/84* (2013.01); *A01N 43/90* (2013.01); *C07D 417/14* (2013.01); *C07D 471/04* (2013.01)

(58) Field of Classification Search
None
See application file for complete search history.

(56) References Cited

FOREIGN PATENT DOCUMENTS

| | | |
|---|---|---|
| BE | 808734 A | 4/1974 |
| EP | 0276432 A2 | 8/1988 |
| GB | 1429725 A | 3/1976 |
| WO | 2009029632 A1 | 3/2009 |
| WO | 2015185485 A1 | 12/2015 |
| WO | 2017085100 A1 | 5/2017 |

OTHER PUBLICATIONS

European Search Report for European Patent Application No. 17159202.5 dated Jun. 6, 2017.
International Search Report for International Patent Application No. PCT/EP2018/055042 dated May 2, 2018.

*Primary Examiner* — Alton N Pryor
(74) *Attorney, Agent, or Firm* — BakerHostetler; Toni-Junell Herbert

(57) ABSTRACT

Compounds of the formula (I) wherein the substituents are as defined in claim 1, useful as pesticides, especially as fungicides.

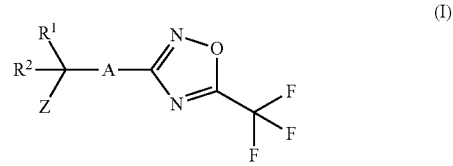

14 Claims, No Drawings

MICROBIOCIDAL OXADIAZOLE DERIVATIVES

CROSS-REFERENCE TO RELATED APPLICATIONS

This application is a 371 National Stage application of International Application No. PCT/EP20180/55042, filed Mar. 1, 2018, which claims priority to EP 17159202.5, filed Mar. 3, 2017, EP 17160411.9, filed Mar. 10, 2017, and IN 201711043196, filed Dec. 1, 2017, the entire contents of which applications are hereby incorporated by reference.

The present invention relates to microbiocidal oxadiazole derivatives, e.g., as active ingredients, which have microbiocidal activity, in particular, fungicidal activity. The invention also relates to agrochemical compositions which comprise at least one of the oxadiazole derivatives, to processes of preparation of these compounds and to uses of the oxadiazole derivatives or compositions in agriculture or horticulture for controlling or preventing infestation of plants, harvested food crops, seeds or non-living materials by phytopathogenic microorganisms, preferably fungi.

WO 2015/185485 describes the use of substituted oxadiazoles for combating phytopathogenic fungi.

According to the present invention, there is provided a compound of Formula (I):

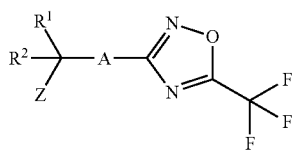

(I)

wherein
A is selected from A-1, A-2 or A-3;

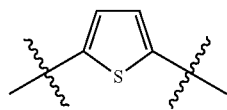

(A-1)

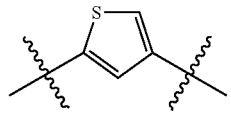

(A-2)

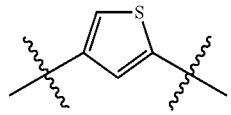

(A-3)

$R^1$ and $R^2$ independently represent hydrogen, methyl, ethyl, fluoro, cyano, difluoromethyl or trifluoromethyl; and
Z is selected from $Z^1$, $Z^2$ or $Z^3$; wherein
$Z^1$ represents a 4- to 6-membered non-aromatic heterocyclyl ring containing 1 ring nitrogen, wherein the heterocyclyl optionally comprises 1 or 2 additional ring members independently selected from N, O, S, C(O) and S(O)$_2$ with the proviso that the heterocyclyl ring cannot contain 2 contiguous atoms selected from O and S, or the heterocycyl optionally comprises 1 additional ring member $NR^3$, wherein the heterocycyl is optionally substituted by 1 or 2 substituents, which may be the same or different, selected from $R^4$, and wherein further the heterocyclyl is bound to the rest of the molecule through a ring nitrogen;

$R^3$ represents hydrogen, hydroxy, amino, formyl, $C_{1-3}$alkyl, $C_{1-3}$alkoxy, $C_{1-3}$alkylcarbonyl, $C_{1-3}$alkoxycarbonyl, N—$C_{1-3}$alkylaminocarbonyl, N,N-di$C_{1-3}$alkylaminocarbonyl, N—$C_{1-3}$alkoxyaminocarbonyl, N—$C_{1-3}$alkyl-N—$C_{1-3}$alkoxy-aminocarbonyl, $C_{1-2}$alkylsulfonyl, N—$C_{1-2}$alkylaminosulfonyl, N,N-di$C_{1-2}$alkylaminosulfonyl, $C_{1-2}$alkyldicarbonyl, $C_{1-2}$alkoxydicarbonyl, N—$C_{1-2}$alkylaminodicarbonyl or N,N-di$C_{1-2}$ alkylaminodicarbonyl;

$R^4$ represents cyano, halogen, hydroxy, amino, methyl, ethyl, difluoromethyl, trifluoromethyl, methoxy, N-methylamino or N,N-dimethylamino;

$Z^2$ represents a 5- or 6-membered heteroaryl ring containing 1 ring nitrogen, wherein the heteroaryl optionally comprises 1, 2 or 3 additional ring members independently selected from O, S, or N, and wherein the heteroaryl is optionally substituted by: 1 or 2 substituents selected from $R^5$, 1 substituent selected from $R^6$, or 1 substituent selected from $R^5$ and 1 substituent selected from $R^6$, and wherein further the heteroaryl is bound to the rest of the molecule through a ring nitrogen;

$R^5$ represents hydroxyl, amino, cyano, halogen, formyl, nitro, $C_{1-4}$alkyl, $C_{1-4}$alkoxy, $C_{3-4}$alkenyl, $C_{3-4}$alkynyl, $C_{3-4}$alkenyloxy, $C_{3-4}$alkynyloxy, cyano$C_{1-12}$alkyl, $C_{1-2}$haloalkyl, hydroxy$C_{1-2}$alkyl, $C_{1-2}$alkoxy$C_{1-2}$ alkyl, $C_{1-2}$alkoxy$C_{1-2}$alkoxy$C_{1-2}$alkyl, N,N-dimethylamino, $C_{1-3}$alkoxycarbonyl$C_{1-2}$alkyl, $C_{1-3}$alkycarbonyloxy$C_{1-2}$alkyl, N—$C_{1-3}$alkylaminocarbonyl$C_{1-2}$alkyl, N,N-di$C_{1-3}$alkylaminocarbonyl$C_{1-2}$alkyl, $C_{1-2}$alkylsufonyl, $C_{1-3}$alkylcarbonyl, $C_{1-3}$alkyldicarbonyl, $C_{1-3}$alkoxydicarbonyl, N—$C_{1-3}$alkylaminodicarbonyl, or N,N-di$C_{1-3}$alkylaminodicarbonyl; or $R^5$ represents —C(O)N($R^a$)($R^b$) wherein:
$R^a$ represents hydrogen, $C_{1-6}$alkyl, $C_{3-4}$alkenyl, $C_{3-4}$alkynyl, $C_{1-3}$haloalkyl, $C_{3-4}$haloalkenyl, $C_{1-4}$alkoxy, $C_{1-2}$alkoxy$C_{1-3}$alkyl, $C_{2-3}$haloalkoxy, $C_{3-4}$alkenyloxy, $C_{3-4}$alkynyloxy, N—$C_{1-3}$alkylamino, or N,N-di$C_{1-2}$alkylamino; or $R^a$ represents $C_{3-5}$cycloakyl, $C_{3-5}$cycloalkyl$C_{1-2}$alkyl, phenyl, phenyl$C_{1-2}$alkyl, heterocyclyl, wherein the heterocyclyl moiety is a 4- to 6-membered non-aromatic ring which comprises 1 or 2 heteroatoms independently selected from N, O or S, with the proviso that the heterocyclyl cannot contain 2 contiguous atoms selected from O and S, heteroaryl or heteroaryl$C_{1-2}$alkyl, wherein the heteroaryl moiety is a 5- or 6-membered aromatic ring which comprises 1, 2, 3, or 4 heteroatoms individually selected from N, O and S; wherein the cycloalkyl, phenyl, heterocyclyl or heteroaryl is optionally substituted by 1 or 2 substituents, which may be the same or different, selected from hydroxyl, amino, formyl, acyl, cyano, halogen, methyl, trifluoromethyl, methoxy, or N,N-dimethylamino, and wherein when $R^a$ represents cycloalkyl or heterocyclyl, these cycles optionally contain 1 group selected from C(O) or S(O)$_2$; and $R^b$ represents hydrogen, methyl, ethyl, propyl, prop-2-enyl, prop-2-ynyl, cyclopropyl, or cyclopropylmethyl; or $R^a$ and $R^b$, together with the nitrogen atom they share, form an azetidinyl, pyrrolidinyl, isooxazolidinyl, morpholino, piperazin-4-yl, or piperidinyl ring optionally substituted by 1 or 2 groups selected from halogen, methyl, ethyl or methoxy; or $R^5$ represents —C(O)O—$R^c$, wherein:
$R^c$ represents hydrogen, $C_{1-6}$alkyl, $C_{3-5}$alkenyl, $C_{3-5}$alkynyl, $C_{1-3}$haloalkyl, $C_{3-4}$haloalkenyl, N,N-di$C_{1-3}$alkylaminoC$_{1-3}$alkyl, C$_{3-6}$cycloalkyl, C$_{3-4}$cycloalkylC$_{1-2}$alkyl, phenyl, heterocyclyl, wherein the heterocyclyl moiety is a 4- to 6-membered non-aromatic ring which comprises 1 or 2 heteroatoms independently selected from O, S and N, with the proviso that the heterocyclyl cannot contain 2 contiguous atoms selected from O and S, heteroaryl, wherein the heteroaryl moiety is a 5- or 6-membered aromatic ring which comprises 1, 2 or 3 heteroatoms individually selected from N, O and S; and wherein the cycloalkyl, phenyl, heterocyclyl or heteroaryl is optionally substituted by 1 or 2 substituents, which may be the same or different, selected from hydroxyl, amino, formyl, methylcarbonyl, cyano, halogen, methyl, trifluoromethyl, methoxy, or N,N-dimethylamino, and wherein when R represents cycloalkyl or heterocyclyl, these cycles optionally contain 1 group selected from C(O) or S(O)$_2$; or R$^5$ represents —N(R$^d$)(R$^e$) or —C$_{1-2}$alkyl-N(R$^d$)(R$^e$), wherein R$^d$ represents C$_{1-3}$alkyl, C$_{3-4}$alkenyl, C$_{3-4}$alkynyl, methylcarbonyl, methoxycarbonyl, N-methylaminocarbonyl, N,N-dimethylaminocarbonyl, N-methoxyaminocarbonyl, N-methyl-N-methoxyaminocarbonyl, methylsulfonyl, N-methylaminosulfonyl, N,N-dimethylaminosulfonyl, methyldicarbonyl, N-methylaminodicarbonyl, or N,N-dimethylaminodicarbonyl; and R$^e$ represents hydrogen, methyl, ethyl, or propyl; or R$^d$ and R$^e$, together with the nitrogen atom they share, form an azetidinyl, pyrrolidinyl, isooxazoldinyl, morpholino, piperazin-4-yl, or piperidinyl ring optionally substituted by 1 or 2 groups selected from halogen, methyl, ethyl or methoxy; or R$^5$ represents —CH=N(R$^f$), wherein R$^f$ represents C$_{1-4}$alkyl, C$_{1-4}$alkoxy, C$_{2-4}$alkenoxy, or C$_{2-4}$alkynoxy;

R$^6$ represents C$_{3-6}$cycloakyl, phenyl, heteroaryl, wherein the heteroaryl moiety is a 5- or 6-membered aromatic ring which comprises 1, 2, 3 or 4 heteroatoms individually selected from N, O and S, heterocyclyl, wherein the heterocycyl moiety is a 4- to 6-membered non-aromatic ring which comprises 1 or 2 heteroatoms individually selected from N, O and S, and wherein the cycloalkyl, phenyl, heteroaryl and heterocyclyl is optionally substituted by 1 or 2 substituents, which may be the same or different, selected from hydroxyl, amino, formyl, acyl, cyano, halogen, methyl, trifluoromethyl, methoxy, N,N-dimethylamino, and wherein when R$^6$ represents cycloalkyl or heterocyclyl, these cycles optionally contain 1 group selected from C(O) or S(O)$_2$; and Z$^3$ represents a heterobicyclyl which is a 7- to 9-membered saturated, partially saturated, or aromatic fused ring or saturated spirocyclic ring system containing 1 nitrogen, wherein the heterobicyclyl optionally comprises 1 or 2 additional ring members independently selected from N, O, S, C(O) and S(O)$_2$ with the proviso that the heterobicyclyl cannot contain 2 contiguous atoms selected from O and S, wherein the heterobicyclyl is optionally substituted by 1 substituent selected from R$^7$, and wherein further the heterobicyclyl is bound to the rest of the molecule through a ring nitrogen; and R$^7$ is cyano, fluoro, chloro, amino, hydroxy, methyl, difluoromethyl, trifluoromethyl, methoxy, N,N-dimethylamino, formyl, methylcarbonyl, methoxycarbonyl, N-methylaminocarbonyl, or N,N-dimethylaminocarbonyl;

or a salt or N-oxide thereof.

Surprisingly, it has been found that the novel-compounds of Formula (I) have, for practical purposes, a very advantageous level of biological activity for protecting plants against diseases that are caused by fungi.

According to a second aspect of the invention, there is provided an agrochemical composition comprising a fungicidally effective amount of a compound of Formula (I). Such an agricultural composition may further comprise at least one additional active ingredient and/or an agrochemically-acceptable diluent or carrier.

According to a third aspect of the invention, there is provided a method of controlling or preventing infestation of useful plants by phytopathogenic microorganisms, wherein a fungicidally effective amount of a compound of Formula (I), or a composition comprising this compound as active ingredient, is applied to the plants, to parts thereof or the locus thereof.

According to a fourth aspect of the invention, there is provided the use of a compound of Formula (I) as a fungicide. According to this particular aspect of the invention, the use may exclude methods for the treatment of the human or animal body by surgery or therapy.

As used herein, the term "halogen" or "halo" refers to fluorine (fluoro), chlorine (chloro), bromine (bromo) or iodine (iodo), preferably fluorine, chlorine or bromine.

As used herein, cyano means a —CN group.

As used herein, the term "hydroxyl" or "hydroxy" means an —OH group.

As used herein, amino means an —NH$_2$ group.

As used herein, acyl means a —C(O)CH$_3$ group.

As used herein, formyl means a —C(O)H group.

As used herein, the term "C$_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. C$_{1-4}$alkyl, C$_{1-3}$alkyl and C$_{1-2}$alkyl are to be construed accordingly. Examples of C$_{1-6}$alkyl include, but are not limited to, methyl, ethyl, n-propyl, 1-methylethyl (isopropyl), n-butyl, and 1-dimethylethyl (t-butyl). A "C$_1$-C$_2$alkylene" group refers to the corresponding definition of C$_{1-2}$alkyl, except that such radical is attached to the rest of the molecule by two single bonds. Examples of C$_{1-2}$alkylene, are —CH$_2$— and —CH$_2$CH—.

As used herein, the term "C$_{1-4}$alkoxy" refers to a radical of the formula —OR$_x$ where R$_x$ is a C$_{1-4}$ alkyl radical as generally defined above. The terms C$_{1-3}$alkoxy and C$_{1-2}$alkoxy are to be construed accordingly. Examples of C$_{1-4}$alkoxy include, but are not limited to, methoxy, ethoxy, propoxy, isopropoxy, and t-butoxy.

As used herein, the term "C$_{1-3}$haloalkyl" refers to a C$_{1-3}$alkyl radical as generally defined above substituted by one or more of the same or different halogen atoms. Examples of C$_{1-3}$haloalkyl include, but are not limited to fluoromethyl, fluoroethyl, difluoromethyl, trifluoromethyl, 2,2,2-trifluoroethyl, and 3,3,3-trifluoropropyl.

As used herein, the term "C$_{2-6}$alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. C$_{3-6}$alkenyl, C$_{3-5}$alkenyl, C$_{2-4}$alkenyl and C$_{2-3}$alkenyl are to be construed accordingly. Examples of C$_{2-6}$alkenyl include, but are not limited to, prop-1-enyl, allyl (prop-2-enyl), and but-1-enyl.

As used herein, the term "C$_{3-6}$haloalkenyl" refers to a C$_{3-6}$alkenyl radical as generally defined above substituted by one or more of the same or different halogen atoms. C$_{3-4}$haloalkenyl is to be construed accordingly.

As used herein, the term "$C_{2-4}$alkenoxy" refers to a radical of the formula —$OR_x$ where $R_x$ is a $C_{2-4}$alkenyl radical as generally defined above.

As used herein, the term "$C_{2-6}$alkynyl" refers to a straight or branched hydrocarbon chain radical group consisting solely of carbon and hydrogen atoms, containing at least one triple bond, having from two to six carbon atoms, and which is attached to the rest of the molecule by a single bond. $C_{3-5}$alkynyl and $C_{2-4}$alkynyl are to be construed accordingly. Examples of $C_{2-6}$alkynyl include, but are not limited to, prop-1-ynyl, propargyl (prop-2-ynyl).

As used herein, the term "$C_{2-4}$alkynoxy" refers to a radical of the formula —$OR_x$ where $R_x$ is a $C_{2-4}$alkynyl radical as generally defined above.

As used herein, the term "$C_{1-4}$alkoxy$C_{1-4}$alkyl" refers to radical of the formula $R_y$—O—$R_x$— where $R_y$ is a $C_{1-4}$alkyl radical as generally defined above, and $R_x$ is a $C_{1-4}$alkylene radical as generally defined above.

As used herein, the term "hydroxy$C_{1-4}$alkyl" refers to a $C_{1-4}$alkyl radical as generally defined above substituted by one or more hydroxy groups. The term "hydroxy$C_{1-2}$alkyl" should be construed accordingly.

As used herein, the term "cyano$C_{1-2}$alkyl" refers to refers to a $C_{1-2}$alkyl radical as generally defined above substituted by one or more cyano groups.

As used herein, the term "$C_{1-4}$alkylcarbonyl" refers to a radical of the formula —$C(O)R_x$ where $R_x$ is a $C_{1-4}$alkyl radical as generally defined above.

As used herein, the term "$C_{1-3}$alkyldicarbonyl" refers to a radical of the formula —$[C(O)]_2R_x$ where $R_x$ is a $C_{1-3}$alkyl radical as generally defined above.

As used herein, the term "$C_{1-3}$alkylcarbonyloxy$C_{1-2}$alkyl" refers to a radical of the formula $R_yC(O)OR_x$— where $R_y$ is a $C_{1-3}$alkyl radical as generally defined above, and $R_x$ is a $C_{1-2}$alkylene radical as generally defined above.

As used herein, the term "$C_{1-2}$alkoxy$C_{1-2}$alkoxy$C_{1-2}$alkyl" refers to a radical of the formula $R_xOR_yOR_z$—, where $R_y$ and $R_z$ are $C_{1-2}$alkylene radicals as generally defined above, and $R_x$ is a $C_{1-2}$alkyl radical as generally defined above.

As used herein, the term "$C_{1-3}$alkoxyaminocarbonyl" refers to a radical of the formula $R_xONHC(O)$—, where $R_x$ is a $C_{1-3}$alkyl radical as generally defined above.

As used herein, the term "N—$C_{1-3}$alkyl-N—$C_{1-3}$alkoxyaminocarbonyl" refers to a radical of the formula $(R_x)(R_xO)NHC(O)$— where each $R_x$ is a $C_{1-3}$alkyl radical as generally defined above.

As used herein, the term "$C_{1-3}$alkoxycarbonyl" refers to a radical of the formula $R_xOC(O)$—, where $R_x$ is a $C_{1-3}$alkyl radical as generally defined above.

As used herein, the term "$C_{1-3}$alkoxycarbonyl$C_{1-2}$alkyl" refers to a radical of the formula $R_xOC(O)R_y$—, where $R_x$ is a $C_{1-3}$alkyl radical as generally defined above, and $R_y$ is a $C_{1-2}$alkylene radical as generally defined above.

As used herein, the term "$C_{1-3}$alkoxydicarbonyl" refers to a radical of the formula $R_xO[C(O)]_2$—, where $R_x$ is a $C_{1-3}$alkyl radical as generally defined above. The term $C_{1-2}$alkoxydicarbonyl should be construed accordingly.

As used herein, the term "$C_{1-2}$alkylsulfonyl" refers to a radical of the formula $R_xS(O)_2$—, where $R_x$ is a $C_{1-2}$alkyl radical as generally defined above.

As used herein, the term "N—$C_{1-3}$alkylamino" refers to a radical of the formula $R_xNH$— where $R_x$ is a $C_{1-3}$alkyl radical as generally defined above.

As used herein, the term "N,N-di$C_{1-2}$alkylamino" refers to a radical of the formula $R_x(R_x)N$— where $R_x$ is a $C_{1-2}$alkyl radical as generally defined above.

As used herein, the term "N—$C_{1-2}$alkylaminosulfonyl" refers to a radical of the formula $R_xNH\,S(O)_2$— where $R_x$ is a $C_{1-2}$alkyl radical as generally defined above.

As used herein, the term "N,N-di$C_{1-2}$alkylaminosulfonyl" refers to a radical of the formula $R_x(R_x)NS(O)_2$ where each $R_x$ is independently a $C_{1-2}$alkyl radical as generally defined above.

As used herein, the term "$C_{1-3}$alkylaminocarbonyl" refers to a radical of the formula $R_xNHC(O)$— where $R_x$ is a $C_{1-3}$alkyl radical as generally defined above.

As used herein, the term "N,N-di$C_{1-3}$alkylaminocarbonyl" refers to a radical of the formula $(R_x)R_xNHC(O)$— where each R, is independently a $C_{1-3}$alkyl radical as generally defined above.

As used herein, the term "N—$C_{1-3}$alkylaminodicarbonyl" refers to a radical of the formula $R_xNH[C(O)]_2$— where $R_x$ is a $C_{1-3}$alkyl radical as generally defined above.

As used herein, the term "N,N-di$C_{1-3}$alkylaminodicarbonyl" refers to a radical of the formula $(R_x)R_xNH[C(O)]_2$— where each $R_x$ is independently a $C_{1-3}$alkyl radical as generally defined above. The term N,N-di$C_{1-2}$alkylaminodicarbonyl should be construed accordingly.

As used herein, the term "N,N-di$C_{1-3}$alkylaminocarbonyl$C_{1-2}$alkyl" refers to a radical of the formula $(R_x)R_xNHC(O)R_y$— where each $R_x$ is independently a $C_{1-3}$alkyl radical as generally defined above, and $R_y$ is a $C_{1-2}$alkylene radical as generally defined above.

As used herein, the term "$C_{3-6}$cycloalkyl" refers to a stable, monocyclic ring radical which is saturated or partially unsaturated and contains 3 to 6 carbon atoms. $C_{3-5}$cycloalkyl and $C_3$cycloalkyl are to be construed accordingly. Examples of $C_{3-6}$cycloalkyl include, but are not limited to cyclopropyl, cyclobutyl, cyclopentyl, cyclopenten-1-yl, cyclopenten-3-yl, and cyclohexen-3-yl.

As used herein, the term "$C_{3-6}$cycloalkyl$C_{1-2}$alkyl" refers to a $C_{3-6}$cycloalkyl ring as defined above attached to the rest of the molecule by a $C_{1-2}$alkylene radical as defined above. Examples of $C_{3-6}$cycloalkyl$C_{1-3}$alkyl include, but are not limited to cyclopropyl-methyl and cyclobutyl-ethyl.

As used herein, the term "phenyl$C_{1-2}$alkyl" refers to a phenyl ring attached to the rest of the molecule by a $C_{1-2}$alkylene radical as defined above. Examples of phenyl$C_{1-2}$alkyl include, but are not limited to, benzyl.

As used herein, the term "heteroaryl" generally refers to a 5- or 6-membered monocyclic aromatic ring radical which comprises 1, 2, 3 or 4 heteroatoms individually selected from nitrogen, oxygen and sulfur. The heteroaryl radical is bonded to the rest of the molecule via a carbon atom or heteroatom. Examples of heteroaryl include but are not limited to, furyl, pyrrolyl, thienyl, pyrazolyl, imidazolyl, thiazolyl, oxazolyl, isoxazolyl, triazolyl, tetrazolyl, pyrazinyl, pyridazinyl, pyrimidyl, pyridyl, and indolyl.

As used herein, the term "heteroaryl$C_{1-2}$alkyl" refers to a heteroaryl as generally defined above, attached to the rest of the molecule by a $C_{1-2}$alkylene radical as defined above.

As used herein, the term "heterocyclyl" or "heterocyclic" generally refers to a stable, saturated or partially saturated, 4- to 6-membered, non-aromatic monocyclic ring, which comprises 1, 2 or 3 heteroatoms individually selected from nitrogen, oxygen and sulfur. The heterocyclyl radical may be bonded to the rest of the molecule via a carbon atom or heteroatom. Examples of heterocyclyl include, but are not limited to, azetidinyl, oxetanyl, pyrrolidyl, tetrahydrofuryl, tetrahydrothienyl, tetrahydrothiopyranyl, piperidinyl, piperazinyl, tetrahydropyranyl, dioxolanyl, and morpholinyl.

As used herein, the term "heterobicyclyl" or "heterobicyclic" refers to a stable, 7- to 9-membered saturated, partially saturated or aromatic fused ring or saturated spirocyclic ring radical containing 1 nitrogen, which comprises 1 or 2 additional ring members individually selected from nitrogen, oxygen and sulfur. The heterobicyclyl radical is bonded to the rest of the molecule via a nitrogen atom. Examples of heterobicyclyl include, but are not limited to, pyrrolopyridine, benzimidazole.

The presence of one or more possible asymmetric carbon atoms in a compound of Formula (I) means that the compounds may occur in chiral isomeric forms, i.e., enantiomeric or diastereomeric forms. Also, atropisomers may occur as a result of restricted rotation about a single bond. Formula (I) is intended to include all those possible isomeric forms and mixtures thereof. The present invention includes all those possible isomeric forms and mixtures thereof for a compound of Formula (I). Likewise, Formula (I) is intended to include all possible tautomers (including lactam-lactim tautomerism and keto-enol tautomerism) where present. The present invention includes all possible tautomeric forms for a compound of Formula (I).

In each case, the compounds of Formula (I) according to the invention are in free form, in oxidized form as an N-oxide, in covalently hydrated form, or in salt form, e.g., an agronomically usable or agrochemically acceptable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The following list provides definitions, including preferred definitions, for substituents A (A-1, A-2, A-3), $R^1$, $R^2$, Z (including $Z^1$, $Z^2$, $Z^3$), $R^3$, $R^4$, $R^5$ (including $R^a$, $R^b$, $R^c$, $R^d$, $R^e$, $R^f$), $R^6$ and $R^7$, with reference to the compounds of Formula (I) according to the invention. For any one of these substituents, any of the definitions given below may be combined with any definition of any other substituent given below or elsewhere in this document.

A is selected from A-1, A-2, and A-3, A-1 represents a 2,5-thienyl group, A-2 represents a 2,4-thienyl group, and A-3 represents a 3,5-thienyl group. Preferably, A is A-1.

$R^1$ and $R^2$ independently represent hydrogen, methyl, ethyl, fluoro, cyano, difluoromethyl or trifluoromethyl. Preferably, $R^1$ and $R^2$ independently represent hydrogen or methyl, more preferably $R^1$ and $R^2$ both represent hydrogen.

Z is selected from $Z^1$, $Z^2$, and $Z^3$.

$Z^1$ represents a 4-, 5- or 6-membered non-aromatic heterocyclyl ring containing 1 ring nitrogen, wherein the heterocyclyl optionally comprises 1 or 2 additional ring members independently selected from N, O, S, C(O) and S(O)$_2$ with the proviso that the heterocyclyl cannot contain 2 contiguous atoms selected from O and S, or the heterocyclyl optionally comprises 1 additional ring member NR$^3$, wherein the heterocyclyl is optionally substituted by 1 or 2 substituents, which may be the same or different, selected from R$^4$, and wherein further the heterocyclyl is bound to the rest of the molecule through a ring nitrogen.

Preferably, $Z^1$ represents a 4-, 5- or 6-membered non-aromatic heterocyclyl containing 1 ring nitrogen, wherein the heterocyclyl optionally comprises 1 additional ring member independently selected from N, O, S. C(O) or S(O)$_2$ (in particular, O or C(O)), wherein the heterocyclyl is optionally substituted by 1 or 2 substituents, which may be the same or different, selected from R$^4$, and wherein further the heterocyclyl is bound to the rest of the molecule through a ring nitrogen.

More preferably, $Z^1$ is selected from:

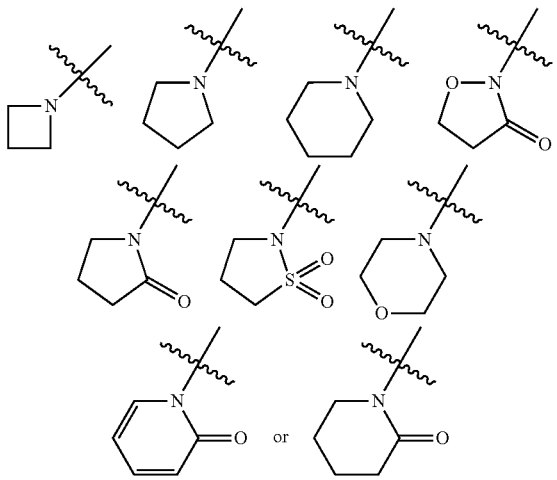

wherein $Z^1$ is optionally substituted by 1 or 2 substituents, which may be the same or different, selected from R$^4$.

In certain embodiments of the invention, $Z^1$ is optionally substituted by 1 substituent selected from R$^4$.

$R^3$ represents hydrogen, hydroxy, amino, formyl, $C_{1-3}$alkyl, $C_{1-3}$alkoxy, $C_{1-3}$alkylcarbonyl, $C_{1-3}$alkoxycarbonyl, N—$C_{1-3}$alkylaminocarbonyl, N,N-di$C_{1-3}$alkylaminocarbonyl, N—$C_{1-3}$alkoxyaminocarbonyl, N—$C_{1-3}$alkyl-N—$C_{1-3}$alkoxy-aminocarbonyl, $C_{1-2}$alkylsulfonyl, N—$C_{1-2}$alkylaminosulfonyl, N,N-di$C_{1-2}$ alkylaminosulfonyl, $C_{1-2}$alkyldicarbonyl, $C_{1-2}$alkoxydicarbonyl, N—$C_{1-2}$alkylaminodicarbonyl or N,N-di$C_{1-2}$alkylaminodicarbonyl.

$R^4$ represents cyano, halogen, hydroxy, amino, methyl, ethyl, difluoromethyl, trifluoromethyl, methoxy, N-methylamino or N,N-dimethylamino. Preferably, $R^4$ is selected from methyl or ethyl.

$Z^2$ represents a 5- or 6-membered heteroaryl ring containing 1 ring nitrogen, wherein the heteroaryl optionally comprises 1, 2 or 3 additional ring members independently selected from O, S, or N, and wherein the heteroaryl is optionally substituted by: 1 or 2 substituents selected from R$^5$, 1 substituent selected from R$^6$, or 1 substituent selected from R$^5$ and 1 substituent selected from R$^6$, and wherein further the heteroaryl is bound to the rest of the molecule through a ring nitrogen;

In certain preferred embodiments of the invention, $Z^2$ is optionally substituted by 1 or 2 substituents selected from R$^5$, and most preferably is optionally substituted by a single substituent selected from R$^5$.

Preferably, $Z^2$ is selected from:

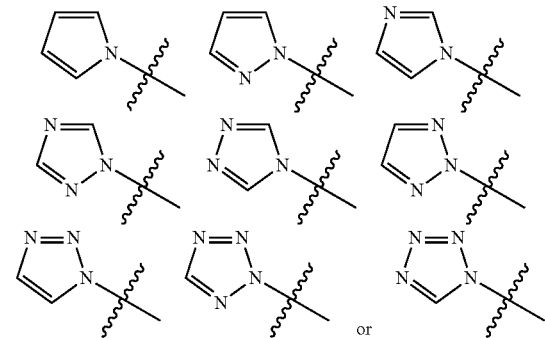

wherein $Z^2$ is optionally substituted by: 1 or 2 substituents selected from $R^5$, 1 substituent selected from $R^6$, or 1 substituent selected from $R^5$ and 1 substituent selected from $R^6$.

More preferably, $Z^2$ is selected from:

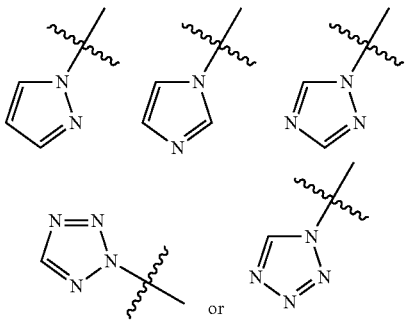

or wherein $Z^2$ is optionally substituted by: 1 or 2 substituents selected from $R^5$, 1 substituent selected from $R^5$, or 1 substituent selected from $R^5$ and 1 substituent selected from $R^6$.

$R^5$ represents hydroxyl, amino, cyano, halogen, formyl, nitro, $C_{1-4}$alkyl, $C_{1-4}$alkoxy, $C_{3-4}$alkenyl, $C_{3-4}$alkynyl, $C_{3-4}$alkenyloxy, $C_{3-4}$alkynyloxy, cyano$C_{1-2}$alkyl, $C_{1-2}$haloalkyl, hydroxy$C_{1-2}$alkyl, $C_{1-2}$alkoxy$C_{1-2}$alkyl, $C_{1-2}$alkoxy$C_{1-2}$alkoxy$C_{1-2}$alkyl, N,N-dimethylamino, $C_{1-3}$alkoxycarbonyl$C_{1-2}$alkyl, $C_{1-2}$alkylcarbonyloxy$C_{1-2}$alkyl, N—$C_{1-3}$alkylaminocarbonyl$C_{1-2}$alkyl, N,N-di$C_{1-3}$alkylaminocarbonyl$C_{1-2}$alkyl, $C_{1-2}$alkylsulfonyl, $C_{1-3}$alkylcarbonyl, $C_{1-3}$alkyldicarbonyl, $C_{1-3}$alkoxydicarbonyl, N—$C_{1-3}$alkylaminodicarbonyl, or N,N-di$C_{1-3}$alkylaminodicarbonyl; or $R^5$ represents —C(O)N($R^a$)($R^b$), wherein:

$R^a$ represents hydrogen, $C_{1-6}$alkyl, $C_{3-4}$alkenyl, $C_{3-4}$alkynyl, $C_{1-3}$haloalkyl, $C_{3-4}$haloalkenyl, $C_{1-4}$alkoxy, $C_{1-2}$alkoxy$C_{1-3}$alkyl, $C_{2-3}$haloalkoxy, $C_{3-4}$alkenyloxy, $C_{1-4}$alkynyloxy, N—$C_{1-3}$akylamino, or N,N-di$C_{1-2}$alkylamino; or $R^a$ represents $C_{3-5}$cycloalkyl, $C_{3-5}$cycloalkyl$C_{1-2}$alkyl, phenyl, phenyl$C_{1-2}$alkyl, heterocyclyl, heterocyl$C_{1-2}$alkyl, wherein the heterocyclyl moiety is a 4- to 6-membered non-aromatic ring which comprises 1 or 2 heteroatoms independently selected from N, O or S, with the proviso that the heterocyclyl cannot contain 2 contiguous atoms selected from O and S, heteroaryl or heteroaryl$C_{1-2}$alkyl, wherein the heteroaryl moiety is a 5- or 6-membered aromatic ring which comprises 1, 2, 3, or 4 heteroatoms individually selected from N, O and S; wherein the cycloalkyl, phenyl, heterocyclyl or heteroaryl is optionally substituted by 1 or 2 substituents, which may be the same or different, selected from hydroxyl, amino, formyl, acyl, cyano, halogen, methyl, trifluoromethyl, methoxy, or N,N-dimethylamino, and wherein when $R^a$ represents cycloalkyl or heterocyclyl, these cycles optionally contain 1 group selected from C(O) or S(O)$_2$; and $R^b$ represents hydrogen, methyl, ethyl, propyl, prop-2-enyl, prop-2-ynyl, cyclopropyl, or cyclopropylmethyl; or $R^a$ and $R^b$, together with the nitrogen atom they share, form an azetidinyl, pyrrolidinyl or piperidinyl ring optionally substituted by 1 or 2 groups selected from halogen, methyl, ethyl or methoxy; or $R^5$ represents —C(O)O—$R^c$, wherein:

$R^c$ represents hydrogen, $C_{1-6}$alkyl, $C_{3-5}$alkenyl, $C_{3-5}$alkynyl, $C_{1-3}$haloalkyl, $C_{3-4}$haloalkenyl, N,N-di$C_{1-3}$alkylamino$C_{1-3}$alkyl, $C_{3-6}$cycloalkyl, $C_{3-4}$cycloalkyl$C_{1-2}$alkyl, phenyl, heterocycyl, wherein the heterocyclyl moiety is a 4- to 6-membered non-aromatic ring which comprises 1 or 2 heteroatoms independently selected from O, S and N, with the proviso that the heterocycyl cannot contain 2 contiguous atoms selected from O and S, heteroaryl, wherein the heteroaryl moiety is a 5- or 6-membered aromatic ring which comprises 1, 2 or 3 heteroatoms individually selected from N, O and S; and wherein the cycloalkyl, phenyl, heterocyclyl or heteroaryl is optionally substituted by 1 or 2 substituents, which may be the same or different, selected from hydroxyl, amino, formyl, methylcarbonyl, cyano, halogen, methyl, trifluoromethyl, methoxy, or N,N-dimethylamino, and wherein when $R^c$ represents cycloalkyl or heterocyclyl, these cycles optionally contain 1 group selected from C(O) or S(O)$_2$; or $R^5$ represents —N($R^d$)($R^e$) or —$C_{1-2}$alkyl-N($R^d$)($R^e$), wherein $R^d$ represents $C_{1-3}$alkyl, $C_{3-4}$alkenyl, $C_{3-4}$alkynyl, methylcarbonyl, methoxycarbonyl, N-methylaminocarbonyl, N,N-dimethylaminocarbonyl, N-methoxyaminocarbonyl, N-methyl-N-methoxyaminocarbonyl, methylsulfonyl, N-methylaminosulfonyl, N,N-dimethylaminosulfonyl, methyldicarbonyl, N-methylaminodicarbonyl, or N,N-dimethylaminodicarbonyl; and $R^e$ represents hydrogen, methyl, ethyl, or propyl; or $R^5$ represents —CH=N($R^f$), wherein $R^f$ represents $C_{1-4}$alkyl, $C_{1-4}$alkoxy, $C_{2-4}$alkenoxy, or $C_{2-4}$alkynoxy;

$R^6$ represents $C_{3-6}$cycloalkyl, phenyl, heteroaryl, wherein the heteroaryl moiety is a 5- or 6-membered aromatic ring which comprises 1, 2, 3 or 4 heteroatoms individually selected from N, O and S, heterocyclyl, wherein the heterocyclyl moiety is a 4- to 6-membered non-aromatic ring which comprises 1 or 2 heteroatoms individually selected from N, O and S, and wherein the cycloalkyl, phenyl, heteroaryl and heterocyclyl is optionally substituted by 1 or 2 substituents, which may be the same or different, selected from hydroxyl, amino, formyl, acyl, cyano, halogen, methyl, trifluoromethyl, methoxy, N,N-dimethylamino, and wherein when $R^6$ represents cycloalkyl or heterocyclyl, these cycles optionally contain 1 group selected from C(O) or S(O)$_2$.

Preferably, $R^5$ is independently selected from hydroxy, amino, cyano, halogen, formyl, nitro, $C_{1-4}$ alkyl, $C_{1-4}$alkoxy, $C_{1-2}$haloalkyl, $C_{1-2}$alkoxy$C_{1-2}$alkyl, N,N-dimethylamino, —C(O)O—$R^c$ wherein $R^c$ is $C_{1-4}$ alkyl, and —C(O)N($R^a$)($R^b$), wherein $R^a$ is selected from hydrogen, $C_{1-4}$alkyl or $C_{1-4}$alkoxy, and $R^b$ is selected from hydrogen or methyl, and $R^6$ is phenyl optionally substituted by 1 or 2 substituents, which may be the same or different, selected from hydroxyl, methyl, methoxy, cyano, fluoro, chloro or bromo.

More preferably, $R^5$ is selected from amino, cyano, chloro, fluoro, formyl, nitro, methyl, ethyl, difluoromethyl, methoxymethyl, N,N-dimethylamino, methoxycarbonyl, ethoxycarbonyl or n-propoxycarbonyl; or —C(O)N($R^a$)($R^b$) wherein $R^a$ is selected from hydrogen, methyl or methoxy and $R^b$ is selected from hydrogen or methyl, and $R^d$ is phenyl optionally substituted by 1 or 2 substituents, which may be the same or different, selected from fluoro, chloro or bromo.

$Z^3$ represents a heterobicyclyl which is a 7- to 9-membered saturated, partially saturated, or aromatic fused ring or saturated spirocyclic ring system containing 1 nitrogen, wherein the heterobicyclyl optionally comprises 1 or 2 additional ring members independently selected from N, O, S, C(O) and S(O)$_2$ with the proviso that the heterobicyclyl cannot contain 2 contiguous atoms selected from O and S, wherein the heterobicyclyl is optionally substituted by 1 substituent selected from $R^7$, and wherein further the heterobicyclyl is bound to the rest of the molecule through a ring nitrogen; and Preferably, $Z^3$ represents a heterobicyclyl which is a 9-membered saturated, partially saturated, or aromatic fused ring system containing 1 nitrogen, wherein the heterobicyclyl optionally comprises 1 additional ring member independently selected from N, O and S, wherein the heterobicyclyl is optionally substituted by 1 substituent selected from $R^7$, and wherein further the heterobicyclyl is bound to the rest of the molecule through a ring nitrogen.

More preferably, $Z^3$ is selected from:

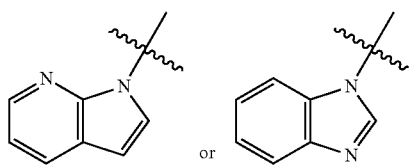

wherein $Z^3$ is optionally substituted by 1 substituent selected from $R^7$.

$R^7$ is cyano, fluoro, chloro, amino, hydroxy, methyl, difluoromethyl, trifluoromethyl, methoxy, N,N-dimethylamino, formyl, methylcarbonyl, methoxycarbonyl, N-methylaminocarbonyl, or N,N-dimethylaminocarbonyl.

Preferably, $R^7$ is selected from hydroxyl, methoxy, methyl cyano, fluoro or chloro.

Preferably, the compound according to Formula (I) is selected from a compound 1.1 to 1.190 listed in Table T1 (below).

Preferably, in a compound according to Formula (I) of the invention:
A is A-1;
$R^1$ is hydrogen and $R^2$ is hydrogen or methyl;
Z is $Z^1$, wherein $Z^1$ represents a 4-, 5- or 6-membered non-aromatic heterocyclyl containing 1 ring nitrogen, wherein the heterocyclyl optionally comprises 1 additional ring member independently selected from N, O, S, C(O) or S(O)$_2$ (in particular, O or C(O)), wherein the heterocyclyl is optionally substituted by 1 or 2 substituents, which may be the same or different, selected from $R^4$, and wherein further the heterocyclyl is bound to the rest of the molecule through a ring nitrogen; and
$R^4$ represents cyano, halogen, hydroxy, amino, methyl, ethyl, difluoromethyl, trifluoromethyl, methoxy, N-methylamino or N,N-dimethylamino.
More preferably,
A is A-1;
$R^1$ and $R^2$ are hydrogen;
Z is $Z^1$, wherein $Z^1$ represents a 4-, 5- or 6-membered non-aromatic heterocyclyl containing 1 ring nitrogen, wherein the heterocyclyl optionally comprises 1 additional ring member independently selected from N, O, S, C(O) or S(O)$_2$ (in particular, O or C(O)), wherein the heterocyclyl is optionally substituted by 1 or 2 substituents, which may be the same or different, selected from $R^4$, and wherein further the heterocyclyl is bound to the rest of the molecule through a ring nitrogen; and
$R^4$ represents methyl or ethyl.
Preferably, in a compound according to Formula (I) of the invention:
A is A-1;
$R^1$ is hydrogen and $R^2$ is hydrogen or methyl; and
Z is $Z^2$, wherein $Z^2$ is selected from:

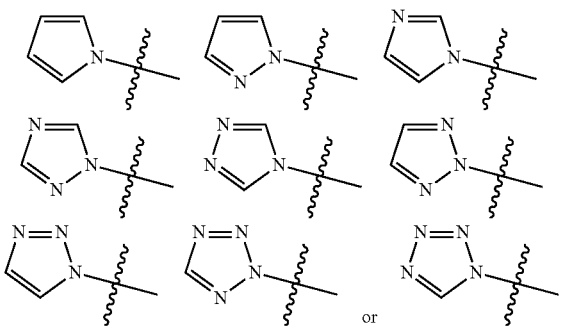

wherein $Z^2$ is optionally substituted by: 1 or 2 substituents selected from $R^5$, 1 substituent selected from $R^6$, or 1 substituent selected from $R^5$ and 1 substituent selected from $R^6$.
More preferably,
A is A-1;
$R^1$ and $R^2$ are hydrogen; and
Z is $Z^2$, wherein $Z^2$ is selected from:

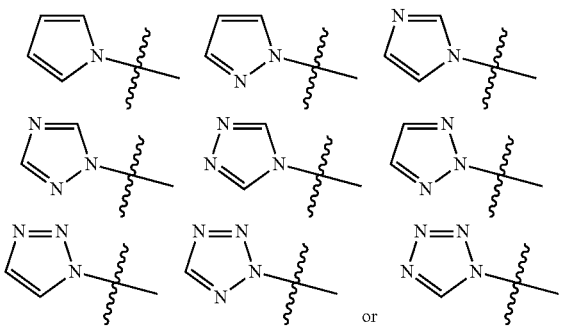

wherein $Z^2$ is optionally substituted by: 1 or 2 substituents selected from $R^5$ or 1 substituent selected from $R^6$.
Preferably, in a compound according to Formula (I) of the invention:
A is A-1;
$R^1$ is hydrogen and $R^2$ is hydrogen or methyl; and
Z is $Z^3$, wherein $Z^3$ represents a heterobicyclyl which is a 9-membered saturated, partially saturated, or aromatic fused ring system containing 1 nitrogen, wherein the heterobicyclyl optionally comprises 1 additional ring member independently selected from N, O and S, wherein the heterobicyclyl is optionally substituted by 1 substituent selected from $R^7$, and wherein further the heterobicyclyl is bound to the rest of the molecule through a ring nitrogen;
More preferably,
A is A-1;
$R^1$ and $R^2$ are hydrogen;
Z is $Z^3$, wherein $Z^3$ represents a heterobicyclyl which is a 9-membered saturated, partially saturated, or aromatic fused ring system containing 1 nitrogen, wherein the heterobicyclyl optionally comprises 1 additional ring member independently selected from N, O and S, wherein the heterobicyclyl is optionally substituted by 1 substituent selected from $R^7$, and wherein further the heterobicyclyl is bound to the rest of the molecule through a ring nitrogen; and R⁷ is selected from hydroxyl, methoxy, methyl cyano, fluoro or chloro.

The compounds of the present invention may be enantiomers of the compound of Formula (I) as represented by a Formula (Ia) or a Formula (Ib), wherein $R^1$ and $R^2$ are different substituents.

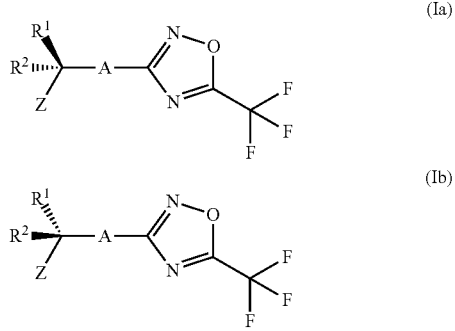

It is understood that when in aqueous media, the compounds of Formula (I) according to the invention may be present in a reversible equilibrium with the corresponding covalently hydrated forms (i.e., the compounds of Formula (I-Ia) and Formula (I-IIa) as shown below, which may exist in tautomeric form as the compounds of formula (I-Ib) and formula (I-IIb)) at the CF₃-oxadiazole motif. This dynamic equilibrium may be important for the biological activity of the compounds of Formula (I). The designations of A (A-1, A-2, A-3), $R^1$, $R^2$, Z (including $Z^1$, $Z^2$, $Z^3$), $R^3$, $R^4$, $R^5$ (including $R^a$, $R^b$, $R^c$, $R^d$, $R^e$, $R^f$), $R^6$ and $R^7$, with reference to the compounds of Formula (I) of the present invention apply generally to the compounds of Formula (I-Ia), Formula (I-Ib), Formula (I-IIa), and Formula (I-IIb), as well do the specific disclosures of combinations of A (A-1, A-2, A-3), $R^1$, $R^2$, Z (including $Z^1$, Z, $Z^3$), $R^3$, $R^4$, $R^5$ (Including $R^a$, $R^b$, $R^c$, $R^d$, $R^e$, $R^f$), $R^6$ and $R^7$, as represented in Tables 1.1 to 1.3, Tables 2.1 and 2.2, or the compounds 1.1 to 1.190 according to the invention listed in Table T1 (below).

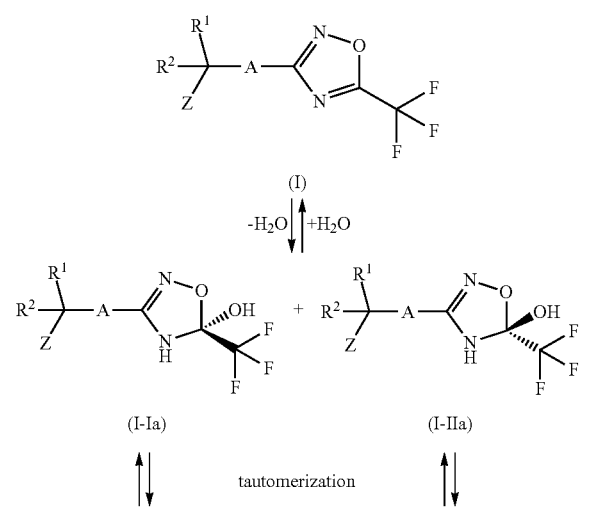

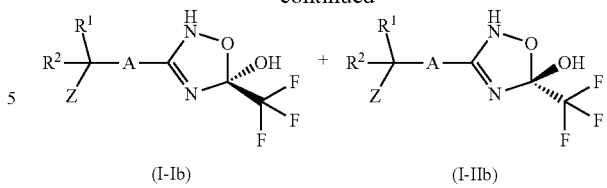

Compounds of the present invention can be made as shown in the following schemes 1 to 10, in which, unless otherwise stated, the definition of each variable is as defined above for a compound of Formula (I).

Compounds of Formula (I) can be prepared from compounds of Formula (II), wherein X is OSO₂CH₃, Cl, Br, or I, via treatment with compounds of Formula (III), in the presence of a base (e.g. triethylamine, N,N-di-isopropylethylamine, K₂CO₃, NaHCO₃, Na₂CO₃, Cs₂CO₃, or NaH) in a suitable solvent (e.g. dimethylacetamide, tetrahydrofuran, 2-methyltetrahydrofuran, acetone, toluene, or acetonitrile) at a temperature between 25° C. and 110° C. In some cases, a better reaction performance may be gained from the use of a catalyst (e.g., Bu₄NHSO₄, Bu₄NBr, Bu₄NI, NaI, or 4-dimethylaminopyridine) and microwave irradiation. Furthermore, compounds of formula (I), can optionally be obtained via a coupling transformation with compounds of formula (III) and compounds of formula (II), wherein X is OH, via a process that converts the —OH into an improved leaving group, such as a —OSO₂CH₃ group, for example by using methanesulfonyl chloride (ClSO₂Me), prior to treatment with the compounds of formula (III). For related examples, see: WO 2013/132253, WO 2017/118689, and Garcia, M. et al *Org. Biomol. Chem.* (2004), 11, 1633. This reaction is shown in Scheme 1.

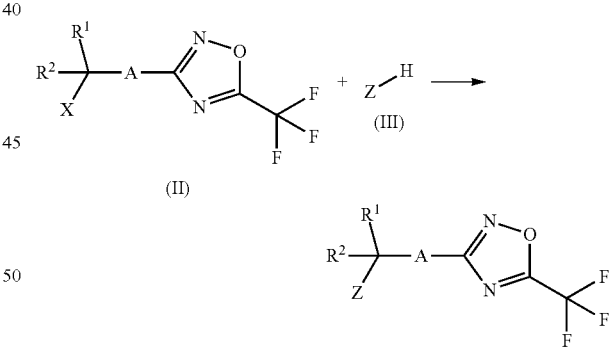

Compounds of Formula (II), wherein X is halogen, preferably Cl or Br, can be prepared from compounds of Formula (IV) by treatment with a halogen source (e.g., N-bromosuccinimide (NBS) or N-chlorosuccinimide (NCS)) and a radical initiator (e.g., (PhCO₂)₂ or azobisisobutyronitrile (AIBN)) in a suitable solvent, such as tetrachloromethane, at temperatures between 55° and 100° C. in the presence of ultraviolet light. For related examples, see Liu, S. et al *Synthesis* (2001), 14, 2078, WO 2017/118689, and Kompella, A. et al *Org. Proc. Res. Dev.* (2012), 16, 1794. This reaction is shown in Scheme 2.

Scheme 2

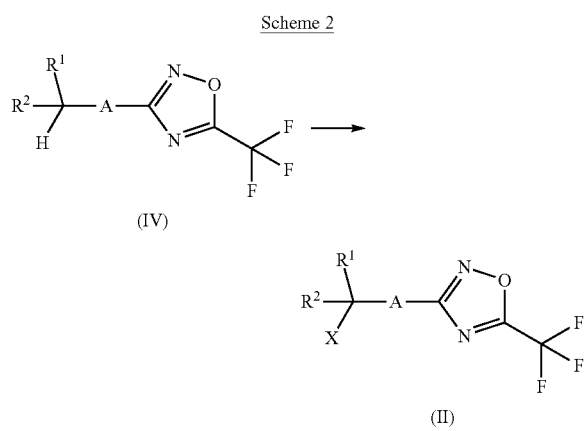

Alternatively, compounds of Formula (II), wherein X is hydrogen, OH, Cl, Br, or I, can be prepared from compounds of Formula (V) by treatment with trifluoroacetic anhydride or trifluoroacetyl halide (including trifluoroacetyl fluoride, trifluoroacetyl chloride and trifluoroacetyl bromide) in the presence of a base (e.g., pyridine or 4-dimethylaminopyridine) in a suitable solvent, (e.g., ethyl acetate, tetrahydrofuran, 2-methyl tetrahydrofuran, or ethanol), at a temperature between 0° C. and 75° C. For related examples, see WO 2003/028729, WO 2017/055473, and WO 2010/045251. This reaction is shown in Scheme 3.

Scheme 3

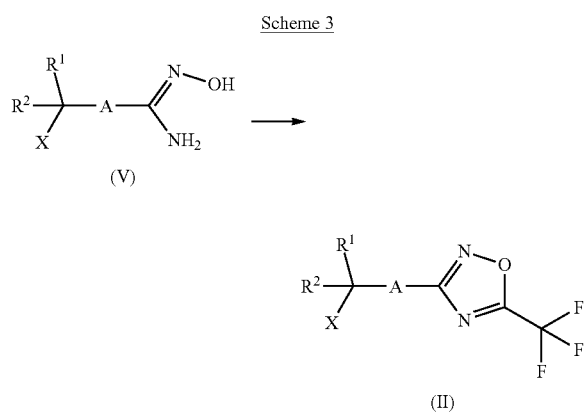

Compounds of Formula (V), wherein X is hydrogen, OH, or halogen, can be prepared from compounds of Formula (VI) by treatment with a hydroxylamine hydrochloride salt or a hydroxylamine solution in water, in the presence of a base, such as triethylamine or potassium carbonate, in a suitable solvent, such as methanol or ethanol, at a temperature between 0° C. and 80° C. In some cases, a better reaction performance may be gained from the use of a catalyst (e.g., 8-hydroxyquinoline). For related examples, see Kitamura, S. et al *Chem. Pharm. Bull.* (2001), 49, 268, WO 2017/055473 and WO 2013/066838. This reaction is shown in Scheme 4.

Scheme 4

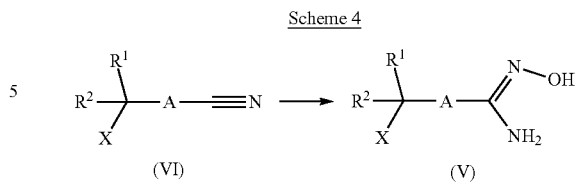

Compounds of Formula (VI), can be prepared from compounds of Formula (VII), wherein Y is Cl, Br or I, via metal-promoted reaction with a suitable cyanide reagent, such as Pd(0)/Zn(CN)$_2$ or CuCN, in a suitable solvent (e.g., dimethylformamide or N-methylpyrrolidone) at elevated temperature between 100° C. and 120° C. For related examples, see US 2007/0155739 and WO 2009/022746. This reaction is shown in Scheme 5.

Scheme 5

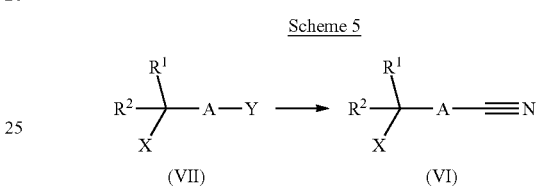

Compounds of Formula (VII), wherein X is Cl, Br, I or OSO$_2$Me and Y is Cl, Br, I or CN, are either commercially available or can be prepared from compounds of Formula (VIII), via treatment with an acid source (e.g., hydrochloric acid, hydrobromic acid, or hydroiodic acid), or with a halogen source (e.g., CCl$_3$Br, CCl$_4$ or I$_2$) in the presence of triphenylphosphine, or with methanesulfonyl chloride (ClSO$_2$Me), in a suitable solvent, (e.g., dichloromethane) at a temperature between 0° C. and 100° C. For related examples, see Liu, H. et al *Bioorg. Med. Chem.* (2008), 16, 10013, WO 2014/020350 and Kompella, A. et al *Bioorg. Med. Chem. Lett.* (2001), 1, 3161. Compounds of formula (VII) are commercially available or prepared using known methods. This reaction is shown in Scheme 6.

Scheme 6

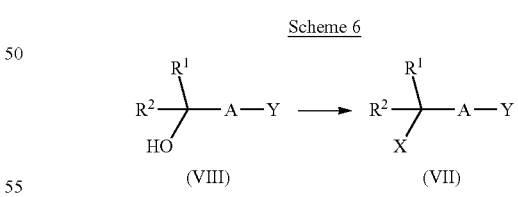

Alternatively, compounds of Formula (I) can be prepared from compounds of Formula (IX) by treatment with trifluoroacetic anhydride or trifluoroacetyl halide (including trifluoroacetyl fluoride, trifluoroacetyl chloride and trifluoroacetyl bromide) in the presence of a base (e.g., pyridine or 4-dimethylaminopyridine) in a suitable solvent, (e.g., ethyl acetate, tetrahydrofuran, 2-methyl tetrahydrofuran, or ethanol), at a temperature between 0° C. and 75° C. For related examples, see WO 2003/028729, WO 2017/118689, and WO 2010/045251. This reaction is shown in Scheme 7.

Scheme 7

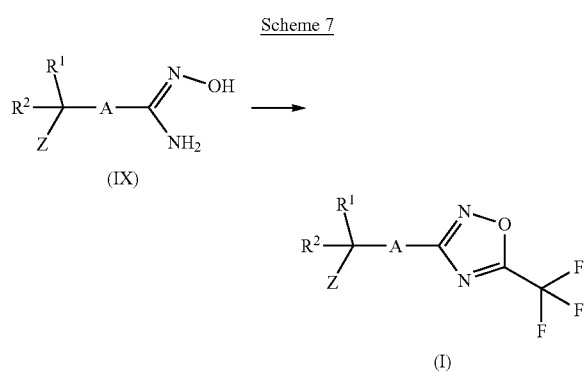

Compounds of Formula (IX), can be prepared from compounds of Formula (X) by treatment with a hydroxylamine hydrochloride salt or a hydroxylamine solution in water, in the presence of a base, such as triethylamine or $K_2CO_3$, in a suitable solvent, such as methanol or ethanol, at a temperature between 0° C. and 100° C. In some cases, a better reaction performance may be gained from the use of a catalyst (e.g., 8-hydroxyquinoline). For related examples, see Kitamura, S. et al. *Chem. Pharm. Bull.* (2001), 49, 268 and WO 2013/066838. This reaction is shown in Scheme 8.

Scheme 8

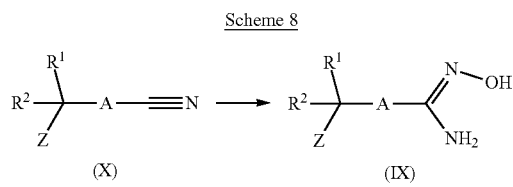

Compounds of Formula (X), can be prepared from compounds of Formula (XI), wherein Y is Cl, Br or I, via metal-promoted reaction with a suitable cyanide reagent, such as $Pd(O)/Zn(CN)_2$ or CuCN, in a suitable solvent (e.g., dimethylformamide or N-methylpyrrolidone) at elevated temperature between 80° C. and 120° C. For related examples, see US 2007/0155739, WO 2017/118689, and WO 2009/022746. This reaction is shown in Scheme 9.

Scheme 9

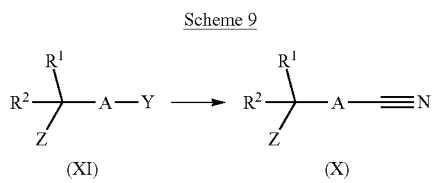

Compounds of Formula (XI), wherein Y is CN, Cl, Br, or I, can be prepared from compounds of Formula (VII), wherein X is $OSO_2CH_3$, Cl, Br, or I, via treatment with compounds of Formula (III), in the presence of a base (e.g., triethylamine, N,N-di-isopropylethylamine, $K_2CO_3$, $NaHCO_3$, $Na_2CO_3$, $Cs_2CO_3$, or NaH) in a suitable solvent (e.g., dimethylacetamide, tetrahydrofuran, 2-methyltetrahydrofuran, acetone, toluene, or acetonitrile) at a temperature between 25° C. and 110° C. In some cases, a better reaction performance may be gained from the use of a catalyst (e.g., $Bu_4NHSO_4$, $Bu_4NBr$, $Bu_4NI$, NaI, or 4-dimethylaminopyridine) and microwave irradiation. Furthermore, compounds of formula (XI), can optionally be obtained via a coupling transformation with compounds of formula (III) and compounds of formula (VII), wherein X is OH, via a process that converts the —OH into an improved leaving group, such as a —$OSO_2CH_3$ group, for example by using methanesulfonyl chloride ($ClSO_2Me$), prior to treatment with the compounds of formula (III). Compounds of formula (III) are commercially available or prepared using known methods. For related examples, see: WO 2013/132253, WO 2017/118689, and Garcia, M. et al *Org. Biomol. Chem.* (2004), 11, 1633. This reaction is shown in Scheme 10.

Scheme 10

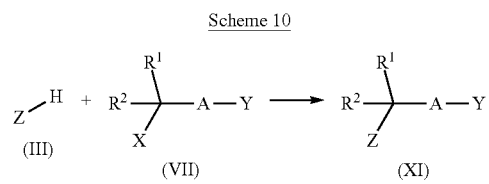

As already indicated, surprisingly, it has now been found that the compounds of Formula (I) of the present invention have, for practical purposes, a very advantageous level of biological activity for protecting plants against diseases that are caused by fungi.

The compounds of Formula (I) can be used in the agricultural sector and related fields of use, e.g., as active ingredients for controlling plant pests or on non-living materials for the control of spoilage microorganisms or organisms potentially harmful to man. The novel compounds are distinguished by excellent activity at low rates of application, by being well tolerated by plants and by being environmentally safe. They have very useful curative, preventive and systemic properties and can be used for protecting numerous cultivated plants. The compounds of Formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of Formula (I) is applied to the plants, to parts thereof or the locus thereof.

It is also possible to use compounds of Formula (I) as a fungicide. The term "fungicide" as used herein means a compound that controls, modifies, or prevents the growth of fungi. The term "fungicidally effective amount" where used means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It may also be possible to use compounds of Formula (I) as dressing agents for the treatment of plant propagation material, e.g., seed, such as fruits, tubers or grains, or plant cuttings, for the protection against fungal infections as well as against phytopathogenic fungi occurring in the soil. The propagation material can be treated with a composition comprising a compound of Formula (I) before planting:

seed, for example, can be dressed before being sown. The active compounds of Formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore, the compounds of Formula (I) can be used for controlling fungi in related areas, for example in the protection of technical materials, including wood and wood related technical products, in food storage, in hygiene management.

In addition, the invention could be used to protect non-living materials from fungal attack, e.g. lumber, wan boards and paint.

The compounds of Formula (I) are for example, effective against fungi and fungal vectors of disease as well as phytopathogenic bacteria and viruses. These fungi and fungal vectors of disease as well as phytopathogenic bacteria and viruses are for example:

*Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremla lactucae, Botryosphaeria* spp. including *B. dothidea, B. obtusa, Botrytis* spp. including *B. cinerea, Candida* spp. including *C. albicans, C. glabrata, C. krusei, C. lusitaniae, C. parapsilosis, C. tropicalis, Cephaloascus fragrans, Ceratocystis* spp, *Cercospora* spp. including *C. arachidicola, Cercosporidium personatum, Cladosporium* spp, *Claviceps purpurea, Coccidioides immitis, Cochliobolus* spp, *Colietotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella gfujikuroi, Gloeodes pomigena, Gloeosporium musarum, Glomerella cingulate, Guignardia bidwellil, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. dlgitatum, P. italicum, Petriellidium* spp, *Peronosclerospora* spp. including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedi, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. tritcina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca* (*Sphaerotheca fuliginea*), *Sporothorix* spp, *Stagonospora nodorum, Stemphylium* spp., *Stereum hirsutum, Thanatephorus cucumeris, Thielaviopsis basicola, Tilletia* spp, *Trichoderma* spp. including *T. harzianum, T. pseudokoningii, T. viride, Trichophyton* app, *Typhula* spp, *Uncinula necator, Urocystis* spp, *Ustilago* spp, *Venturia* spp. including *V. inaequalis, Verticillium* spp, and *Xanthomonas* spp.

The compounds of Formula (I) may be used for example on turf, ornamentals, such as flowers, shrubs, broad-leaved trees or evergreens, for example conifers, as well as for tree injection, pest management and the like.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as also including useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a. CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a Cry1A(c) toxin); Bollgard I® (cotton variety that expresses a Cry1A(c) toxin); Bollgard II® (cotton variety that expresses a Cry1A(c) and a Cry1IA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus* luminescens, *Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YIeldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B@ (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The compounds of Formula (I) (including any one of compounds 1.1 to 1.190) according to the present invention comprising a compound of Formula (I) may be used in controlling or preventing phytopathogenic diseases, especially phytopathogenic fungi (such as *Phakopsora pachyrhizi*) on soy bean plants.

In particular, transgenic soybean plants expressing toxins, for example insecticidal proteins such as delta-endotoxins, e.g. Cry1Ac (Cry1Ac Bt protein). Accordingly, this may include transgenic soybean plants comprising event MON87701 (see U.S. Pat. No. 8,049,071 and related applications and patents, as well as WO 2014/170327 A1 (eg, see paragraph [008] reference to intacta RR2 PRO™ soybean)), event MON87751 (US. Patent Application Publication No. 2014/0373191) or event DAS-81419 (U.S. Pat. No. 8,632,978 and related applications and patents).

Other transgenic soybean plants may comprise event SYHT0H2-HPPD tolerance (U.S. Patent Application Publication No. 201410201860 and related applications and patents), event MON89788-glyphosate tolerance (U.S. Pat. No. 7,632,985 and related applications and patents), event MON87708-dicamba tolerance (U.S. Patent Application Publication No. US 2011/0067134 and related applications and patents), event DP-356043-5-glyphosate and ALS tolerance (U.S. Patent Application Publication No. US 2010/0184079 and related applications and patents), event A2704-12-glufosinate tolerance (U.S. Patent Application Publication No. US 2008/0320616 and related applications and patents), event DP-305423-1-ALS tolerance (U.S. Patent Application Publication No. US 2008/0312082 and related applications and patents), event A5547-127-glufosinate tolerance (U.S. Patent Application Publication No. US 2008/0196127 and related applications and patents), event DAS-40278-9-tolerance to 2,4-dichlorophenoxyacetic acid and aryloxyphenoxyproplonate (see WO 2011/022469, WO 2011/022470, WO 2011/022471, and related applications and patents), event 127-ALS tolerance (WO 2010/080829 and related applications and patents), event GTS 40-3-2-glyphosate tolerance, event DAS-68416-4-2,4-dichlorophenoxyacetic acid and glufosinate tolerance, event FG72-glyphosate and isoxaflutole tolerance, event BPS-CV127-9-ALS tolerance and GU262-glufosinate tolerance or event SYHT4R-HPPD tolerance.

Under certain circumstances, compounds of Formula (I) according to the present invention when used in controlling or preventing phytopathogenic diseases, especially phytopathogenic fungi (such as *Phakopsora pachyrhizi*) on soy bean plants (in particular any of the transgenic soybean plants as described above), may display a synergistic interaction between the active ingredients.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There can be mentioned for example seeds (In the strict sense), roots, fruits, tubers, bulbs, rhizomes and parts of plants. Germinated plants and young plants which are to be transplanted after germination or after emergence from the soil, may also be mentioned. These young plants can be protected before transplantation by a total or partial treatment by immersion. Preferably "plant propagation material" Is understood to denote seeds.

The compounds of Formula (I) may be used in unmodified form or, preferably, together with the adjuvants conventionally employed in the art of formulation. To this end they may be conveniently Formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin days, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular Formulations include sand, fuller's earth, attapulgite clay, bentonite clays, montmorillonite day, vermiculite, perite, calcium carbonate, brick, pumice, pyrophylite, kaolin, dolomite, plaster, wood flour, ground corn cobs, ground peanut hulls, sugars, sodium chloride, sodium sulphate, sodium silicate, sodium borate, magnesia, mica, Iron oxide, zinc oxide, titanium oxide, antimony oxide, cryolite, gypsum, diatomaceous earth, calcium sulphate and other organic or inorganic materials which absorb or which can be coated with the active compound. Granular Formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, days, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and sold compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallization inhibitors, viscosity modifiers, suspending agents, spray droplet modifiers, pigments, antioxidants, foaming agents, anti-foaming agents, light-blocking agents, compatiblizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

Pesticidal agents are referred to herein using their common name are known, for example, from "The Pesticide Manual", 15th Ed., British Crop Protection Council 2009.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of Formula (I) are normally used in the form of agrochemical compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, mollusdcicides or mixtures of several of these preparations, if desired together with further carriers, surfactants or application promoting adjuvants customarily employed in the art of formulation.

The compounds of Formula (I) may be used in the form of (fungicidal) compositions for controlling or protecting against phytopathogenic microorganisms, comprising as active ingredient at least one compound of Formula (I) or of at least one preferred individual compound as defined herein, in free form or in agrochemically usable salt form, and at least one of the above-mentioned adjuvants.

The invention therefore provides a composition, preferably a fungicidal composition, comprising at least one compound Formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally-active compounds, for example an additional fungicidal active ingredient in addition to the compound of Formula (I).

The compound of Formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following: acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides. oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-1H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanol, (5-Bromo-4-chloro-2-methoxy-pyridin-3-yl)-(2,3,4-trimethoxy-6-methyl-phenyl)-methanone, 2-{2-((E)-3-(2,6-Dichlorophenyl)-1-methyl-prop-2-en-(ylideneaminooxymethyl-phenyl}-2-[(Z)-methoxyimino]-methyl-acetamide, 3-[5-(4-Chloro-phenyl)-2,3-dimethyl-isoxazolidin-3-yl]-pyridine, (E)-N-methyl-2-[2-(2,5-dimethylphenoxymethyl) phenyl]-2-methoxy-aminoacetamide, 4-bromo-2-cyano-N, N-dimethyl-6-trifluoromethylbenzimidazole-1-sulphonamide, a-[N-(3-chloro-2,6-xylyl)-2-methoxyacetamido]-y-butyrolactone, 4-chloro-2-cyano-N,N-dimethyl-5-p-tolylimidazole-1-sulfonamide, N-allyl-4,5,-dimethyl-2-trimethylsilylthiophene-3-carboxamide, N-(l-cyano-1,2-dimethylpropyl)-2-(2,4-dichlorophenoxy) propionamide, N-(2-methoxy-5-pyridyl)-cyclopropane carboxamide, (.+−.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6(2-fluorophenoxy)pyrimidin-4-yloxy]phenyl]-3-methoxyacrylate, methyl (E)-2-[2-[3-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy) phenoxy]phenyl]-3-methoxyacrylate, methyl (E)-2-[2-phenoxyphenyl]-3-methoxyacrylate, methyl (E)-2-(2-(3,5-dimethyl-benzoyl)pyrrol-1-yl]-3-methoxyacrylate, methyl (E)-2-[2-(3-methoxyphenoxy)phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl-3-methoxyacrylate, methyl (E)-2-(2-(4-tort-butyl-pyridin-2-yloxy)phenyl]-3-methoxyacrylate, methyl (E)-2-[2-[3-(3-cyanophenoxy)phenoxy]phenyl]-3-ethoxyacrylate, methyl (E)-2-(2-[(3-methyl-pyridin-2-yloxymethyl)phenyl]-3-methoxyacrylate, methyl (E)-2-[2-[6-(2-methyl-phenoxy)pyrimidin-4-yloxy]phenyl]-3-methoxyacrylate, methyl (E)-2-[2-(5-bromopyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethyoximinomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{2-(3-methoxyphenyl) methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4 yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy] phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trlmethyl-oct3-en-5-ine), 2,6-dichloro-N-(4-trifluoromethylbenzyl)-benzamide, 3-iodo-2-propinyl alcohol, 4 chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribornophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2(5H)-furanone; 4,5-dichlorodithlazolinone, 4,5-benzodithlazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylmethyl)hexaminium chloride, acibenzolar, acypetacs, alanycarb, alendazole, aldimorph, ailicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscaild, bromnothalonil, bromnuconazole, bupirimnate, buthiobate, butylamine calcium polysulfide, captafol, captan, carbamorph, carbendazim, carbendazim chlorhydrate, carboxin, carpropamid, carvone, CGM41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymnoxanil, cypendazole, cyproconazole, cyprodinil, dazomet, debacarb, decafentin, dehydroacetic acid, di-2-pyridyl disulphide 1,1'-dioxide, dichlofluanid, didomezine, dichlone, dicloran, dichlorophen, dichlozoline, diclobutrazol, diclocymet, diethofencarb, difenoconazole, difenzoquat, diflumetorim, O, O-di-so-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N ([methyl (methyl-thioethylideneamino-oxycarbonyl) amino]thio)-ß-alaninate, etridiazole, famoxadone, fenamidone, fenaminosulf, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexa chlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, Iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mefentrifluconazole, mepanipyrim, mepronil, mercuric chloride, mercurous chloride, methyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-isopropyl, nuarimol, octhilinone, ofurace, organomercury compounds, orysastrobin, osthol, oxadixyl, oxasulfuron, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-AI, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, teraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolcofos-methyl, tolyfluanid, triadimefon, triadimenol, triamiphos, triarimol, triazbutil, triazoxide, tricyclazole, tridemorph, trifloxystrobin, triflumizole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552: Additional anthelmintic agents include the benzimidazoles such as albendazole, cambendazole, fenbendazole, flubendazole, mebendazole, oxfendazole, oxibendazole, parbendazole, and other members of the class. Additional antheknintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO 96/15121 and also with anthelmintic active cyclic depsipeptides such as those described in WO 96/11945, WO 93/19053, WO 93/25543, EP 0 626 375, EP 0 382 173, WO 94/19334, EP 0 382 173, and EP 0 503 538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO 95/19363 or WO 04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, dazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1 R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bloallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki*, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovedn, tulathromycin, ceftiour, carprofen, metaflumizone, praziquarantel, triclabendazole.

The following mixtures of the compounds of Formula (I) with active ingredients are preferred. The abbreviation "TX" means one compound selected from the group consisting of the compounds as represented in Tables 1.1 to 1.3 and Tables 2.1 and 2.2 (below), or the compounds 1.1 to 1.190 described in Table T1, (below):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfone (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, Isopropyl O-(methoxyaminothiophosphoryl)salicylate (IUPAC name) (473)+TX, ivermectin (alternative name) [CCN]+TX, jasmolin 1 (696)+TX, jasmolin 11 (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, mlibemycin oxime (alternative name) [CCN]+TX, mlpafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin 11 (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodicofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrine (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berdiner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla camea* (alternative name) (151)+TX, *Cryptolaemus montrouzier* (alternative name) (178)+TX, *Cydia pomonella* GV (alternative name) (191)+TX, *Dacnusa sibrica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisoplae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, *Bsubtilis* var. amyloliquefaciens Strain FZB24 (available from Novozymes Biologicals-Inc., 5400 Corporate Circle, Salem, Va. 24153, U.S.A. and known under the trade name Taegro®)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-cos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-den-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codiemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-cal (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate (CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, -chlordineform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin 1 (696)+TX, cinerin 11 (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephlon-O (1037)+TX, demephlon-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dlcrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathlon (1102)+TX, disulfoton (278)+TX, dithicrofos (1108)+

TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gama-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, Imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchoroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectdin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niciosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts—name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, Ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrfication inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, Iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of ametoctradin [865318-97-4]+TX, amisulbrom [348635-87-0]+TX, azaconazole [60207-31-0]+TX, benzovindiflupyr [1072957-71-1]+TX, bitertanol [70585-36-3]+TX, bixafen [581809-46-3]+TX, bromuconazole [116255-48-2]+TX, coumoxystrobin [850881-70-8]+TX, cyproconazole [94361-06-5]+TX, difenoconazole [119446-68-3]+TX, diniconazole [83657-24-3]+TX, enoxastrobin [238410-11-2]+TX, epoxiconazole [106325-08-0]+TX, fenbuconazole [11436943-6]+TX, fenpyrazamine [473798-59-3]+TX, fluquinconazole [136426-54-5]+TX, flusilazole [85509-19-9]+TX, flutriafol [76674-21-0]+TX, fluxapyroxad [907204-31-3]+TX, fluopyram [658066-35-4]+TX, fenaminstrobin [366815-39-6]+TX, isofetamid [875915-78-9]+TX, hexaconazole [79983-71-4]+TX, imazalil [3555444-0]+TX, imiben-conazole [86598-92-7]+TX, ipconazole [125225-28-7]+TX, ipfentrifluconazole [1417782-08-1]+TX, isotianil [224049-04-1]+TX, mandestrobin [173662-97-0] (can be prepared according to the procedures described in WO 2010/093059)+TX, mefentrifluconazole [1417782-03-6]+TX, metconazole [125116-23-6]+TX, myclobutanil [88671-89-0]+TX, paclobutrazol [76738-62-0]+TX, pefurazoate [101903-30-4]+TX, penflufen [494793-67-8]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [4312143-3]+TX, triadimenol [55219-65-3]+TX, triflumizole [99387-89-0]+TX, triticonazole [131983-72-7]+TX, ancymidol [12771-68-5]+TX, fenarimol. [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidin [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, fluindapyr [1383809-87-7]+TX, benalaxyl [71628-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, flutianil [958647-10-4]+TX, mepronil [55814-41-0]+TX, oxycarboxin [5259-88-1]+TX, penthiopyrad [183675-82-3]+TX, thiluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyradostrobin [175013-18-0]+TX, pyraoxystrobin [862588-11-2]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichloftluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxinecopper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, toldofos-methyl [57018-04-9]+TX, acibenzolar-S-methyl [135158-54-2]+TX, anilazine [101-05-3]+TX, benthlavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminum [39148-24-8]+TX, hymexazol [10004-44-1]+TX, iprovalicarb [140923-17-7]+

TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, picarbutrazox [500207-04-5]+TX, polyoxins [11113-80-7]+TX, probenazole [27605-76-1]+TX, propamocarb [25606-41-1]+TX, proquinazid [189278-12-4]+TX, pydiflumetofen [1228284-64-7]+TX, pyrametostrobin [915410-70-7]+TX, pyroquilon [57369-32-1]+TX, pyriofenone [688046-61-9]+TX, pyribencarb [799247-52-2]+TX, pyrisoxazole [847749-37-5]+TX, quinoxyfen [124495-18-7]+TX, quintozene [82-8-8]+TX, sulfur [7704-34-9]+TX, Timorex Gold™ (plant extract containing tea tree oil from the Stockton Group)+TX, tebufloquin [376645-78-2]+TX, tiadinil [223580-51-6]+TX, triazoxide [72459-58-6]+TX, tolprocarb [911499-62-2]+TX, triclopyricarb [902760-40-1]+TX, tricyclazole [41814-78-2]+TX, triforine [26644-46-2]+TX, validamycin [37248-47-8]+TX, valifenalate [283159-90-0]+TX, zoxamide (RH7281) [156052-68-5]+TX, mandipropamid [374726-62-2]+TX, isopyrazam [881685-58-1]+TX, phenamacril+TX, sedaxane [874967-67-6]+TX, trinexapao-ethyl [95266-40-3]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl]methy-cyclopropanecarboxylate [915972-17-7]+TX and 1,3,5-trimethyl-N-(2-methyl-1-oxopropyl)-N-[3-(2-methylpropyl)-4-2,2,2-trifluoro-1-methoxy-1-(trifluoromethyl)ethyl]phenyl-1H-pyrazole-4-carboxamide [926914-55-8]+TX, or a biologically active compound selected from the group consisting of N-((5-chloro-2-isopropyl-phenyl)methy-N-cyclopropyl-3-(difluoromethyl)-5-fluoro-1-methyl-pyrazole-4-carboxamide (can be prepared according to the procedures described in WO 2010/130767)+TX, 2,6-Dimethyl-1H,5H-[1,4]dithiino[2,3-c:5,6-c']dipyrrole-1,3,5,7(2H,6H)-tetrone (can be prepared according to the procedures described in WO 2011/138281)+TX, 6-ethyl-5,7-dioxo-pyrrolo[4,5][1,4]dithiino[1,2-c]isothiazole-3-carbonitrile+TX, 4-(2-bromo-4-fluoro-phenyl)-N-(2-chloro-6-fluoro-phenyl)-2,5-dimethyl-pyrazol-3-amine (can be prepared according to the procedures described in WO 2012/031061)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, CAS 850881-30-0+TX, 3-(3,4-dichloro-1,2-thiazol-5-yl-methoxy)-1,2-benzothiazole 1,1-dioxide (can be prepared according to the procedures described in WO 2007/129454)+TX, 2-[2-[(2,5-dimethylphenoxy)methyl]phenyl]-2-methoxy-N-methyl-acetamide+TX, 3-(4,4-difluoro-3,4-dihydro-3,3-dimethylisoquinoline-1-yl)quinolone (can be prepared according to the procedures described in WO 2005/070917)+TX, 2-[2-fluoro-6-[(8-fluoro-2-methyl-3-quinolyl)oxy]phenyl]propan-2-ol (can be prepared according to the procedures described in WO 2011/081174)+TX, 2-[2-[(7,8-difluoro-2-methyl-3-quinolyl)oxy]-6-fluoro-phenyl]propan-2-ol (can be prepared according to the procedures described in WO 2011/081174)+TX, oxathiapiprolin+TX [1003318-67-9], tert-butyl N-[6-[[[(1-methyletrazol-5-yl)-phenyl-methylene]amino]oxymethyl]-2-pyridyl]carbamate+TX, N-[2-(3,4-difluorophenyl)phenyl]-3-(trifluoromethyl)pyrazine-2-carboxamide (can be prepared according to the procedures described in WO 2007/072999)+TX, 3-(difluoromethyl)-1-methyl-N-[(3R)-1,1,3-trimethylindan-4-yl]pyrazole4-carboxamide (can be prepared according to the procedures described in WO 2014/013842)+TX, 2,2,2-trifluoroethyl N-[2-methyl-1-[[(4-methylbenzoyl)amino]methyl]propyl]carbamate+TX, (2RS)-2-[4-(4-chlorophenoxy)-α,α,α-trfluoro-o-tolyl]-1-(1H-1,2,4-triazol-1-yl)propan-2-ol+TX, (2RS)-2-[4-(4-chlorophenoxy)-α,α,α-trifluoro-o-tolyl]-3-methyl-1-(1H-1,2,4-triazol-1-yl)butan-2-ol+TX, 2-(difluoromethyl)-N-[(3R)-3-ethyl-1,1-dimethyl-indan-4-yl]pyridine-3-carboxamide+TX, 2-(difluoromethyl)-N-[3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine (can be prepared according to the procedures described in WO 2007/031513)+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate (can be prepared according to the procedures described in WO 2012/025557)+TX, but-3-ynyl N-[6-[[[(Z)-[(1-methyltetrazol-5-yl)-phenyl-methylene]amino]oxymethyl]-2-pyridyl] carbamate (can be prepared according to the procedures described in WO 2010/000841)+TX, 2-[[3-(2-chlorophenyl)-2-(2,4-difluorophenyl)oxiran-2-yl]methyl]-4H-1,2,4-triazole-3-thione (can be prepared according to the procedures described in WO 2010/146031)+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine (can be prepared according to the procedures described in WO 2005/121104)+TX, 2-[2-chloro-4-(4-chlorophenoxy)phenyl]-1-(1,2,4-triazol-1-yl)propan-2-ol (can be prepared according to the procedures described in WO 2013/024082)+TX, 3-chloro-4-(2,6-difluorophenyl)-6-methyl-5-phenyl-pyridazine (can be prepared according to the procedures described in WO 2012/020774)+TX, 4-(2,6-difluorophenyl)-6-methyl-5-phenyl-pyridazine-3-carbonitrile (can be prepared according to the procedures described in WO 2012/020774)+TX, (R)-3-(difluoromethyl)-1-methy-N-[1,1,3-trimethylindan-4-yl]pyrazole-4-carboxamide (can be prepared according to the procedures described in WO 2011/162397)+TX, 3-(difluoromethyl)-N-(7-fluoro-1,1,3-trimethyl-indan-4-yl)-1-methyl-pyrazole-4-carboxamide (can be prepared according to the procedures described in WO 2012/084812)+TX, 1-[2-[[1-(4-chlorophenyl)pyrazol-3-yl]oxymethyl]-3-methyl-phenyl]-4-methyl-tetrazol-5-one (can be prepared according to the procedures described in WO 2013/162072)+TX, 1-methyl-4-[3-methyl-2-[[2-methyl-4-(3,4,5-trimethylpyrazol-1-yl)phenoxy]methyl]phenyl]tetrazol-5-one (can be prepared according to the procedures described in WO 2014/051165)+TX, (Z,2E)-5-[1-(4-chlorophenyl)pyrazol-3-yl]oxy-2-methoxyimino-N,3-dimethyl-pent-3-enamide+TX, (4-phenoxyphenyl)methyl 2-amino-6-methyl-pyridine-3-carboxylate+TX, N-(5-chloro-2-isopropylbenzyl)-N-cyclopropyl-3-(difluoromethyl)-5-fluoro-1-methylpyrazole-4-carboxamide [1255734-28-1] (can be prepared according to the procedures described in WO 2010/130767)+TX, 3-(difluoromethyl)-N—[(R)-2,3-dihydro-1,1,3-trimethyl-1H-inden-4-yl]-1-methylpyrazole-4-carboxamide [1352994-67-2]+TX, N'-(2,5-dimethyl-4-phenoxy-phenyl)-N-ethyl-N-methyl-formamidine+TX, N'-[4-(4,5-dichloro-thiazol-2-yloxy)-2,5-dimethyl-phenyl]-N-ethyl-N-methyl-formamidine+TX, N'-(2,5-dimethyl-4-phenoxy-phenyl)-N-ethyl-N-methyl-formamidine+TX, N'-

[4-(4,5-dichloro-thiazol-2-yloxy)-2,5-dimethyl-phenyl]-N-ethyl-N-methyl-formamidine+TX,

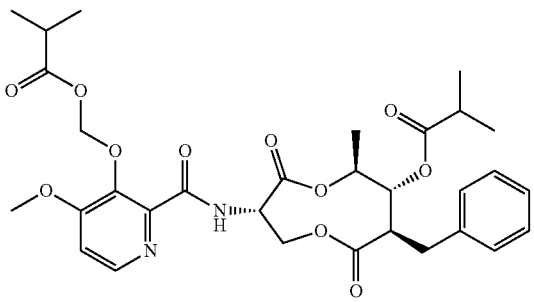 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

(fenpicoxamid [517875-34-2] (as described in WO 2003/035617))+TX, (1S)-2,2-bis(4-fluorophenyl)-1-methylethyl N-{[3-(acetyloxy)-4-methoxy-2-pyridyl]carbonyl}-L-alaninate [1961312-55-9] (as described in WO 2016/122802)+TX, 2-(difluoromethyl)-N-(1,1,3-trimethylindan-4-yl)pyridine-3-carboxamide+TX, 2-(difluoromethyl)-N-(3-ethyl-1,1-dimethyl-indan-4-yl)pyridine-3-carboxamide+TX, 2-(difluoromethyl)-N-(1,1-dimethyl-3-propyl-indan-4-yl)pyridine-3-carboxamide+TX, 2-(difluoromethyl)-N-(3-isobutyl-1,1-dimethyl-indan-4-yl)pyridine-3-carboxamide+TX, 2-(difluoromethyl)-N-[(3R)-1,1,3-trimethylindan-4-yl]pyridine-3-carboxamide+TX, 2-(difluoromethyl)-N-[(3R)-3-ethyl-1,1-dimethylindan-4-yl]pyridine-3-carboxamide+TX, and 2-(difluoromethyl)-N-[(3R)-1,1-dimethyl-3-propyl-indan-4-yl]pyridine-3-carboxamide+TX, wherein each of these carboxamide compounds can be prepared according to the procedures described in WO 2014/095675 and/or WO 2016/139189.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the Internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula (I) selected from one compound as represented in Tables 1.1 to 1.3 and Tables 2.1 and 2.2 (below), or the compounds 1.1 to 1.190 described in Table T1 (below), is preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound as represented in Tables 1.1 to 1.3 and Tables 2.1 and 2.2 (below), or the compounds 1.1 to 1.190 described in Table T1 (below), and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying a compound as represented in in Tables 1.1 to 1.3 and Tales 2.1 and 2.2 (below), or the compounds 1.1 to 1.190 described in Table T1 (below), and the active ingredient(s) as described above, is not essential for working the present invention.

The compositions according to the invention can also comprise further solid or liquid auxiliaries, such as stabilizers, for example unepoxidized or epoxidized vegetable oils (for example epoxidized coconut ol, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds (I) for the preparation of these compositions are also a subject of the invention.

Another aspect of the invention is related to the use of a compound of Formula (I) or of a preferred individual compound as defined herein, of a composition comprising at least one compound of Formula (I) or at least one preferred individual compound as above-defined, or of a fungicidal or insecticidal mixture comprising at least one compound of Formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of the invention is related to a method of controlling or preventing an infestation of plants, e.g., useful plants such as crop plants, propagation material thereof, e.g. seeds, harvested crops, e.g., harvested food crops, or of non-living materials by insects or by phytopathogenic or spoilage microorganisms or organisms potentially harmful to man, especially fungal organisms, which comprises the application of a compound of Formula (I) or of a preferred individual compound as above-defined as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of Formula (I), or an agrochemical composition which contains at least one of said compounds, is foliar application. The frequency of application and the rate of application will depend on the risk of infestation by the corresponding pathogen or insect. However, the compounds of Formula (I) can also penetrate the plant through the roots via the soil (systemic action) by drenching the locus of the plant with a liquid Formulation, or by applying the compounds in solid form to the soil, e.g. in granular form (soil application). In crops of water rice such granulates can be applied to the flooded rice field. The compounds of Formula (I) may also be applied to seeds (coating) by impregnating the seeds or tubers either with a liquid formulation of the fungicide or coating them with a solid formulation.

A formulation, e.g. a composition containing the compound of Formula (I), and, if desired, a solid or liquid adjuvant or monomers for encapsulating the compound of Formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i/ha. When used as seed drenching agent, convenient dosages are from 10 mg to 1 g of active substance per kg of seeds.

When the combinations of the present invention are used for treating seed, rates of 0.001 to 50 g of a compound of Formula (I) per kg of seed, preferably from 0.01 to 10 g per kg of seed are generally sufficient.

Suitably, a composition comprising a compound of Formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly, formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or, microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of Formula (I) optionally together with other active agents, particularly microbiocides or conservatives or the like. Concentrated forms of compositions generally contain in between about 2 and 80%, preferably between about 5 and 70% by weight of active agent Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

TABLE 1.1

This table discloses 65 specific compounds of the formula (T-1):

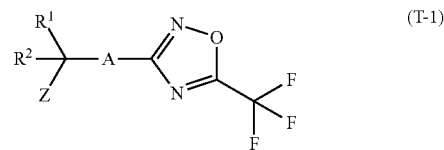

wherein A is 2,5-thienyl and $R^1$ and $R^2$, are hydrogen, and Z is as defined below in the Table 1.

Each of Tables 1.2 to 1.3 (which follow Table 1.1) make available 65 individual compounds of the formula (T-1) in which A, $R^1$, and $R^2$ are as specifically defined in Tables 1.2 to 1.3, which refer to Table 1 wherein Z is specifically defined.

TABLE 1

| Compound no. | Z |
|---|---|
| 1.001 | 1H-pyrazole-4-carboxylic acid |
| 1.002 | methyl 1H-pyrazole-4-carboxylate |
| 1.003 | ethyl 1H-pyrazole-4-carboxylate |
| 1.004 | propyl 1H-pyrazole-4-carboxylate |
| 1.005 | prop-2-enyl 1H-pyrazole-4-carboxylate |
| 1.006 | prop-2-ynyl 1H-pyrazole-4-carboxylate |
| 1.007 | tert-butyl 1H-pyrazole-4-carboxylate |
| 1.008 | isopropyl 1H-pyrazole-4-carboxylate |
| 1.009 | 2-(dimethylamino)ethyl 1H-pyrazole-4-carboxylate |
| 1.010 | 2-methoxyethyl 1H-pyrazole-4-carboxylate |
| 1.011 | cyclopropyl 1H-pyrazole-4-carboxylate |
| 1.012 | cyclopropylmethyl 1H-pyrazole-4-carboxylate |
| 1.013 | 1H-pyrazole-4-carboxamide |
| 1.014 | N-methyl-1H-pyrazole-4-carboxamide |
| 1.015 | N-ethyl-1H-pyrazole-4-carboxamide |
| 1.016 | N-propyl-1H-pyrazole-4-carboxamide |
| 1.017 | N-isopropyl-1H-pyrazole-4-carboxamide |
| 1.018 | N-prop-2-enyl-1H-pyrazole-4-carboxamide |
| 1.019 | N-prop-2-ynyl-1H-pyrazole-4-carboxamide |
| 1.020 | N-cyclopropyl-1H-pyrazole-4-carboxamide |
| 1.021 | N-(cyclopropylmethyl)-1H-pyrazole-4-carboxamide |
| 1.022 | N-(2-methoxyethyl)-1H-pyrazole-4-carboxamide |
| 1.023 | N-methoxy-1H-pyrazole-4-carboxamide |
| 1.024 | N-ethoxy-1H-pyrazole-4-carboxamide |
| 1.025 | N-prop-2-enyloxy-1H-pyrazole-4-carboxamide |
| 1.026 | N-methoxy-N-methyl-1H-pyrazole-4-carboxamide |
| 1.027 | N-ethoxy-N-methyl-1H-pyrazole-4-carboxamide |
| 1.028 | N,N-dimethyl-1H-pyrazole-4-carboxamide |
| 1.029 | N,N-diethyl-1H-pyrazole-4-carboxamide |
| 1.030 | N-ethyl-N-methyl-1H-pyrazole-4-carboxamide |
| 1.031 | N-prop-2-enyl-N-methyl-1H-pyrazole-4-carboxamide |
| 1.032 | imidazol-1-yl |
| 1.033 | 5-methyl-3-aminopyrazol-2-yl |
| 1.034 | 4-fluoropyrazol-1-yl |
| 1.035 | 1H-pyrazole-4-carbonitrile |
| 1.036 | 5-(2-bromophenyl)tetrazol-1-yl |
| 1.037 | 4-nitropyrazol-1-yl |
| 1.038 | pyrrolo[2,3-b]pyridin-1-yl |
| 1.039 | pyrazol-1-yl |
| 1.040 | methyl 1H-1,2,4-triazole-3-carboxylate |
| 1.041 | 4-methylpyrazol-1-yl |
| 1.042 | 1,2,3-triazol-1-yl |
| 1.043 | 1,2,4-triazol-1-yl |
| 1.044 | 5,5-dimethyl-isoxazolidin-3-one |
| 1.045 | N,N-dimethyl-1H-1,2,4-triazol-3-amine |
| 1.046 | benzimidazol-1-yl |
| 1.047 | 5-methoxybenzimidazol-1-yl |
| 1.048 | 6-methoxybenzimidazol-1-yl |
| 1.049 | 1H-pyrazole-4-carbaldehyde |
| 1.050 | 3,5-dimethylpyrazol-1-yl |
| 1.051 | azetidin-1-yl |
| 1.052 | methyl 3-(methoxymethyl)-1H-pyrazole-4-carboxylate |
| 1.053 | 5-(difluoromethyl)-3-amino-1,2,4-triazol-2-yl |
| 1.054 | 1-piperidyl |
| 1.055 | morpholin-4-yl |
| 1.056 | 3-oxo-morpholin-4-yl |
| 1.057 | 3-oxo-isoxazolidin-2-yl |
| 1.058 | 5,5-dimethyl-3-oxo-isoxazolidin-2-yl |
| 1.059 | 2-oxo-1-piperidyl |
| 1.060 | 3, 3-dimethyl-2-oxo-1-piperidyl |
| 1.061 | 4,4-dimethyl-3-oxo-isoxazolidin-2-yl |
| 1.062 | 4-methyl-2-oxo-1-pyridyl |
| 1.063 | 2-oxo-1-pyridyl |
| 1.064 | 1,1-dioxo-1,2-thiazolidin-2-yl |
| 1.065 | 2-oxopyrroridin-1-yl |

Table 1.2:

This table discloses 65 specific compounds of formula (T-1) wherein A is 3,5-thienyl and $R^1$ and $R^2$ are hydrogen, Z is as defined above in Table 1.

Table 1.3:

This table discloses 65 specific compounds of formula (T-1) wherein A is 2,5-thienyl and $R^1$ is hydrogen, $R^2$ is methyl, and Z is as defined above in Table 1.

TABLE 2.1

This table discloses 372 specific compounds of the formula (T-2):

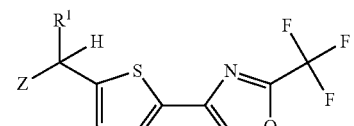

wherein $R^1$ is hydrogen and Z is as defined below in Table 2.

Table 2.2 (which follows Table 2.1) makes available 372 Individual compounds of the formula (T-2) in which $R^1$ is as specifically defined in Table 2.2, which refers to Table 2 wherein Z is specifically defined.

TABLE 2

| Compound no. | Z |
|---|---|
| 2.001 | 2H-pyrazole-3-carboxylic acid |
| 2.002 | methyl 2H-pyrazole-3-carboxylate |
| 2.003 | ethyl 2H-pyrazole-3-carboxylate |
| 2.004 | propyl 2H-pyrazole-3-carboxylate |
| 2.005 | prop-2-enyl 2H-pyrazole-3-carboxylate |
| 2.006 | prop-2-ynyl 2H-pyrazole-3-carboxylate |
| 2.007 | tert-butyl 2H-pyrazole-3-carboxylate |
| 2.008 | isopropyl 2H-pyrazole-3-carboxylate |
| 2.009 | 2-(dimethylamino)ethyl 2H-pyrazole-3-carboxylate |
| 2.010 | 2-methoxyethyl 2H-pyrazole-3-carboxylate |
| 2.011 | cyclopropyl 2H-pyrazole-3-carboxylate |

TABLE 2-continued

| Compound no. | Z |
|---|---|
| 2.012 | cyclopropylmethyl 2H-pyrazole-3-carboxylate |
| 2.013 | 2H-pyrazole-3-carboxamide |
| 2.014 | N-methyl-2H-pyrazole-3-carboxamide |
| 2.015 | N-ethyl-2H-pyrazole-3-carboxamide |
| 2.016 | N-propyl-2H-pyrazole-3-carboxamide |
| 2.017 | N-isopropyl-2H-pyrazole-3-carboxamide |
| 2.018 | N-prop-2-enyl-2H-pyrazole-3-carboxamide |
| 2.019 | N-prop-2-ynyl-2H-pyrazole-3-carboxamide |
| 2.020 | N-cyclopropyl-2H-pyrazole-3-carboxamide |
| 2.021 | N-(cyclopropylmethyl)-2H-pyrazole-3-carboxamide |
| 2.022 | N-(2-methoxyethyl)-2H-pyrazole-3-carboxamide |
| 2.023 | N-methoxy-2H-pyrazole-3-carboxamide |
| 2.024 | N-ethoxy-2H-pyrazole-3-carboxamide |
| 2.025 | N-prop-2-enyloxy-2H-pyrazole-3-carboxamide |
| 2.026 | N-methoxy-N-methyl-2H-pyrazole-3-carboxamide |
| 2.027 | N-ethoxy-N-methyl-2H-pyrazole-3-carboxamide |
| 2.028 | N,N-dimethyl-2H-pyrazole-3-carboxamide |
| 2.029 | N,N-diethyl-2H-pyrazole-3-carboxamide |
| 2.030 | N-ethyl-N-methyl-2H-pyrazole-3-carboxamide |
| 2.031 | N-prop-2-enyl-N-methyl-2H-pyrazole-3-carboxamide |
| 2.032 | 1H-pyrazole-3-carboxylic acid |
| 2.033 | methyl 1H-pyrazole-3-carboxylate |
| 2.034 | ethyl 1H-pyrazole-3-carboxylate |
| 2.035 | propyl 1H-pyrazole-3-carboxylate |
| 2.036 | prop-2-enyl 1H-pyrazole-3-carboxylate |
| 2.037 | prop-2-ynyl 1H-pyrazole-3-carboxylate |
| 2.038 | tert-butyl 1H-pyrazole-3-carboxylate |
| 2.039 | isopropyl 1H-pyrazole-3-carboxylate |
| 2.040 | 2-(dimethylamino)ethyl 1H-pyrazole-3-carboxylate |
| 2.041 | 2-methoxyethyl 1H-pyrazole-3-carboxylate |
| 2.042 | cyclopropyl 1H-pyrazole-3-carboxylate |
| 2.043 | cyclopropylmethyl 1H-pyrazole-3-carboxylate |
| 2.044 | 1H-pyrazole-3-carboxamide |
| 2.045 | N-methyl-1H-pyrazole-3-carboxamide |
| 2.046 | N-ethyl-1H-pyrazole-3-carboxamide |
| 2.047 | N-propyl-1H-pyrazole-3-carboxamide |
| 2.048 | N-isopropyl-1H-pyrazole-3-carboxamide |
| 2.049 | N-prop-2-enyl-1H-pyrazole-3-carboxamide |
| 2.050 | N-prop-2-ynyl-1H-pyrazole-3-carboxamide |
| 2.051 | N-cyclopropyl-1H-pyrazole-3-carboxamide |
| 2.052 | N-(cyclopropylmethyl)-1H-pyrazole-3-carboxamide |
| 2.053 | N-(2-methoxyethyl)-1H-pyrazole-3-carboxamide |
| 2.054 | N-methoxy-1H-pyrazole-3-carboxamide |
| 2.055 | N-ethoxy-1H-pyrazole-3-carboxamide |
| 2.056 | N-prop-2-enyloxy-1H-pyrazole-3-carboxamide |
| 2.057 | N-methoxy-N-methyl-1H-pyrazole-3-carboxamide |
| 2.058 | N-ethoxy-N-methyl-1H-pyrazole-3-carboxamide |
| 2.059 | N,N-dimethyl-1H-pyrazole-3-carboxamide |
| 2.060 | N,N-diethyl-1H-pyrazole-3-carboxamide |
| 2.061 | N-ethyl-N-methyl-1H-pyrazole-3-carboxamide |
| 2.062 | N-prop-2-enyl-N-methyl-1H-pyrazole-3-carboxamide |
| 2.063 | 1H-imidazole-2-carboxylic acid |
| 2.064 | methyl 1H-imidazole-2-carboxylate |
| 2.065 | ethyl 1H-imidazole-2-carboxylate |
| 2.066 | propyl 1H-imidazole-2-carboxylate |
| 2.067 | prop-2-enyl 1H-imidazole-2-carboxylate |
| 2.068 | prop-2-ynyl 1H-imidazole-2-carboxylate |
| 2.069 | tert-butyl 1H-imidazole-2-carboxylate |
| 2.070 | isopropyl 1H-imidazole-2-carboxylate |
| 2.071 | 2-(dimethylamino)ethyl 1H-imidazole-2-carboxylate |
| 2.072 | 2-methoxyethyl 1H-imidazole-2-carboxylate |
| 2.073 | cyclopropyl 1H-imidazole-2-carboxylate |
| 2.074 | cyclopropylmethyl 1H-imidazole-2-carboxylate |
| 2.075 | 1H-imidazole-2-carboxamide |
| 2.076 | N-methyl-1H-imidazole-2-carboxamide |
| 2.077 | N-ethyl-1H-imidazole-2-carboxamide |
| 2.078 | N-propyl-1H-imidazole-2-carboxamide |
| 2.079 | N-isopropyl-1H-imidazole-2-carboxamide |
| 2.080 | N-prop-2-enyl-1H-imidazole-2-carboxamide |
| 2.081 | N-prop-2-ynyl-1H-imidazole-2-carboxamide |
| 2.082 | N-cyclopropyl-1H-imidazole-2-carboxamide |
| 2.083 | N-(cyclopropylmethyl)-1H-imidazole-2-carboxamide |
| 2.084 | N-(2-methoxyethyl)-1H-imidazole-2-carboxamide |
| 2.085 | N-methoxy-1H-imidazole-2-carboxamide |
| 2.086 | N-ethoxy-1H-imidazole-2-carboxamide |
| 2.087 | N-prop-2-enyloxy-1H-imidazole-2-carboxamide |
| 2.088 | N-methoxy-N-methyl-1H-imidazole-2-carboxamide |
| 2.089 | N-ethoxy-N-methyl-1H-imidazole-2-carboxamide |
| 2.090 | N,N-dimethyl-1H-imidazole-2-carboxamide |
| 2.091 | N,N-diethyl-1H-imidazole-2-carboxamide |
| 2.092 | N-ethyl-N-methyl-1H-imidazole-2-carboxamide |
| 2.093 | N-prop-2-enyl-N-methyl-1H-imidazole-2-carboxamide |
| 2.094 | 1H-imidazole-4-carboxylic acid |

TABLE 2-continued

| Compound no. | Z |
|---|---|
| 2.095 | methyl 1H-imidazole-4-carboxylate |
| 2.096 | ethyl 1H-imidazole-4-carboxylate |
| 2.097 | propyl 1H-imidazole-4-carboxylate |
| 2.098 | prop-2-enyl 1H-imidazole-4-carboxylate |
| 2.099 | prop-2-ynyl 1H-imidazole-4-carboxylate |
| 2.100 | tert-butyl 1H-imidazole-4-carboxylate |
| 2.101 | isopropyl 1H-imidazole-4-carboxylate |
| 2.102 | 2-(dimethylamino)ethyl 1H-imidazole-4-carboxylate |
| 2.103 | 2-methoxyethyl 1H-imidazole-4-carboxylate |
| 2.104 | cyclopropyl 1H-imidazole-4-carboxylate |
| 2.105 | cyclopropylmethyl 1H-imidazole-4-carboxylate |
| 2.106 | 1H-imidazole-4-carboxamide |
| 2.107 | N-methyl-1H-imidazole-4-carboxamide |
| 2.108 | N-ethyl-1H-imidazole-4-carboxamide |
| 2.109 | N-propyl-1H-imidazole-4-carboxamide |
| 2.110 | N-isopropyl-1H-imidazole-4-carboxamide |
| 2.111 | N-prop-2-enyl-1H-imidazole-4-carboxamide |
| 2.112 | N-prop-2-ynyl-1H-imidazole-4-carboxamide |
| 2.113 | N-cyclopropyl-1H-imidazole-4-carboxamide |
| 2.114 | N-(cyclopropylmethyl)-1H-imidazole-4-carboxamide |
| 2.115 | N-(2-methoxyethyl)-1H-imidazole-4-carboxamide |
| 2.116 | N-methoxy-1H-imidazole-4-carboxamide |
| 2.117 | N-ethoxy-1H-imidazole-4-carboxamide |
| 2.118 | N-prop-2-enyloxy-1H-imidazole-4-carboxamide |
| 2.119 | N-methoxy-N-methyl-1H-imidazole-4-carboxamide |
| 2.120 | N-ethoxy-N-methyl-1H-imidazole-4-carboxamide |
| 2.121 | N,N-dimethyl-1H-imidazole-4-carboxamide |
| 2.122 | N,N-diethyl-1H-imidazole-4-carboxamide |
| 2.123 | N-ethyl-N-methyl-1H-imidazole-4-carboxamide |
| 2.124 | N-prop-2-enyl-N-methyl-1H-imidazole-4-carboxamide |
| 2.125 | 3H-imidazole-4-carboxylic acid |
| 2.126 | methyl 3H-imidazole-4-carboxylate |
| 2.127 | ethyl 3H-imidazole-4-carboxylate |
| 2.128 | propyl 3H-imidazole-4-carboxylate |
| 2.129 | prop-2-enyl 3H-imidazole-4-carboxylate |
| 2.130 | prop-2-ynyl 3H-imidazole-4-carboxylate |
| 2.131 | tert-butyl 3H-imidazole-4-carboxylate |
| 2.132 | isopropyl 3H-imidazole-4-carboxylate |
| 2.133 | 2-(dimethylamino)ethyl 3H-imidazole-4-carboxylate |
| 2.134 | 2-methoxyethyl 3H-imidazole-4-carboxylate |
| 2.135 | cyclopropyl 3H-imidazole-4-carboxylate |
| 2.136 | cyclopropylmethyl 3H-imidazole-4-carboxylate |
| 2.137 | 3H-imidazole-4-carboxamide |
| 2.138 | N-methyl-3H-imidazole-4-carboxamide |
| 2.139 | N-ethyl-3H-imidazole-4-carboxamide |
| 2.140 | N-propyl-3H-imidazole-4-carboxamide |
| 2.141 | N-isopropyl-3H-imidazole-4-carboxamide |
| 2.142 | N-prop-2-enyl-3H-imidazole-4-carboxamide |
| 2.143 | N-prop-2-ynyl-3H-imidazole-4-carboxamide |
| 2.144 | N-cyclopropyl-3H-imidazole-4-carboxamide |
| 2.145 | N-(cyclopropylmethyl)-3H-imidazole-4-carboxamide |
| 2.146 | N-(2-methoxyethyl)-3H-imidazole-4-carboxamide |
| 2.147 | N-methoxy-3H-imidazole-4-carboxamide |
| 2.148 | N-ethoxy-3H-imidazole-4-carboxamide |
| 2.149 | N-prop-2-enyloxy-3H-imidazole-4-carboxamide |
| 2.150 | N-methoxy-N-methyl-3H-imidazole-4-carboxamide |
| 2.151 | N-ethoxy-N-methyl-3H-imidazole-4-carboxamide |
| 2.152 | N,N-dimethyl-3H-imidazole-4-carboxamide |
| 2.153 | N,N-diethyl-3H-imidazole-4-carboxamide |
| 2.154 | N-ethyl-N-methyl-3H-imidazole-4-carboxamide |
| 2.155 | N-prop-2-enyl-N-methyl-3H-imidazole-4-carboxamide |
| 2.156 | 2H-1,2,4-triazole-3-carboxylic acid |
| 2.157 | methyl 2H-1,2,4-triazole-3-carboxylate |
| 2.158 | ethyl 2H-1,2,4-triazole-3-carboxylate |
| 2.159 | propyl 2H-1,2,4-triazole-3-carboxylate |
| 2.160 | prop-2-enyl 2H-1,2,4-triazole-3-carboxylate- |
| 2.161 | prop-2-ynyl 21-1-1,2,4-triazole-3-carboxylate |
| 2.162 | tert-butyl 2H-1,2,4-triazole-3-carboxylate |
| 2.163 | isopropyl 2H-1,2,4-triazole-3-carboxylate |
| 2.164 | 2-(dimethylamino)ethyl 2H-1,2,4-triazole-3-carboxylate |
| 2.165 | 2-methoxyethyl 2H-1,2,4-triazole-3-carboxylate |
| 2.166 | cyclopropyl 2H-1,2,4-triazole-3-carboxylate |
| 2.167 | cyclopropylmethyl 2H-1,2,4-triazole-3-carboxylate |
| 2.168 | 2H-1,2,4-triazole-3-carboxamide |
| 2.169 | N-methyl-2H-1,2,4-triazole-3-carboxamide |
| 2.170 | N-ethyl-2H-1,2,4-triazole-3-carboxamide |
| 2.171 | N-propyl-2H-1,2,4-triazole-3-carboxamide |
| 2.172 | N-isopropyl-2H-1,2,4-triazole-3-carboxamide |
| 2.173 | N-prop-2-enyl-2H-1,2,4-triazole-3-carboxamide |
| 2.174 | N-prop-2-ynyl-2H-1,2,4-triazole-3-carboxamide |
| 2.175 | N-cyclopropyl-2H-1,2,4-triazole-3-carboxamide |
| 2.176 | N-(cyclopropylmethyl)-2H-1,2,4-triazole-3-carboxamide |

TABLE 2-continued

| Compound no. | Z |
|---|---|
| 2.177 | N-(2-methoxyethyl)-2H-1,2,4-triazole-3-carboxamide |
| 2.178 | N-methoxy-2H-1,2,4-triazole-3-carboxamide |
| 2.179 | N-ethoxy-2H-1,2,4-triazole-3-carboxamide |
| 2.180 | N-prop-2-enyloxy-2H-1,2,4-triazole-3-carboxamide |
| 2.181 | N-methoxy-N-methyl-2H-1,2,4-triazole-3-carboxamide |
| 2.182 | N-ethoxy-N-methyl-2H-1,2,4-triazole-3-carboxamide |
| 2.183 | N,N-dimethyl-2H-1,2,4-triazole-3-carboxamide |
| 2.184 | N,N-diethyl-2H-1,2,4-triazole-3-carboxamide |
| 2.185 | N-ethyl-N-methyl-2H-1,2,4-triazole-3-carboxamide |
| 2.186 | N-prop-2-enyl-N-methyl-2H-1,2,4-triazole-3-carboxamide |
| 2.187 | 1H-1,2,4-triazole-3,carboxylic acid |
| 2.188 | methyl 1H-1,2,4-triazole-3-carboxylate |
| 2.189 | ethyl 1H-1,2,4-triazole-3-carboxylate |
| 2.190 | propyl 1H-1,2,4-triazole-3-carboxylate |
| 2.191 | prop-2-enyl 1H-1,2,4-triazole-3-carboxylate |
| 2.192 | prop-2-ynyl 1H-1,2,4-triazole-3-carboxylate |
| 2.193 | tert-butyl 1H-1,2,4-triazole-3-carboxylate |
| 2.194 | isopropyl 1H-1,2,4-triazole-3-carboxylate |
| 2.195 | 2-(dimethylamino)ethyl 1H-1,2,4-triazole-3-carboxylate |
| 2.196 | 2-methoxyethyl 1H-1,2,4-triazole-3-carboxylate |
| 2.197 | cyclopropyl 1H-1,2,4-triazole-3-carboxylate |
| 2.198 | cyclopropylmethyl 1H-1,2,4-triazole-3-carboxylate |
| 2.199 | 1H-1,2,4-triazole-3-carboxamide |
| 2.200 | N-methyl-1H-1,2,4-triazole-3-carboxamide |
| 2.201 | N-ethyl-1H-1,2,4-triazole-3-carboxamide |
| 2.202 | N-propyl-1H-1,2,4-triazole-3-carboxamide |
| 2.203 | N-isopropyl-1H-1,2,4-triazole-3-carboxamide |
| 2.204 | N-prop-2-enyl-1H-1,2,4-triazole-3-carboxamide |
| 2.205 | N-prop-2-ynyl-1H-1,2,4-triazole-3-carboxamide |
| 2.206 | N-cyclopropyl-1H-1,2,4-triazole-3-carboxamide |
| 2.207 | N-(cyclopropylmethyl)-1H-1,2,4-triazole-3-carboxamide |
| 2.208 | N-(2-methoxyethyl)-1H-1,2,4-triazole-3-carboxamide |
| 2.209 | N-methoxy-1H-1,2,4-triazole-3-carboxamide |
| 2.210 | N-ethoxy-1H-1,2,4-triazole-3-carboxamide |
| 2.211 | N-prop-2-enyloxy-1H-1,2,4-triazole-3-carboxamide |
| 2.212 | N-methoxy-N-methyl-1H-1,2,4-triazole-3-carboxamide |
| 2.213 | N-ethoxy-N-methyl-1H-1,2,4-triazole-3-carboxamide |
| 2.214 | N,N-dimethyl-1H-1,2,4-triazole-3-carboxamide |
| 2.215 | N,N-diethyl-1H-1,2,4-triazole-3-carboxamide |
| 2.216 | N-ethyl-N-methyl-1H-1,2,4-triazole-3-carboxamide |
| 2.217 | N-prop-2-enyl-N-methyl-1H-1,2,4-triazole-3-carboxamide |
| 2.218 | 3H-triazole-4-carboxylic acid |
| 2.219 | methyl 3H-triazole-4-carboxylate |
| 2.220 | ethyl 3H-triazole-4-carboxylate |
| 2.221 | propyl 3H-triazole-4-carboxylate |
| 2.222 | prop-2-enyl 3H-triazole-4-carboxylate |
| 2.223 | prop-2-ynyl 3H-triazole-4-carboxylate |
| 2.224 | tert-butyl 3H-triazole-4-carboxylate |
| 2.225 | isopropyl 3H-triazole-4-carboxylate |
| 2.226 | 2-(dimethylamino)ethyl 3H-triazole-4-carboxylate |
| 2.227 | 2-methoxyethyl 3H-triazole-4-carboxylate |
| 2.228 | cyclopropyl 3H-triazole-4-carboxylate |
| 2.229 | cyclopropylmethyl 3H-triazole-4-carboxylate |
| 2.230 | 3H-triazole-4-carboxamide |
| 2.231 | N-methyl-3H-triazole-4-carboxamide |
| 2.232 | N-ethyl-3H-triazole-4-carboxamide |
| 2.233 | N-propyl-3H-triazole-4-carboxamide |
| 2.234 | N-isopropyl-3H-triazole-4-carboxamide |
| 2.235 | N-prop-2-enyl-3H-triazole-4-carboxamide |
| 2.236 | N-prop-2-ynyl-3H-triazole-4-carboxamide |
| 2.237 | N-cyclopropyl-3H-triazole-4-carboxamide |
| 2.238 | N-(cyclopropylmethyl)-3H-triazole-4-carboxamide |
| 2.239 | N-(2-methoxyethyl)-3H-triazole-4-carboxamide |
| 2.240 | N-methoxy-3H-triazole-4-carboxamide |
| 2.241 | N-ethoxy-3H-triazole-4-carboxamide |
| 2.242 | N-prop-2-enyloxy-3H-triazole-4-carboxamide |
| 2.243 | N-methoxy-N-methyl-3H-triazole-4-carboxamide |
| 2.244 | N-ethoxy-N-methyl-3H-triazole-4-carboxamide |
| 2.245 | N,N-dimethyl-3H-triazole-4-carboxamide |
| 2.246 | N,N-diethyl-3H-triazole-4-carboxamide |
| 2.247 | N-ethyl-N-methyl-3H-triazole-4-carboxamide |
| 2.248 | N-prop-2-enyl-N-methyl-3H-triazole-4-carboxamide |
| 2.249 | 2H-triazole-4-carboxylic acid |
| 2.250 | methyl 2H-triazole-4-carboxylate |
| 2.251 | ethyl 2H-triazole-4-carboxylate |
| 2.252 | propyl 2H-triazole-4-carboxylate |
| 2253 | prop-2-enyl 2H-triazole-4-carboxylate |
| 2.254 | prop-2-ynyl 2H-triazole-4-carboxylate |
| 2.255 | tert-butyl 2H-triazole-4-carboxylate |
| 2.256 | isopropyl 2H-triazole-4-carboxylate |
| 2.257 | 2-(dimethylamino)ethyl 2H-triazole-4-carboxylate |
| 2.258 | 2-methoxyethyl 2H-triazole-4-carboxylate |
| 2.259 | cyclopropyl 2H-triazole-4-carboxylate |
| 2.260 | cyclopropylmethyl 2H-triazole-4-carboxylate |
| 2.261 | 2H-triazole-4-carboxamide |

TABLE 2-continued

| Compound no. | Z |
|---|---|
| 2.262 | N-methyl-2H-triazole-4-carboxamide |
| 2.263 | N-ethyl-2H-triazole-4-carboxamide |
| 2.264 | N-propyl-2H-triazole-4-carboxamide |
| 2.265 | N-isopropyl-2H-triazole-4-carboxamide |
| 2.266 | N-prop-2-enyl-2H-triazole-4-carboxamide |
| 2.267 | N-prop-2-ynyl-2H-triazole-4-carboxamide |
| 2.268 | N-cyclopropyl-2H-triazole-4-carboxamide |
| 2.269 | N-(cyclopropylmethyl)-2H-triazole-4-carboxamide |
| 2.270 | N-(2-methoxyethyl)-2H-triazole-4-carboxamide |
| 2.271 | N-methoxy-2H-triazole-4-carboxamide |
| 2.272 | N-ethoxy-2H-triazole-4-carboxamide |
| 2.273 | N-prop-2-enyloxy-2H-triazole-4-carboxamide |
| 2.274 | N-methoxy-N-methyl-2H-triazole-4-carboxamide |
| 2.275 | N-ethoxy-N-methyl-2H-triazole-4-carboxamide |
| 2.276 | N,N-dimethyl-2H-triazole-4-carboxamide |
| 2.277 | N, N-diethyl-2H-triazole-4-carboxamide |
| 2.278 | N-ethyl-N-methyl-2H-triazole-4-carboxamide |
| 2.279 | N-prop-2-enyl-N-methyl-2H-triazole-4-carboxamide |
| 2.280 | 1H-triazole-4-carboxylic acid |
| 2.281 | methyl 1H-triazole-4-carboxylate |
| 2.282 | ethyl 1H-triazole-4-carboxylate |
| 2.283 | propyl 1H-triazole-4-carboxylate |
| 2.284 | prop-2-enyl 1H-triazole-4-carboxylate |
| 2.285 | prop-2-ynyl 1H-triazole-4-carboxylate |
| 2.286 | tert-butyl 1H-triazole-4-carboxylate |
| 2.287 | isopropyl 1H-triazole-4-carboxylate |
| 2.288 | 2-(dimethylamino)ethyl 1H-triazole-4-carboxylate |
| 2.289 | 2-methoxyethyl 1H-triazole-4-carboxylate |
| 2.290 | cyclopropyl 1H-triazole-4-carboxylate |
| 2.291 | cyclopropylmethyl 1H-triazole-4-carboxylate |
| 2.292 | 1H-triazole-4-carboxamide |
| 2.293 | N-methyl-1H-triazole-4-carboxamide |
| 2.294 | N-ethyl-1H-triazole-4-carboxamide |
| 2.295 | N-propyl-1H-triazole-4-carboxamide |
| 2.296 | N-isopropyl-1H-triazole-4-carboxamide |
| 2.297 | N-prop-2-enyl-1H-triazole-4-carboxamide |
| 2.298 | N-prop-2-ynyl-1H-triazole-4-carboxamide |
| 2.299 | N-cyclopropyl-1H-triazole-4-carboxamide |
| 2.300 | N-(cyclopropylmethyl)-1H-triazole-4-carboxamide |
| 2.301 | N-(2-methoxyethyl)-1H-triazole-4-carboxamide |
| 2.302 | N-methoxy-1H-triazole-4-carboxamide |
| 2.303 | N-ethoxy-1H-triazole-4-carboxamide |
| 2.304 | N-prop-2-enyloxy-1H-triazole-4-carboxamide |
| 2.305 | N-methoxy-N-methyl-1H-triazole-4-carboxamide |
| 2.306 | N-ethoxy-N-methyl-1H-triazole-4-carboxamide |
| 2.307 | N, N-dimethyl-1H-triazole-4-carboxamide |
| 2.308 | N,N-diethyl-1H-triazole-4-carboxamide |
| 2.309 | N-ethyl-N-methyl-1H-triazole-4-carboxamide |
| 2.310 | N-prop-2-enyl-N-methyl-1H-triazole-4-carboxamide |
| 2.311 | 1H-tetrazole-5-carboxylic acid |
| 2.312 | methyl 1H-tetrazole-5-carboxylate |
| 2.313 | ethyl 1H-tetrazole-5-carboxylate |
| 2.314 | propyl 1H-tetrazole-5-carboxylate |
| 2.315 | prop-2-enyl 1H-tetrazole-5-carboxylate |
| 2.316 | prop-2-ynyl 1H-tetrazole-5-carboxylate |
| 2.317 | tert-butyl 1H-tetrazole-5-carboxylate |
| 2.318 | isopropyl 1H-tetrazole-5-carboxylate |
| 2.319 | 2-(dimethylamino)ethyl 1H-tetrazole-5-carboxylate |
| 2.320 | 2-methoxyethyl 1H-tetrazole-5-carboxylate |
| 2.321 | cyclopropyl 1H-tetrazole-5-carboxylate |
| 2.322 | cyclopropylmethyl 1H-tetrazole-5-carboxylate |
| 2.323 | 1H-tetrazole-5-carboxamide |
| 2.324 | N-methyl-1H-tetrazole-5-carboxamide |
| 2.325 | N-ethyl-1H-tetrazole-5-carboxamide |
| 2.326 | N-propyl-1H-tetrazole-5-carboxamide |
| 2.327 | N-isopropyl-1H-tetrazole-5-carboxamide |
| 2.328 | N-prop-2-enyl-1H-tetrazole-5-carboxamide |
| 2.329 | N-prop-2-ynyl-1H-tetrazole-5-carboxamide |
| 2.330 | N-cyclopropyl-1H-tetrazole-5-carboxamide |
| 2.331 | N-(cyclopropylmethyl)-1H-tetrazole-5-carboxamide |
| 2.332 | N-(2-methoxyethyl)-1H-tetrazole-5-carboxamide |
| 2.333 | N-methoxy-1H-tetrazole-5-carboxamide |
| 2.334 | N-ethoxy-1H-tetrazole-5-carboxamide |
| 2.335 | N-prop-2-enyloxy-1H-tetrazole-5-carboxamide |
| 2.336 | N-methoxy-N-methyl-1H-tetrazole-5-carboxamide |
| 2.337 | N-ethoxy-N-methyl-1H-tetrazole-5-carboxamide |
| 2.338 | N,N-dimethyl-1H-tetrazole-5-carboxamide |
| 2.339 | N,N-diethyl-1H-tetrazole-5-carboxamide |
| 2.340 | N-ethyl-N-methyl-1H-tetrazole-5-carboxamide |
| 2.341 | N-prop-2-enyl-N-methyl-1H-tetrazole-5-carboxamide |
| 2.342 | 2H-tetrazole-5-carboxylic acid |
| 2.343 | methyl 2H-tetrazole-5-carboxylate |
| 2.344 | ethyl 2H-tetrazole-5-carboxylate |
| 2.345 | propyl 2H-tetrazole-5-carboxylate |
| 2.346 | prop-2-enyl 2H-tetrazole-5-carboxylate |
| 2.347 | prop-2-ynyl 2H-tetrazole-5-carboxylate |

TABLE 2-continued

| Compound no. | Z |
|---|---|
| 2.348 | tert-butyl 2H-tetrazole-5-carboxylate |
| 2.349 | isopropyl 2H-tetrazole-5-carboxylate |
| 2.350 | 2-(dimethylamino)ethyl 2H-tetrazole-5-carboxylate |
| 2.351 | 2-methoxyethyl 2H-tetrazole-5-carboxylate |
| 2.352 | cyclopropyl 2H-tetrazole-5-carboxylate |
| 2.353 | cyclopropylmethyl 2H-tetrazole-5-carboxylate |
| 2.354 | 2H-tetrazole-5-carboxamide |
| 2.355 | N-methyl-2H-tetrazole-5-carboxamide |
| 2.356 | N-ethyl-2H-tetrazole-5-carboxamide |
| 2.357 | N-propyl-2H-tetrazole-5-carboxamide |
| 2.358 | N-isopropyl-2H-tetrazole-5-carboxamide |
| 2.359 | N-prop-2-enyl-2H-tetrazole-5-carboxamide |
| 2.360 | N-prop-2-ynyl-2H-tetrazole-5-carboxamide |
| 2.361 | N-cyclopropyl-2H-tetrazole-5-carboxamide |
| 2.362 | N-(cyclopropylmethyl)-2H-tetrazole-5-carboxamide |
| 2.363 | N-(2-methoxyethyl)-2H-tetrazole-5-carboxamide |
| 2.364 | N-methoxy-2H-tetrazole-5-carboxamide |
| 2.365 | N-ethoxy-2H-tetrazole-5-carboxamide |
| 2.366 | N-prop-2-enyloxy-2H-tetrazole-5-carboxamide |
| 2.367 | N-methoxy-N-methyl-2H-tetrazole-5-carboxamide |
| 2.368 | N-ethoxy-N-methyl-2H-tetrazole-5-carboxamide |
| 2.369 | N,N-dimethyl-2H-tetrazole-5-carboxamide |
| 2.370 | N,N-diethyl-2H-tetrazole-5-carboxamide |
| 2.371 | N-ethyl-N-methyl-2H-tetrazole-5-carboxamide |
| 2.372 | N-prop-2-enyl-N-methyl-2H-tetrazole-5-carboxamide |

Table 2.2:

This table discloses 372 specific compounds of formula (T-2) wherein $R^1$ is methyl and Z is as defined above in Table 2.

For Z as defined in Tables 1 and 2 above (with the exceptions of compound no.s 1.034, 1.036 to 1.039, 1.041 to 1.043, 1.046 to 1.048, 1.050, 1.051, 1.053 to 1.065 identified as radicals), Z groups are disclosed as a compound where the available ring nitrogen (as designated by an N—H group) is the binding point to the rest of the molecule in accordance with a Z radical for the compounds of Formula (I) of the present invention.

By way of example, the Z radical of compound 1.001 (1H-pyrazole-4-carboxylic acid) in Table 1 is:

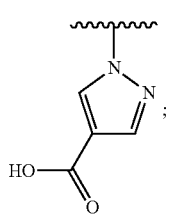

the Z radical of compound 1.021 (N-(cyclopropylmethyl)-1H-pyrazole-4-carboxamide) in Table 1 is:

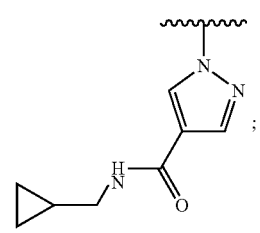

the Z radical of compound 1.035 (1H-pyrazole-4-carbonitrile) in Table 1 is:

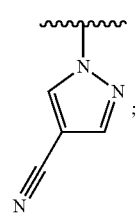

the Z radical of compound 1.049 (1H-pyrazole-4-carbaldehyde) in Table 1 is:

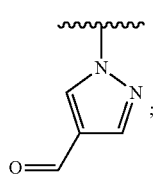

the Z radical of compound 2.194 (isopropyl 1H-1,2,4-triazole-3-carboxylate) in Table 2 is:

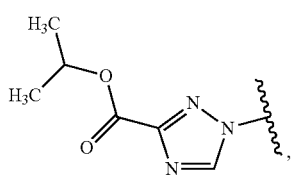

and so on.

The following general procedure was used in a combinatorial fashion using appropriate building blocks (compounds of Formulas (II) and (III)) to provide the compounds of Formula (I). The compounds prepared via the following combinatorial protocol were analyzed using LC/MS Method B.

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Compounds of Formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

Throughout this description, temperatures are given in degrees Celsius (° C.) and "mp." means melting point. LC/MS means Liquid Chromatography Mass Spectrometry and the description of the apparatus and the method (Methods A, B and C) is as follows:

The description of the LC/MS apparatus and the method A is:
SQ Detector 2 from Waters
Ionisation method: Electrospray
Polarity: positive and negative ions
Capillary (kV) 3.0, Cone (V) 30.00, Extractor (V) 2.00, Source Temperature (° C.) 150, Desolvation Temperature (° C.) 350, Cone Gas Flow (L/Hr) 0, Desolvation Gas Flow (L/Hr) 650
Mass range: 100 to 900 Da
DAD Wavelength range (nm): 210 to 500
Method Waters ACQUITY UPLC with the following HPLC gradient conditions:
(Solvent A: Water/Methanol 20:1+0.05% formic acid and Solvent B: Acetonitrile+0.05% formic acid)

| Time (minutes) | A (%) | B (%) | Flow rate (ml/min) |
|---|---|---|---|
| 0 | 100 | 0 | 0.85 |
| 1.2 | 0 | 100 | 0.85 |
| 1.5 | 0 | 100 | 0.85 |

Type of column: Waters ACQUITY UPLC HSS T3; Column length: 30 mm; Internal diameter of column: 2.1 mm; Particle Size: 1.8 micron; Temperature: 60° C.
The description of the LC/MS apparatus and the method B is:
SQ Detector 2 from Waters
Ionisation method: Electrospray
Polarity: positive ions
Capillary (kV) 3.5, Cone (V) 30.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 140 to 800 Da
DAD Wavelength range (nm): 210 to 400
Method Waters ACQUITY UPLC with the following HPLC gradient conditions:
(Solvent A: Water/Methanol 9:1+0.1% formic acid and Solvent B: Acetonitrile+0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.
The description of the LC/MS apparatus and the method C is:
SQ Detector 2 from Waters
Ionisation method: Electrospray
ACQUITY H Class UPLC, Mass Spectrometer from Waters
Polarity: positive and Negative Polarity Switch
Scan Type MS1 Scan
Capillary (kV) 3.00, Cone (V) 40.00, Desolvation Temperature (° C.) 500, Cone Gas Flow (L/Hr) 50, Desolvation Gas Flow (L/Hr) 1000
Mass range: 0 to 2000 Da
DAD Wavelength range (nm): 200 to 350
Method Waters ACQUITY UPLC with the following HPLC gradient conditions:
(Solvent A: Water+0.1% formic add and Solvent B: Acetonitrile)

| Time (minutes) | A (%) | B (%) | Flow rate (ml/min) |
|---|---|---|---|
| 0 | 70 | 30 | 0.5 |
| 0.05 | 70 | 30 | 0.6 |
| 0.8 | 5 | 95 | 0.5 |
| 1.8 | 5 | 95 | 0.5 |
| 2.45 | 70 | 30 | 0.5 |
| 2.50 | 70 | 30 | 0.5 |

Type of column: Waters ACQUITY UPLC BEH C18; Column length: 50 mm; Internal diameter of column: 2.1 mm; Particle Size: 1.7 micron; Temperature: 35° C.

Where necessary, enantiomerically pure final compounds may be obtained from racemic materials as appropriate via standard physical separation techniques, such as reverse phase chiral chromatography, or through stereoselective synthetic techniques, e.g., by using chiral starting materials.

FORMULATION EXAMPLES

| Wettable powders | a) | b) | c) |
|---|---|---|---|
| Active ingredient [compound of Formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| Active ingredient [compound of Formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment

| Emulsifiable concentrate | |
|---|---|
| active ingredient [compound of Formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of Formula (I)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient [compound of Formula (I)] | 15% |
| sodium lignosulfonate | 2% |
| Carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient [compound of Formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| Active ingredient [compound of Formula (I)] | 40% |
| propylene glycol | 10% |
| nonylphenol polyethylene glycol ether | 6% |
| (15 mol of ethylene oxide) Sodium lignosulfonate | 10% |
| Carboxymethylcellulose | 1% |
| Silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| Active ingredient [compound of Formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow-Release Capsule Suspension 28 parts of a combination of the compound of Formula I are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension Formulation contains 28% of the active ingredients. The medium capsule diameter is 8-15 microns.

The resulting formulation is applied to seeds as an aqueous suspension in an apparatus suitable for that purpose.

AIBN=azobisisobutyronitrile
DMF=dimethylformamide
DMA=dimethylacetamide
DIPEA=N,N-di-isopropylethylamine
EtOAc=ethyl acetate
HCl=hydrochloric acid
mp=melting point
° C.=degrees celsius
MeOH=methyl alcohol
NaOH=sodium hydroxide
NBS=N-bromosuccinimide
min=minutes
rt=room temperature
h=hour(s)

TFAA=trifluoroacetic acid anhydride
THF=tetrahydrofuran
R_f=retention time (in minutes)
LC/MS=Liquid Chromatography Mass Spectrometry (description of the apparatus and the methods used for LC/MS analysis are given above)

PREPARATION EXAMPLES

Using the synthetic techniques described both above and below, compounds of formula (I) may be prepared accordingly.

Example 1

This example illustrates the preparation of N,N-dimethyl-1-[[5-[5-(trifluoromethyl)-1,2,4-oxadiazol-3-yl]-2-thienyl]methyl]-1,2,4-triazol-3-amine (Compound 1.4 of Table T1)

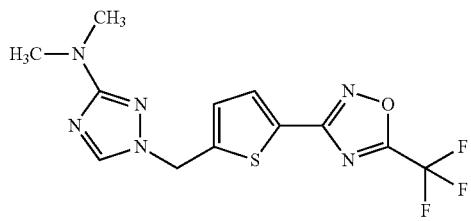 [SMILES: CN(C)c1ncn(Cc2ccc(-c3noc(C(F)(F)F)n3)s2)n1]

Step 1: Preparation of N'-hydroxy-5-methyl-thiophene-2-carboxamidine

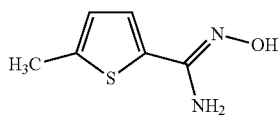

To a suspension of 5-methylthiophene-2-carbonitrile (9.0 g, 73 mmol) in ethanol (365 mL) stirring at room temperature was added triethylamine (20.6 mL, 146 mmol) followed by the portionwise introduction of hydroxylamine hydrochloride (10.3 g, 146 mmol). The reaction contents were heated at reflux for 3.5 hours, cooled to 25° C., and concentrated under reduced pressure to provide N'-hydroxy-5-methyl-thiophene-2-carboxamidine as a crude residue which was used in the next transformations without further purification. LC/MS (Method A) retention time=0.24 minutes, 156 (M+H).

Step 2: Preparation of 3-(5-methyl-2-thienyl)-5-(trifluoromethyl)-1,2,4-oxadiazole

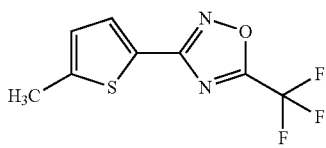

To a suspension of crude N'-hydroxy-5-methyl-thiophene-2-carboxamidine (32.0 g) in tetrahydrofuran (1.0 L) was introduced pyridine (24 mL, 292 mmol) and the contents were cooled to 10° C. To this suspension, TFAA (30.9 mL, 219 mL) was introduced dropwise. The reaction mixture was allowed to warm to 25° C. overnight, and then concentrated at reduced pressure. The resultant residue was dissolved in ethyl acetate, washed with an aqueous 1M HCl solution, water, and a saturated aqueous Na_2CO_3 solution. The organic layer was dried over sodium sulfate, filtered, and the volatiles were removed at reduced pressure. The crude residue was purified by flash chromatography over silica gel using a cyclohexane/EtOAc eluent gradient to afford 3-(5-methyl-2-thienyl)-5-(trifluoromethyl)-1,2,4-oxadiazole as a clear oil (13.1 g, 76% yield). LC/MS (Method A) retention time=1.13 minutes, mass not detected.
$^1$H NMR (400 MHz, CDCl_3) δ ppm: 7.68 (d, 1H), 6.84 (d, 1H), 2.57 (s, 3H).
$^{19}$F NMR (400 MHz, CDCl_3) δ ppm: −65.44 (s).

Step 3a: Preparation of 3-[5-(bromomethyl-2-thienyl]-5-(trifluoromethyl)-1,2,4-oxadiazole

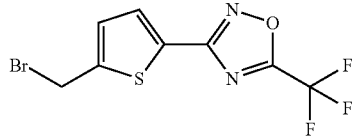 [SMILES: FC(F)(F)c1nc(-c2ccc(CBr)s2)no1]

To a solution of 3-(5-methyl-2-thienyl)-5-(trifluoromethyl)-1,2,4-oxadiazole (13.1 g, 55.7 mmol) and tetrachloromethane (111 mL) under argon atmosphere was added AIBN (0.93 g, 5.6 mmol) then NBS (11.02 g, 61.3 mmol). The contents were heated at 70° C. for 18 hours. The mixture was cooled to 25° C. then diluted with dichloromethane and water. The layers were separated, the organic phase was dried over sodium sulfate, and the volatiles were removed under reduced pressure. The crude residue was purified by flash chromatography over silica gel using a cyclohexane/EtOAc eluent gradient to afford 3-[5-(bromomethyl)-2-thienyl]-5-(trifluoromethyl)-1,2,4-oxadiazole as a yellow oil (3.86 g, 22% yield). LC/MS (Method A) retention time=1.14 minutes, mass not detected.
$^1$H NMR (400 MHz, CDCl_3) δ ppm: 8.11 (d, 1H), 7.55 (d, 1H), 4.53 (s, 2H).
$^{19}$F NMR (400 MHz, CDCl_3) δ ppm: −65.31 (s).
3-[5-(dibromomethyl)-2-thienyl]-5-(trifluoromethyl)-1,2,4-oxadiazole was isolated as by-product as a yellow amorphous solid (13.0 g)

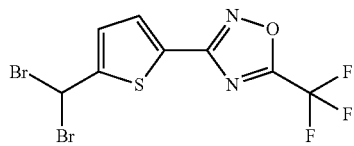 [SMILES: FC(F)(F)c1nc(-c2ccc(C(Br)Br)s2)no1]

$^1$H NMR (400 MHz, CDCl_3) δ ppm: 7.73 (d, 1H), 7.32 (d, 1H), 6.91 (s, 1H).

Step 4: Preparation of N,N-dimethyl-1-[[5-[5-(trifluoromethyl)-1,2,4-oxadiazol-3-yl]-2-thienyl]methyl]-1,2,4-triazol-3-amine A solution of 3-[5-(bromomethyl)-2-thienyl]-5-(trifluoromethyl)-1,2,4-oxadiazole (150 mg, 0.48 mmol), N,N-dimethyl-4H-1,2,4-triazol-3-amine (64 mg, 0.57 mmol), and potassium carbonate (133 mg, 0.96 mmol) in acetonitrile (6.0 mL) was stirred at rt overnight. The solids were removed by filtration, washed with ethyl acetate, and the volatiles were removed under reduced pressure. The resultant residue purified by flash chromatography over silica gel using a cyclohexane/EtOAc eluent gradient to afford N,N-dimethyl-1-[[5-[5-(trifluoromethyl)-1,2,4-oxadiazol-3-yl]-2-thienyl]methyl]-1,2,4-triazol-3-amine as a yellow solid (49 mg, 30% yield). LC/MS (Method A) retention time=0.96 minutes, 345 (M+H). mp: 113-116° C.

$^1$H NMR (400 MHz, CDCl$_3$) δ ppm: 7.78 (s, 1H), 7.75 (d, 1H), 7.11 (d, 1H), 5.37 (s, 2H), 2.99 (s, 6H).

Example 2

This example illustrates the preparation of methyl 1-[[5-[5-(trifluoromethyl)-1,2,4-oxadiazol-3-yl]-2-thienyl]methyl]-1,2,4-triazole-3-carboxylate (Compound 1.6 of Table T1)

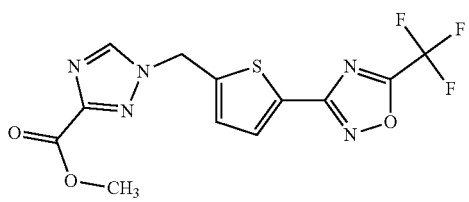 [SMILES: COC(=O)c1ncn(Cc2ccc(-c3noc(C(F)(F)F)n3)s2)n1]

A mixture of 3-[5-(bromomethyl)-2-thienyl]-5-(trifluoromethyl)-1,2,4-oxadiazole (1.0 g, 3.2 mmol), methyl 1H-1,2,4-triazole-3-carboxylate (610 mg, 4.8 mmol) and potassium carbonate (880 mg, 6.4 mmol) in acetonitrile (32 mL) was heated at 110° C. for 2 hours. The resultant orange suspension was filtered to remove the solids and the filtrate solution was then concentrated under reduced pressure. The resultant crude residue was purified by chromatography on silica gel using a cyclohexane/ethyl acetate gradient to afford 750 mg of the title compound as a white solid. LC/MS (Method A) retention time=0.91 minutes, 360 (M+H).

$^1$H NMR (400 MHz, CDCl$_3$) δ ppm: 8.25 (s, 1H), 7.81 (d, 1H), 7.22 (d, 1H), 5.65 (s, 2H), 4.05 (s, 3H).

methyl 2-[[5-[5-(trifluoromethyl)-1,2,4-oxadiazol-3-yl]-2-thienyl]methyl]-1,2,4-triazole-3-carboxylate (Compound 1.55 of Table T1) was isolated as a byproduct in form of a colorless gum (306 mg), LC/MS (Method A) retention time=0.91 minutes, 360 (M+H).

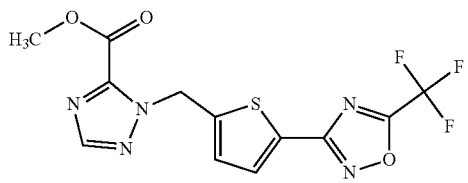 [SMILES: COC(=O)c1ncnn1Cc1ccc(-c2noc(C(F)(F)F)n2)s1]

$^1$H NMR (400 MHz, CDCl$_3$) δ ppm: 8.05 (s, 1H), 7.75 (d, 1H), 7.22 (d, 1H), 6.50 (s, 2H), 4.05 (s, 3H).

Example 3

This example illustrates the preparation of propyl 2-[[5-[5-(trifluoromethyl)-1,2,4-oxadiazol-3-yl]-2-thienyl]methyl]-1,2,4-triazole-3-carboxylate (Compound 1.44 of Table T1)

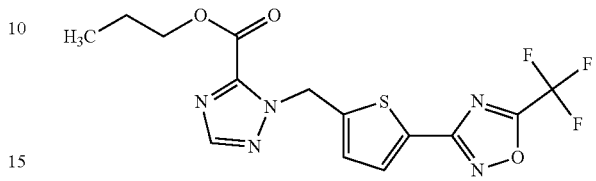

To a solution of methyl 2-[5-[5-(trifluoromethyl)-1,2,4-oxadiazol-3-yl-2-thienyl]methyl]-1,2,4-triazole-3-carboxylate (100 mg, 0.27 mmol) and propanol (0.83 mL) was introduced concentrated sulfuric acid (0.01 mL). The white suspension was stirred 12 hours under reflux during which time it turned into a clear solution. The reaction mixture was concentrated under reduced pressure and the residue was purified by flash chromatography on silica gel using a cyclohexane/ethyl acetate gradient to afford 47 mg of the title compound as a colorless gum. LC/MS (Method A) retention time=1.10 minutes, 388 (M+H).

$^1$H NMR (400 MHz, CDCl$_3$) δ ppm: 8.05 (s, 1H), 7.75 (d, 1H), 7.25 (d, 1H), 6.05 (s, 2H), 4.45 (t, 2H), 1.85 (m, 2H), 1.05 (t, 3H).

Example 4

This example illustrates the preparation of N-methyl-N-methoxy-2-[[5-[5-(trifluoromethyl)-1,2,4-oxadiazol-3-yl]-2-thienyl]methyl]-1,2,4-triazole-3-carboxamide (Compound 1.61 of Table T1)

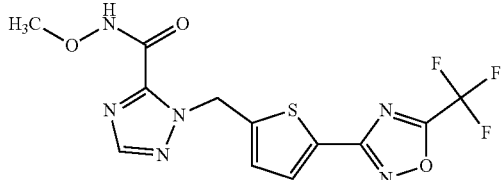

To a clear solution of O-methylhydroxylamine hydrochloride (136 mg, 1.67 mmol) in toluene (2 mL) was introduced dropwise diethylaluminum chloride (1M in toluene, 1.67 mL, 1.67 mmol). After 10 minutes, methyl 2-[[5-[5-(trifluoromethyl)-1,2,4-oxadiazol-3-yl]-2-thienyl]methy]-1,2,4-triazole-3-carboxylate (150 mg, 0.41 mmol) was added and the mixture was heated for 12 hours at 70° C. The reaction was quenched with water (ca. 0.030 mL) and the suspension was concentrated under reduced pressure. The resultant residue was purified by flash chromatography on silica gel using a cyclohexane/ethyl acetate gradient to afford 64 mg of the title compound as a white solid, m.p: 135-140° C.; LC/MS (Method A) retention time=0.93 minutes, 375 (M+H).

$^1$H NMR (400 MHz, CDCl$_3$) δ ppm: 7.95 (s, 1H), 7.75 (d, 1H), 7.35 (d, 1H), 6.12 (s, 2H), 3.97 (s, 3H).

Example 5

This example illustrates the preparation of methyl 1-[[5-[5-(trifluoromethyl)-1,2,4-oxadiazol-3-yl]-2-thienyl]methyl]pyrazole-3-carboxylate (Compound 1.53 of Table T1)

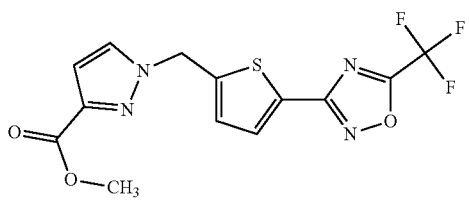 [SMILES: COC(=O)c1ccn(Cc2ccc(-c3noc(C(F)(F)F)n3)s2)n1]

A mixture of 3-[5-(bromomethyl)-2-thienyl]-5-(trifluoromethyl)-1,2,4-oxadiazole (1.0 g, 3.2 mmol), methyl 1H-pyrazole-3-carboxylate (600 mg, 4.8 mmol) and potassium carbonate (880 mg, 6.4 mmol) In acetonitrile (32 mL) was heated at 110° C. for 2 hours. The orange suspension was filtered to remove the solids and the filtrate solution was then concentrated under reduced pressure. The resultant crude residue was purified by flash chromatography on silica gel using a cyclohexane/ethyl acetate gradient to afford 610 mg of the title compound as a white solid. LC/MS (Method A) retention time=1.00 minutes, 359 (M+H).

$^1$H NMR (400 MHz, CDCl$_3$) δ ppm: 7.78 (d, 1H), 7.51 (d, 1H), 7.12 (d, 1H), 6.89 (d, 1H), 5.61 (s, 2H), 3.98 (s, 3H).

methyl 2-[[5-[5-(trifluoromethyl)-1,2,4-oxadiazol-3-yl]-2-thienyl]methyl]pyrazole-3-carboxylate (Compound 1.54 of Table T1) was isolated as a byproduct in form of a white solid (274 mg). LC/MS (Method A) retention time=1.10 minutes, 359 (M+H).

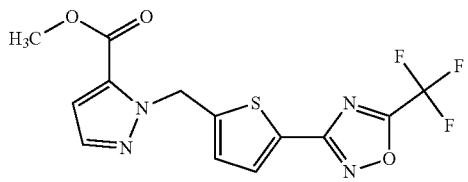 [SMILES: COC(=O)c1ccnn1Cc1ccc(-c2noc(C(F)(F)F)n2)s1]

$^1$H NMR (400 MHz, CDCl$_3$) δ ppm: 7.72 (d, 1H), 7.58 (d, 1H), 7.18 (d, 1H), 6.89 (d, 1H), 6.05 (s, 2H), 3.98 (s, 3H).

Example 6

This example illustrates the preparation of ethyl 1-[[5-[5-(trifluoromethyl)-1,2,4-oxadiazol-3-yl]-2-thienyl]methyl]pyrazole-3-carboxylate (Compound 1.42 of Table T1)

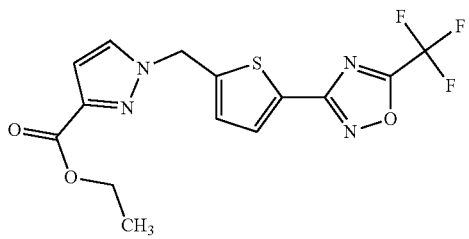 [SMILES: CCOC(=O)c1ccn(Cc2ccc(-c3noc(C(F)(F)F)n3)s2)n1]

To a solution of methyl 1-[[5-[5-(trifluoromethyl)-1,2,4-oxadiazol-3-yl]-2-thienyl]methyl]pyrazole-3-carboxylate (100 mg, 0.27 mmol) and ethanol (0.83 mL) was introduced concentrated sulfuric acid (0.01 mL). The white suspension was stirred for 2 hours at reflux during which time it became a clear solution. The reaction mixture was concentrated under reduced pressure and the resultant crude residue was purified by reverse phase column chromatography using a water/acetonitrile eluent gradient to afford 20 mg of the title compound as a white solid. mp: 120-124° C.; LC/MS (Method A) retention time=1.07 minutes, 373 (M+H).

$^1$H NMR (400 MHz, CDCl$_3$) δ ppm: 7.71 (d, 1H), 7.52 (d, 1H), 7.12 (d, 1H), 6.85 (d, 1H), 5.62 (s, 2H), 4.45 (q, 2H), 1.45 (t, 3H).

Example 7

This example illustrates the preparation of N,N-dimethyl-2-[[5-[5-(trifluoromethyl)-1,2,4-oxadiazol-3-yl]-2-thienyl]methyl]pyrazole-3-carboxamide (Compound 1.58 of Table T1)

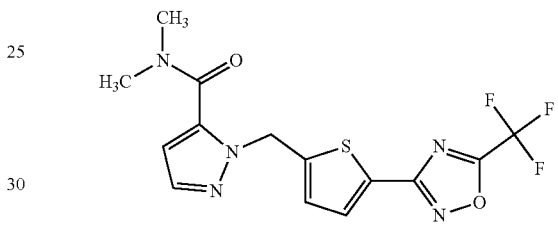

To a clear solution of N-methylmethanamine hydrochloride (136 mg, 1.67 mmol) in toluene (2 mL) was introduced dropwise diethylaluminum chloride (1M in toluene, 1.67 mL, 1.67 mmol). After 10 minutes, methyl 2-[[5-[5-(trifluoromethyl)-1,2,4-oxadiazol-3-yl]-2-thienyl]methyl]pyrazole-3-carboxylate (150 mg, 0.41 mmol) was added and the mixture was heated for 12 hours at 70° C. The reaction was quenched with water (ca. 0.030 mL) and the suspension was concentrated under reduced pressure.

The resultant residue was purified by flash chromatography on silica gel using a cyclohexane/ethyl acetate gradient to afford the title compound (105 mg, 67% yield) as a yellow gum. LC/MS (Method A) retention time=0.96 minutes, 372 (M+H).

$^1$H NMR (400 MHz, CDCl$_3$) δ ppm: 7.71 (d, 1H), 7.55 (d, 1H), 7.12 (d, 1H), 6.42 (d, 1H), 5.78 (s, 2H), 3.05 (s, 3H), 3.15 (s, 3H).

The following general procedure was performed in a combinatorial fashion using appropriate building blocks (compounds of Formula (II) and (III)) to provide the compounds of Formula (I). The compounds prepared via the following combinatorial protocol were analyzed using LC/MS Method B.

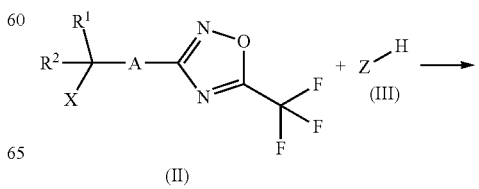

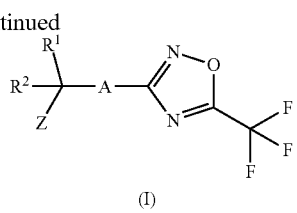

(I)

By way of exemplification, [[5-(trifluoromethyl)-1,2,4-oxadiazol-3-yl]heteroaryl]methylbromide derivatives of formula (II) (0.03 mmol) in acetonitrile (1.0 mL) was transferred to microwave vials containing amine derivative of Formula (III) (0.03 mmol), potassium carbonate (0.06 mmol), and were stirred under microwaves irradiation at 120° C. for 20 minutes in the parallel microwave apparatus. The solvent was removed under a stream of nitrogen. The resultant crude residues were solubulized in a mixture of MeOH (250 μL) and DMA (500 μL) and directly submitted for preparative LC/MS purification which provided the compounds of Formula (I). Structures of isomers were assigned by NMR techniques.

Where necessary, enantiomerically pure final compounds may be obtained from racemic materials as appropriate via standard physical separation techniques, such as reverse phase chiral chromatography, or through stereoselective synthetic techniques, (e.g., by using chiral starting materials).

TABLE T1

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.1 | ethyl 1-[[5-[5-(trifluoromethyl)-1,2,4-oxadiazol-3-yl]-2-thienyl]methyl]pyrazole-4-carboxylate | 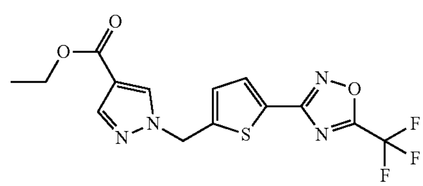 [SMILES: CCOC(=O)c1cnn(Cc2ccc(-c3noc(C(F)(F)F)n3)s2)c1] | 1.08 | 373.2 | B | 115.7-116.5 |
| 1.2 | 3-[5-(1,2,4-triazol-1-ylmethyl)-2-thienyl]-5-(trifluoromethyl)-1,2,4-oxadiazole | 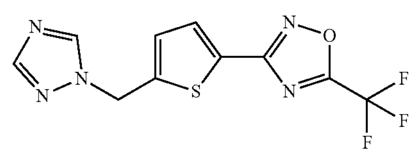 [SMILES: FC(F)(F)c1nc(-c2ccc(Cn3cncn3)s2)no1] | 0.89 | 302.3 | A | |
| 1.3 | 5,5-dimethyl-2-[[5-[5-(trifluoromethyl)-1,2,4-oxadiazol-3-yl]-2-thienyl]methyl]isoxazolidin-3-one | 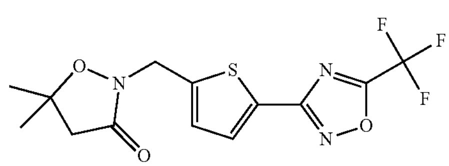 [SMILES: CC1(C)CC(=O)N(Cc2ccc(-c3noc(C(F)(F)F)n3)s2)O1] | 1.04 | 348.2 | A | |
| 1.4 | N,N-dimethyl-1-[[5-[5-(trifluoromethyl)-1,2,4-oxadiazol-3-yl]-2-thienyl]methyl]-1,2,4-triazol-3-amine | 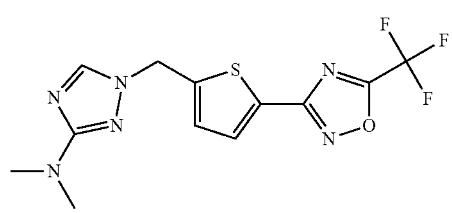 [SMILES: CN(C)c1ncn(Cc2ccc(-c3noc(C(F)(F)F)n3)s2)n1] | | | | 113-116 |
| 1.5 | 3-[5-[(4-methylpyrazol-1-yl)methyl]-2-thienyl]-5-(trifluoromethyl)-1,2,4-oxadiazole | 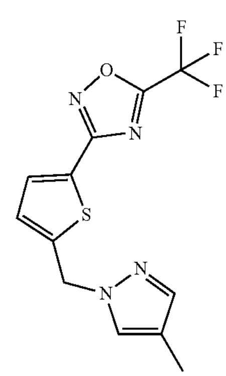 [SMILES: Cc1cnn(Cc2ccc(-c3noc(C(F)(F)F)n3)s2)c1] | 1.63 | 315 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.6 | methyl 1-[[5-[5-(trifluoromethyl)-1,2,4-oxadiazol-3-yl]-2-thienyl]methyl]-1,2,4-triazole-3-carboxylate | 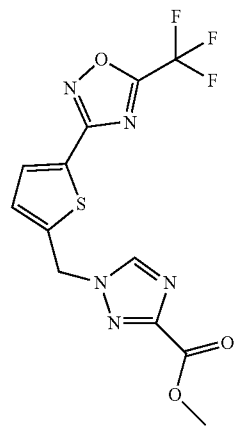 [SMILES: COC(=O)c1ncn(Cc2ccc(-c3noc(C(F)(F)F)n3)s2)n1] | 1.34 | 360 | B | |
| 1.7 | 3-[5-(pyrazol-1-ylmethyl)-2-thienyl]-5-(trifluoromethyl)-1,2,4-oxadiazole | 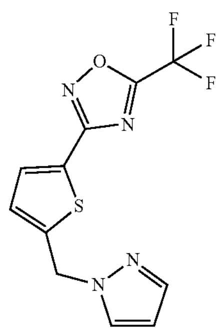 [SMILES: FC(F)(F)c1nc(-c2ccc(Cn3cccn3)s2)no1] | 1.52 | 301 | B | |
| 1.8 | 3-[5-(pyrrolo[2,3-b]pyridin-1-ylmethyl)-2-thienyl]-5-(trifluoromethyl)-1,2,4-oxadiazole | 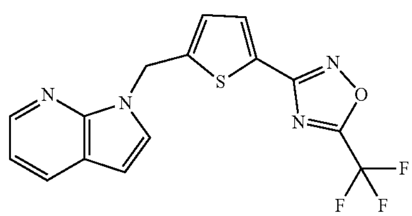 [SMILES: FC(F)(F)c1nc(-c2ccc(Cn3ccc4cccnc43)s2)no1] | 0.95 | 351 | B | |
| 1.9 | 3-[5-[(4-nitropyrazol-1-yl)methyl]-2-thienyl]-5-(trifluoromethyl)-1,2,4-oxadiazole | 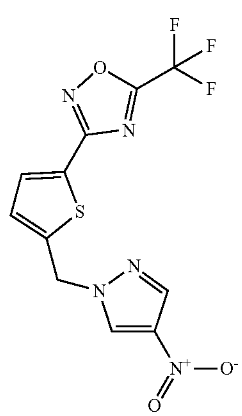 [SMILES: O=[N+]([O-])c1cnn(Cc2ccc(-c3noc(C(F)(F)F)n3)s2)c1] | 1.63 | 346.4 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.10 | 3-[5-[[5-(2-bromophenyl)tetrazol-1-yl]methyl]-2-thienyl]-5-(trifluoromethyl)-1,2,4-oxadiazole | 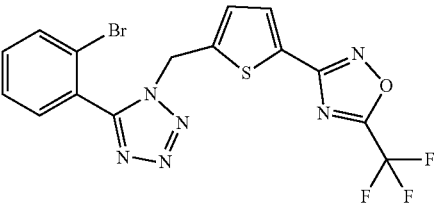 [SMILES: FC(F)(F)c1nc(-c2ccc(Cn3nnnc3-c3ccccc3Br)s2)no1] | 1.74 | 457 | B | |
| 1.11 | 1-[[5-[5-(trifluoromethyl)-1,2,4-oxadiazol-3-yl]-2-thienyl]methyl]pyrazole-4-carbonitrile | 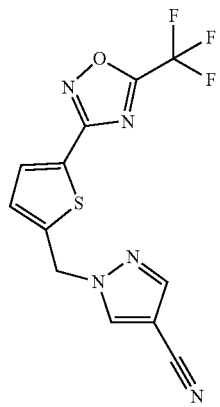 [SMILES: N#Cc1cnn(Cc2ccc(-c3noc(C(F)(F)F)n3)s2)c1] | 1.54 | 326 | B | |
| 1.12 | 3-[5-[(4-fluoropyrazol-1-yl)methyl]-2-thienyl]-5-(trifluoromethyl)-1,2,4-oxadiazole | 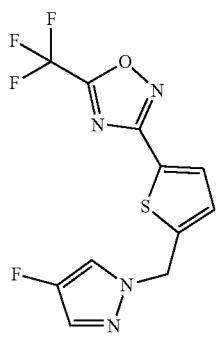 [SMILES: Fc1cnn(Cc2ccc(-c3noc(C(F)(F)F)n3)s2)c1] | 1.63 | 319 | B | |
| 1.13 | N,N-dimethyl-2-[[5-[5-(trifluoromethyl)-1,2,4-oxadiazol-3-yl]-2-thienyl]methyl]-1,2,4-triazol-3-amine | 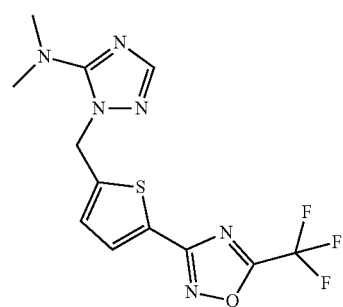 [SMILES: CN(C)c1ncnn1Cc1ccc(-c2noc(C(F)(F)F)n2)s1] | 1.44 | 345.1 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.14 | 5-(difluoromethyl)-2-[[5-[5-(trifluoromethyl)-1,2,4-oxadiazol-3-yl]-2-thienyl]methyl]-1,2,4-triazol-3-amine | 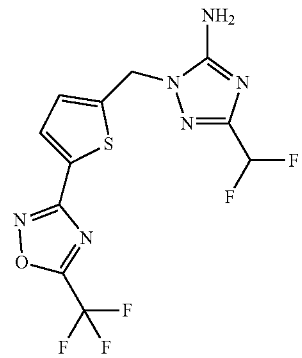 [SMILES: Nc1nc(C(F)F)nn1Cc1ccc(-c2noc(C(F)(F)F)n2)s1] | 1.36 | 367 | B | |
| 1.15 | 3-[5-(pyrrolidin-1-ylmethyl)-2-thienyl]-5-(trifluoromethyl)-1,2,4-oxadiazole | 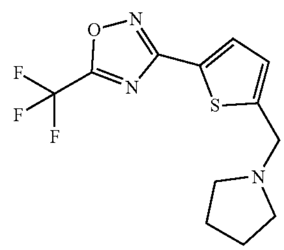 [SMILES: FC(F)(F)c1nc(-c2ccc(CN3CCCC3)s2)no1] | 0.84 | 304 | B | |
| 1.16 | 5-methyl-2-[[5-[5-(trifluoromethyl)-1,2,4-oxadiazol-3-yl]-2-thienyl]methyl]pyrazol-3-amine | 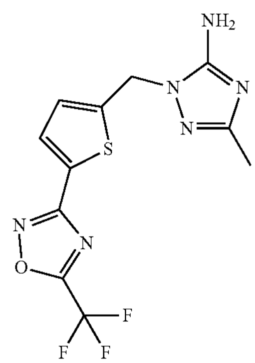 [SMILES: Cc1nc(N)n(Cc2ccc(-c3noc(C(F)(F)F)n3)s2)n1] | 1.14 | 330 | B | |
| 1.17 | 3-[5-(imidazol-1-ylmethyl)-2-thienyl]-5-(trifluoromethyl)-1,2,4-oxadiazole | 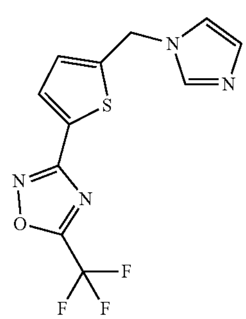 [SMILES: FC(F)(F)c1nc(-c2ccc(Cn3ccnc3)s2)no1] | 0.83 | 301 | B | |
| 1.18 | 4-[[5-[5-(trifluoromethyl)-1,2,4-oxadiazol-3-yl]-2-thienyl]methyl]morpholine | 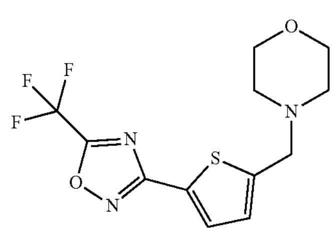 [SMILES: FC(F)(F)c1nc(-c2ccc(CN3CCOCC3)s2)no1] | 0.89 | 320 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.19 | methyl 3-(methoxymethyl)-1-[[5-[5-(trifluoromethyl)-1,2,4-oxadiazol-3-yl]-2-thienyl]methyl]pyrazole-4-carboxylate | 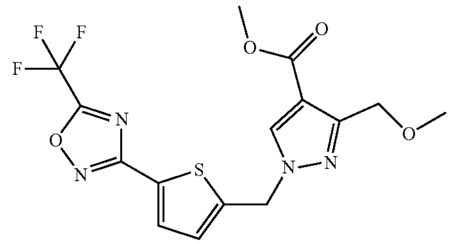 [SMILES: COCc1nn(Cc2ccc(-c3noc(C(F)(F)F)n3)s2)cc1C(=O)OC] | 1.58 | 403.1 | B | |
| 1.20 | 3-[5-(azetidin-1-ylmethyl)-2-thienyl]-5-(trifluoromethyl)-1,2,4-oxadiazole | 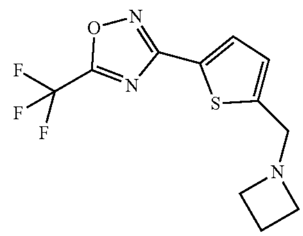 [SMILES: FC(F)(F)c1nc(-c2ccc(CN3CCC3)s2)no1] | 0.82 | 290 | B | |
| 1.21 | 3-[5-[(3,5-dimethylpyrazol-1-yl)methyl]-2-thienyl]-5-(trifluoromethyl)-1,2,4-oxadiazole | 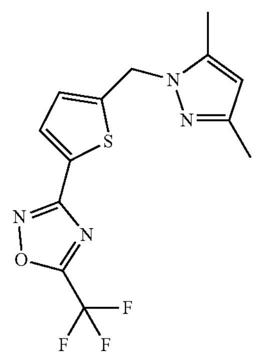 [SMILES: Cc1cc(C)n(Cc2ccc(-c3noc(C(F)(F)F)n3)s2)n1] | 1.68 | 329 | B | |
| 1.22 | 1-[[5-[5-(trifluoromethyl)-1,2,4-oxadiazol-3-yl]-2-thienyl]methyl]pyrazole-4-carbaldehyde | 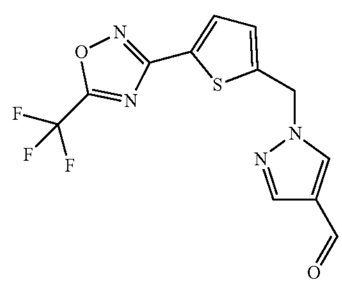 [SMILES: O=Cc1cnn(Cc2ccc(-c3noc(C(F)(F)F)n3)s2)c1] | 1.41 | 3.29 | B | |
| 1.23 | 3-[5-[(6-methoxybenzimidazol-1-yl)methyl]-2-thienyl]-5-(trifluoromethyl)-1,2,4-oxadiazole | 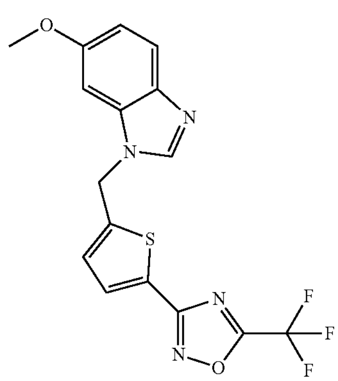 [SMILES: COc1ccc2ncn(Cc3ccc(-c4noc(C(F)(F)F)n4)s3)c2c1] | 1.25 | 381.1 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.24 | 3-[5-[(5-methoxybenzimidazol-1-yl)methyl]-2-thienyl]-5-(trifluoromethyl)-1,2,4-oxadiazole | 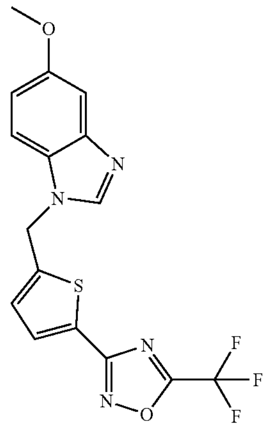 [SMILES: COc1ccc2c(c1)ncn2Cc1ccc(-c2noc(C(F)(F)F)n2)s1] | 1.28 | 381.1 | B | |
| 1.25 | 3-[5-(benzimidazol-1-ylmethyl)-2-thienyl]-5-(trifluoromethyl)-1,2,4-oxadiazole | 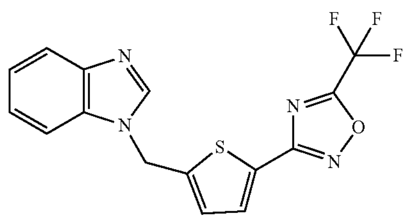 [SMILES: FC(F)(F)c1nc(-c2ccc(Cn3cnc4ccccc43)s2)no1] | 1.28 | 351 | B | |
| 1.26 | ethyl 1-[[4-[5-(trifluoromethyl)-1,2,4-oxadiazol-3-yl]-2-thienyl]methyl]pyrazole-4-carboxylate | 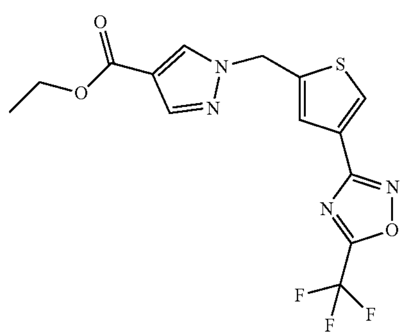 [SMILES: CCOC(=O)c1cnn(Cc2cc(-c3noc(C(F)(F)F)n3)cs2)c1] | | | | 119-123 |
| 1.27 | 6-methyl-1-[[4-[5-(trifluoromethyl)-1,2,4-oxadiazol-3-yl]-2-thienyl]methyl]pyridin-2-one | 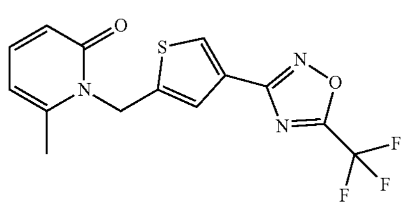 [SMILES: Cc1cccc(=O)n1Cc1cc(-c2noc(C(F)(F)F)n2)cs1] | 0.97 | 342 | A | |
| 1.28 | 5,5-dimethyl-2-[[4-[5-(trifluoromethyl)-1,2,4-oxadiazol-3-yl]-2-thienyl]methyl] isoxazolidin-3-one | 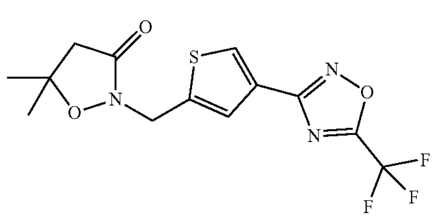 [SMILES: CC1(C)CC(=O)N(Cc2cc(-c3noc(C(F)(F)F)n3)cs2)O1] | 1.03 | 348 | A | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.29 | 2-[[4-[5-(trifluoromethyl)-1,2,4-oxadiazol-3-yl]-2-thienyl]methyl]-1,2-thiazolidine 1,1-dioxide | 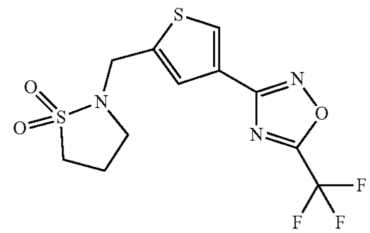 [SMILES: O=S1(=O)CCCN1Cc1cc(-c2noc(C(F)(F)F)n2)cs1] | 0.96 | mass not detected | A | |
| 1.30 | ethyl 1-[1-[5-[5-(trifluoromethyl)-1,2,4-oxadiazol-3-yl]-2-thienyl]ethyl]pyrazole-4-carboxylate | 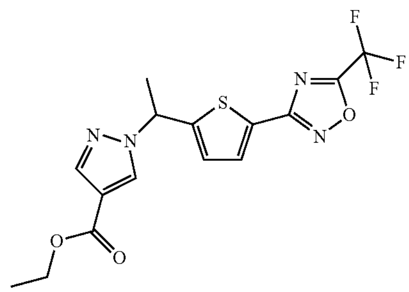 [SMILES: CCOC(=O)c1cnn(C(C)c2ccc(-c3noc(C(F)(F)F)n3)s2)c1] | 1.12 | 387 | A | |
| 1.31 | 1-[[4-[5-(trifluoromethyl)-1,2,4-oxadiazol-3-yl]-2-thienyl]methyl]piperidin-2-one | 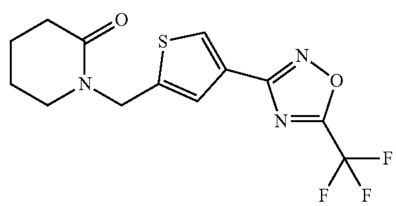 [SMILES: O=C1CCCCN1Cc1cc(-c2noc(C(F)(F)F)n2)cs1] | 0.98 | 332 | A | |
| 1.32 | 2-[1-[5-[5-(trifluoromethyl)-1,2,4-oxadiazol-3-yl]-2-thienyl]ethyl]-1,2-thiazolidine 1,1-dioxide | 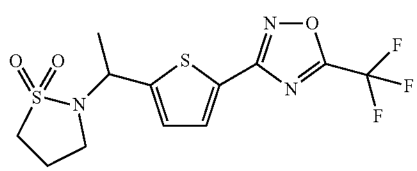 [SMILES: CC(c1ccc(-c2noc(C(F)(F)F)n2)s1)N1CCCS1(=O)=O] | 1.01 | 384 | A | |
| 1.33 | 6-methyl-1-[1-[5-[5-(trifluoromethyl)-1,2,4-oxadiazol-3-yl]-2-thienyl]ethyl]pyridin-2-one | 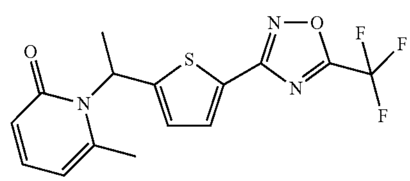 [SMILES: Cc1cccc(=O)n1C(C)c1ccc(-c2noc(C(F)(F)F)n2)s1] | 1.02 | 356 | A | |
| 1.34 | 1-[1-[5-[5-(trifluoromethyl)-1,2,4-oxadiazol-3-yl]-2-thienyl]ethyl]piperidin-2-one | 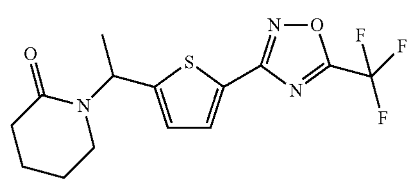 [SMILES: CC(c1ccc(-c2noc(C(F)(F)F)n2)s1)N1CCCCC1=O] | 1.04 | 346 | A | |
| 1.35 | azetidin-1-yl-[1-[1-[5-[5-(trifluoromethyl)-1,2,4-oxadiazol-3-yl]-2-thienyl]ethyl]pyrazol-4-yl]methanone | 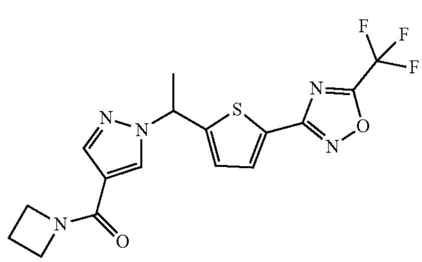 [SMILES: CC(c1ccc(-c2noc(C(F)(F)F)n2)s1)n1cc(C(=O)N2CCC2)cn1] | | | | 76-78 |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.36 | 1-[[5-[5-(trifluoromethyl)-1,2,4-oxadiazol-3-yl]-2-thienyl]methyl]pyrazole-4-carboxylic acid | 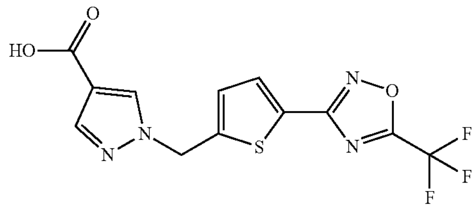 [SMILES: O=C(O)c1cnn(Cc2ccc(-c3noc(C(F)(F)F)n3)s2)c1] | | | | 182-185 |
| 1.37 | 1-[1-[5-[5-(trifluoromethyl)-1,2,4-oxadiazol-3-yl]-2-thienyl]ethyl]pyrazole-4-carboxylic acid | 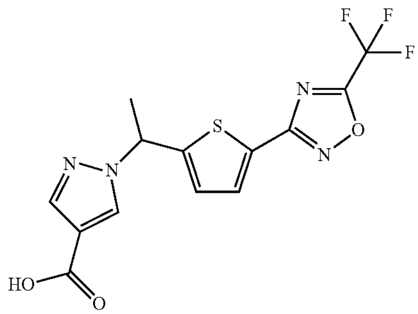 [SMILES: CC(c1ccc(-c2noc(C(F)(F)F)n2)s1)n1cc(C(=O)O)cn1] | | | | 133-143 |
| 1.38 | N-methyl-1-[[5-[5-(trifluoromethyl)-1,2,4-oxadiazol-3-yl]-2-thienyl]methyl]pyrazole-4-carboxamide | 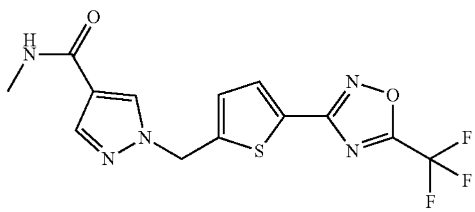 [SMILES: CNC(=O)c1cnn(Cc2ccc(-c3noc(C(F)(F)F)n3)s2)c1] | | | | 150.8-155.7 |
| 1.39 | N-(2-methoxyethyl)-1-[[5-[5-(trifluoromethyl)-1,2,4-oxadiazol-3-yl]-2-thienyl]methyl]pyrazole-4-carboxamide | 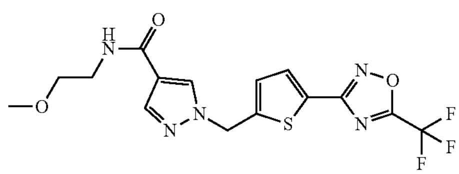 [SMILES: COCCNC(=O)c1cnn(Cc2ccc(-c3noc(C(F)(F)F)n3)s2)c1] | | | | 135.3-137.9 |
| 1.40 | ethyl 1-[[5-[5-(trifluoromethyl)-1,2,4-oxadiazol-3-yl]-2-thienyl]methyl]-1,2,4-triazole-3-carboxylate | 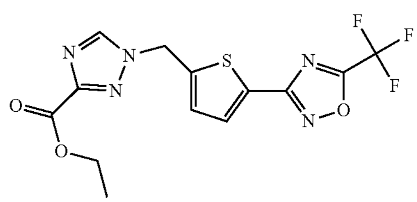 [SMILES: CCOC(=O)c1ncn(Cc2ccc(-c3noc(C(F)(F)F)n3)s2)n1] | | | | 136-140 |
| 1.41 | ethyl 2-[[5-[5-(trifluoromethyl)-1,2,4-oxadiazol-3-yl]-2-thienyl]methyl]-1,2,4-triazole-3-carboxylate | 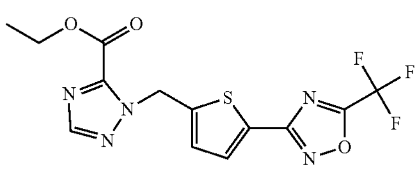 [SMILES: CCOC(=O)c1ncnn1Cc1ccc(-c2noc(C(F)(F)F)n2)s1] | 1.05 | 374 | A | |
| 1.42 | ethyl 1-[[5-[5-(trifluoromethyl)-1,2,4-oxadiazol-3-yl]-2-thienyl]methyl]pyrazole-3-carboxylate | 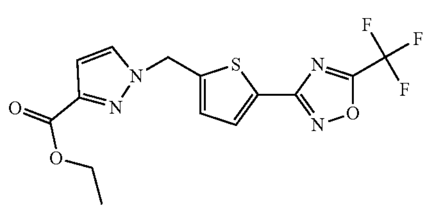 [SMILES: CCOC(=O)c1ccn(Cc2ccc(-c3noc(C(F)(F)F)n3)s2)n1] | | | | 120-124 |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.43 | propyl 1-[[5-[5-(trifluoromethyl)-1,2,4-oxadiazol-3-yl]-2-thienyl]methyl]-1,2,4-triazole-3-carboxylate | 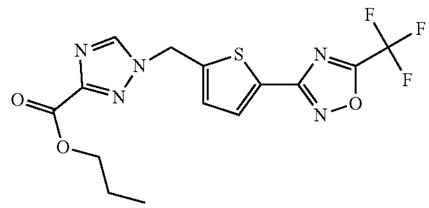 [SMILES: CCCOC(=O)c1ncn(Cc2ccc(-c3noc(C(F)(F)F)n3)s2)n1] | | | | 140-160 |
| 1.44 | propyl 2-[[5-[5-(trifluoromethyl)-1,2,4-oxadiazol-3-yl]-2-thienyl]methyl]-1,2,4-triazole-3-carboxylate | 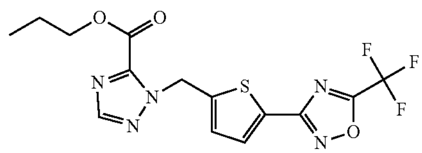 [SMILES: CCCOC(=O)c1ncnn1Cc1ccc(-c2noc(C(F)(F)F)n2)s1] | 1.09 | 388 | A | |
| 1.45 | ethyl 2-[[5-[5-(trifluoromethyl)-1,2,4-oxadiazol-3-yl]-2-thienyl]methyl]pyrazole-3-carboxylate | 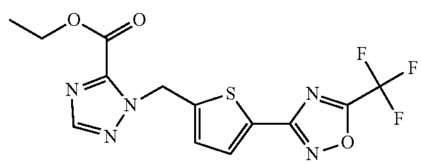 [SMILES: CCOC(=O)c1ncnn1Cc1ccc(-c2noc(C(F)(F)F)n2)s1] | 1.16 | 373 | A | |
| 1.46 | propyl 1-[[5-[5-(trifluoromethyl)-1,2,4-oxadiazol-3-yl]-2-thienyl]methyl]pyrazole-3-carboxylate | 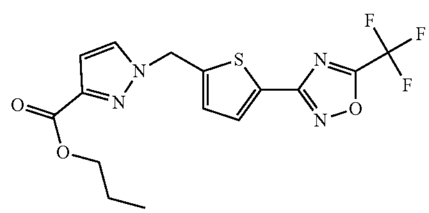 [SMILES: CCCOC(=O)c1ccn(Cc2ccc(-c3noc(C(F)(F)F)n3)s2)n1] | | | | 88-94 |
| 1.47 | propyl 2-[[5-[5-(trifluoromethyl)-1,2,4-oxadiazol-3-yl]-2-thienyl]methyl]pyrazole-3-carboxylate | 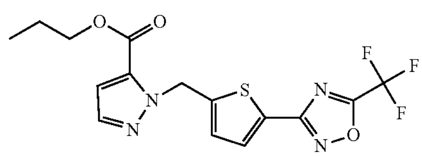 [SMILES: CCCOC(=O)c1ccnn1Cc1ccc(-c2noc(C(F)(F)F)n2)s1] | 1.22 | 387 | A | |
| 1.48 | N-methyl-2-[[5-[5-(trifluoromethyl)-1,2,4-oxadiazol-3-yl]-2-thienyl]methyl]-1,2,4-triazole-3-carboxamide | 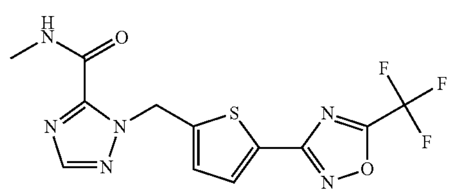 [SMILES: CNC(=O)c1ncnn1Cc1ccc(-c2noc(C(F)(F)F)n2)s1] | | | | 132-140 |
| 1.49 | N-methyl-1-[[5-[5-(trifluoromethyl)-1,2,4-oxadiazol-3-yl]-2-thienyl]methyl]-1,2,4-triazole-3-carboxamide | 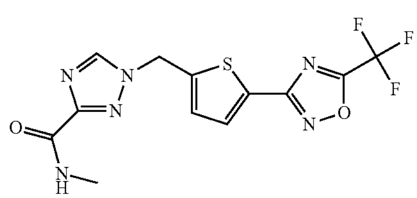 [SMILES: CNC(=O)c1ncn(Cc2ccc(-c3noc(C(F)(F)F)n3)s2)n1] | | | | 198-218 |
| 1.50 | N,N-dimethyl-2-[[5-[5-(trifluoromethyl)-1,2,4-oxadiazol-3-yl]-2-thienyl]methyl]-1,2,4-triazole-3-carboxamide | 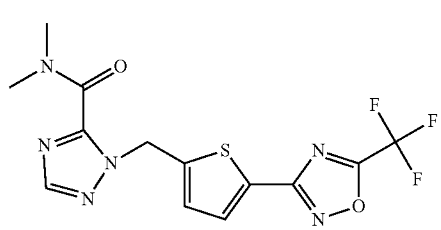 [SMILES: CN(C)C(=O)c1ncnn1Cc1ccc(-c2noc(C(F)(F)F)n2)s1] | 0.96 | 373 | A | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.51 | N-methyl-1-[[5-[5-(trifluoromethyl)-1,2,4-oxadiazol-3-yl]-2-thienyl]methyl]pyrazole-3-carboxamide | 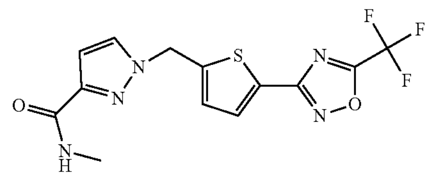 [SMILES: CNC(=O)c1ccn(Cc2ccc(-c3noc(C(F)(F)F)n3)s2)n1] | | | | 124-126 |
| 1.52 | N-methyl-2-[[5-[5-(trifluoromethyl)-1,2,4-oxadiazol-3-yl]-2-thienyl]methyl]pyrazole-3-carboxamide | 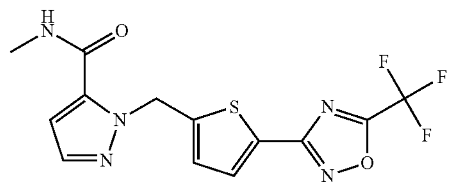 [SMILES: CNC(=O)c1ccnn1Cc1ccc(-c2noc(C(F)(F)F)n2)s1] | | | | 148-151 |
| 1.53 | methyl 1-[[5-[5-(trifluoromethyl)-1,2,4-oxadiazol-3-yl]-2-thienyl]methyl]pyrazole-3-carboxylate | 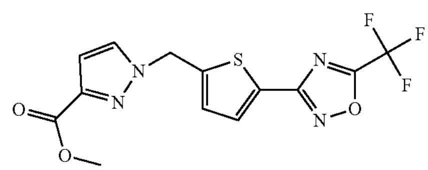 [SMILES: COC(=O)c1ccn(Cc2ccc(-c3noc(C(F)(F)F)n3)s2)n1] | 1.00 | 359 | A | |
| 1.54 | methyl 2-[[5-[5-(trifluoromethyl)-1,2,4-oxadiazol-3-yl]-2-thienyl]methyl]pyrazole-3-carboxylate | 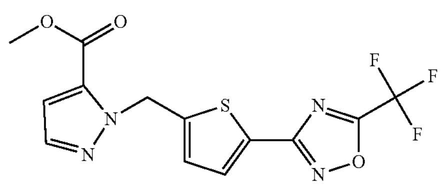 [SMILES: COC(=O)c1ccnn1Cc1ccc(-c2noc(C(F)(F)F)n2)s1] | 1.10 | 359 | A | |
| 1.55 | methyl 2-[[5-[5-(trifluoromethyl)-1,2,4-oxadiazol-3-yl]-2-thienyl]methyl]-1,2,4-triazole-3-carboxylate | 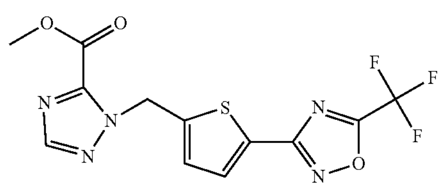 [SMILES: COC(=O)c1ncnn1Cc1ccc(-c2noc(C(F)(F)F)n2)s1] | 0.98 | 360 | A | |
| 1.56 | N-methoxy-1-[[5-[5-(trifluoromethyl)-1,2,4-oxadiazol-3-yl]-2-thienyl]methyl]pyrazole-3-carboxamide | 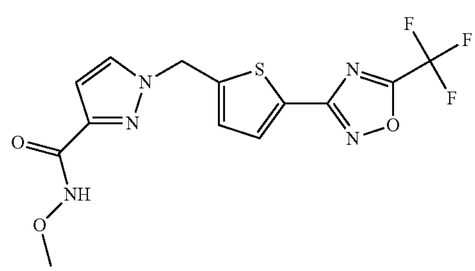 [SMILES: CONC(=O)c1ccn(Cc2ccc(-c3noc(C(F)(F)F)n3)s2)n1] | | | | 134-141 |
| 1.57 | N,N-dimethyl-1-[[5-[5-(trifluoromethyl)-1,2,4-oxadiazol-3-yl]-2-thienyl]methyl]pyrazole-3-carboxamide | 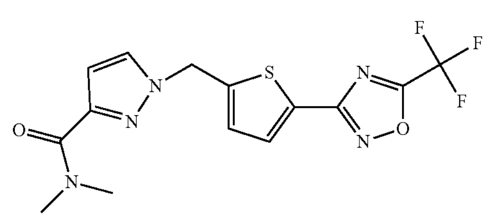 [SMILES: CN(C)C(=O)c1ccn(Cc2ccc(-c3noc(C(F)(F)F)n3)s2)n1] | | | | 90-96 |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.58 | N,N-dimethyl-2-[[5-[5-(trifluoromethyl)-1,2,4-oxadiazol-3-yl]-2-thienyl]methyl]pyrazole-3-carboxamide | 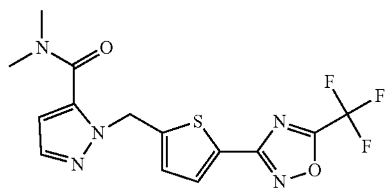 [SMILES: CN(C)C(=O)c1ccnn1Cc1ccc(-c2noc(C(F)(F)F)n2)s1] | 0.96 | 388 | A | |
| 1.59 | N-methoxy-1-[[5-[5-(trifluoromethyl)-1,2,4-oxadiazol-3-yl]-2-thienyl]methyl]-1,2,4-triazole-3-carboxamide | 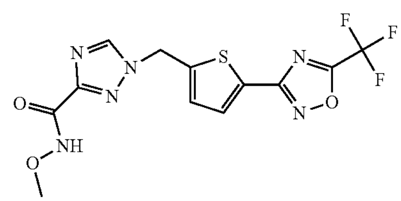 [SMILES: CONC(=O)c1ncn(Cc2ccc(-c3noc(C(F)(F)F)n3)s2)n1] | | | | 168-178 |
| 1.60 | N-methoxy-2-[[5-[5-(trifluoromethyl)-1,2,4-oxadiazol-3-yl]-2-thienyl]methyl]pyrazole-3-carboxamide | 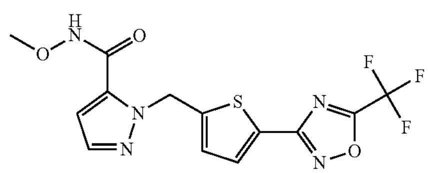 [SMILES: CONC(=O)c1ccnn1Cc1ccc(-c2noc(C(F)(F)F)n2)s1] | | | | 105-115 |
| 1.61 | N-methoxy-2-[[5-[5-(trifluoromethyl)-1,2,4-oxadiazol-3-yl]-2-thienyl]methyl]-1,2,4-triazole-3-carboxamide | 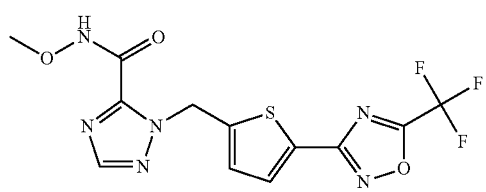 [SMILES: CONC(=O)c1ncnn1Cc1ccc(-c2noc(C(F)(F)F)n2)s1] | | | | 135-140 |
| 1.62 | 1-[[5-[5-((trifluoromethyl)-1,2,4-oxadiazol-3-yl]-2-thienyl]methyl]pyrazole-3-carboxylic acid | 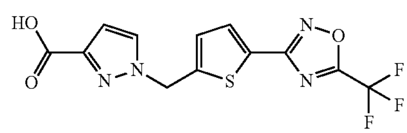 [SMILES: O=C(O)c1ccn(Cc2ccc(-c3noc(C(F)(F)F)n3)s2)n1] | | | | 140-150 |
| 1.63 | 1-[[5-[5-(trifluoromethyl)-1,2,4-oxadiazol-3-yl]-2-thienyl]methyl]-1,2,4-triazole-3-carboxylic acid | 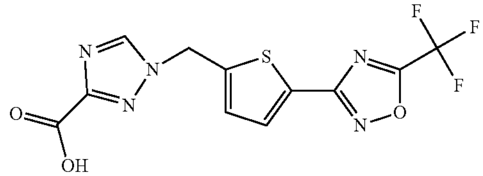 [SMILES: O=C(O)c1ncn(Cc2ccc(-c3noc(C(F)(F)F)n3)s2)n1] | | | | 210-220 |
| 1.64 | 2-[[5-[5-(trifluoromethyl)-1,2,4-oxadiazol-3-yl]-2-thienyl]methyl]pyrazole-3-carboxylic acid | 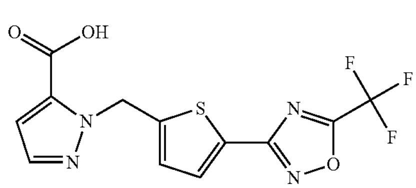 [SMILES: O=C(O)c1ccnn1Cc1ccc(-c2noc(C(F)(F)F)n2)s1] | | | | 145-165 |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.65 | N-sec-butyl-1-[1-[5-[5-(trifluoromethyl)-1,2,4-oxadiazol-3-yl]-2-thienyl]ethyl]pyrazole-4-carboxamide | 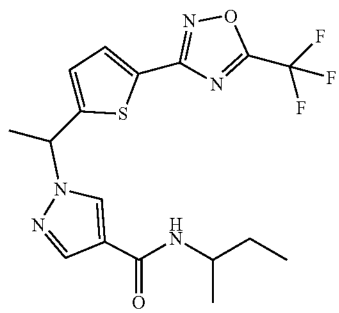 [SMILES: CCC(C)NC(=O)c1cnn(C(C)c2ccc(-c3noc(C(F)(F)F)n3)s2)c1] | 1.60 | 414.08 | B | |
| 1.66 | N-(2,2-dimethylpropyl)-1-[1-[5-[5-(trifluoromethyl)-1,2,4-oxadiazol-3-yl]-2-thienyl]ethyl]pyrazole-4-carboxamide | 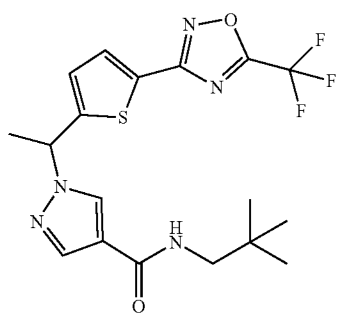 [SMILES: CC(c1ccc(-c2noc(C(F)(F)F)n2)s1)n1cc(C(=O)NCC(C)(C)C)cn1] | 1.70 | 428.09 | B | |
| 1.67 | N-isopropyl-1-[1-[5-[5-(trifluoromethyl)-1,2,4-oxadiazol-3-yl]-2-thienyl]ethyl]pyrazole-4-carboxamide | 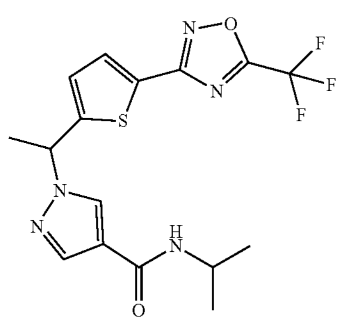 [SMILES: CC(C)NC(=O)c1cnn(C(C)c2ccc(-c3noc(C(F)(F)F)n3)s2)c1] | 1.52 | 400.06 | B | |
| 1.68 | N-methoxy-N-methyl-1-[1-[5-[5-(trifluoromethyl)-1,2,4-oxadiazol-3-yl]-2-thienyl]ethyl]pyrazole-4-carboxamide | 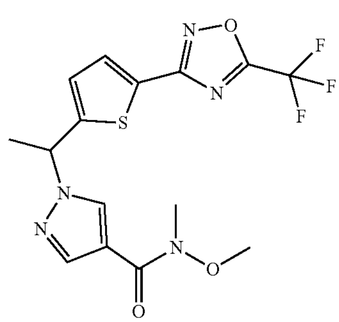 [SMILES: CON(C)C(=O)c1cnn(C(C)c2ccc(-c3noc(C(F)(F)F)n3)s2)c1] | 1.52 | 402.03 | B | |

TABLE T1-continued

Melting point (mp) data and/or retention times ($R_t$) for compounds according to Formula (I):

| Entry | Name | Rt (min) | Mass charge | Method | mp (° C.) |
|---|---|---|---|---|---|
| 1.69 | N,N-dimethyl-1-[1-[5-[5-(trifluoromethyl)-1,2,4-oxadiazol-3-yl]-2-thienyl]ethyl]pyrazole-4-carboxamide | 1.43 | 386.05 | B | |
| 1.70 | N-methyl-1-[1-[5-[5-(trifluoromethyl)-1,2,4-oxadiazol-3-yl]-2-thienyl]ethyl]pyrazole-4-carboxamide | 1.33 | 372.02 | B | |
| 1.71 | N-cyclohexyl-1-[1-[5-[5-(trifluoromethyl)-1,2,4-oxadiazol-3-yl]-2-thienyl]ethyl]pyrazole-4-carboxamide | 1.71 | 440.09 | B | |
| 1.72 | N-ethyl-1-[1-[5-[5-(trifluoromethyl)-1,2,4-oxadiazol-3-yl]-2-thienyl]ethyl]pyrazole-4-carboxamide | 1.43 | 386.05 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.73 | N-allyl-1-[1-[5-[5-(trifluoromethyl)-1,2,4-oxadiazol-3-yl]-2-thienyl]ethyl]pyrazole-4-carboxamide | 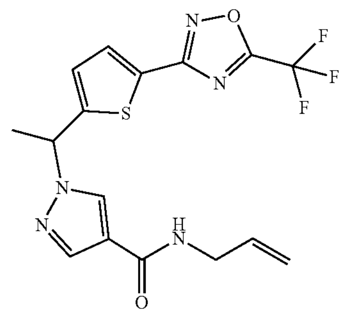 [SMILES: C=CCNC(=O)c1cnn(C(C)c2ccc(-c3noc(C(F)(F)F)n3)s2)c1] | 1.48 | 398.05 | B | |
| 1.74 | N-isobutyl-1-[1-[5-[5-(trifluoromethyl)-1,2,4-oxadiazol-3-yl]-2-thienyl]ethyl]pyrazole-4-carboxamide | 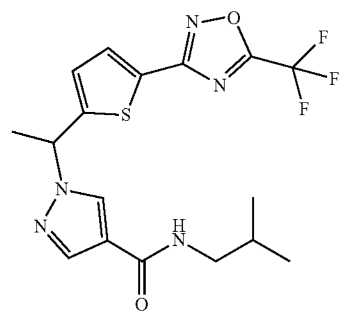 [SMILES: CC(C)CNC(=O)c1cnn(C(C)c2ccc(-c3noc(C(F)(F)F)n3)s2)c1] | 1.61 | 414.08 | B | |
| 1.75 | N-cyclopropyl-1-[1-[5-[5-(trifluoromethyl)-1,2,4-oxadiazol-3-yl]-2-thienyl]ethyl]pyrazole-4-carboxamide | 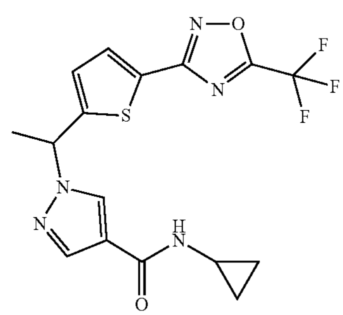 [SMILES: CC(c1ccc(-c2noc(C(F)(F)F)n2)s1)n1cc(C(=O)NC2CC2)cn1] | 1.44 | 398.05 | B | |
| 1.76 | N,N-diethyl-1-[1-[5-[5-(trifluoromethyl)-1,2,4-oxadiazol-3-yl]-2-thienyl]ethyl]pyrazole-4-carboxamide | 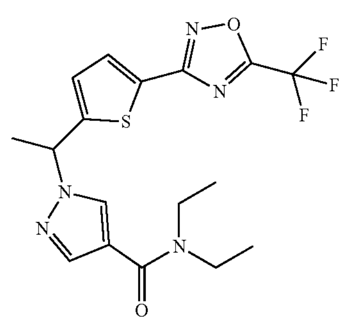 [SMILES: CCN(CC)C(=O)c1cnn(C(C)c2ccc(-c3noc(C(F)(F)F)n3)s2)c1] | 1.61 | 414.09 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.77 | N-phenyl-1-[1-[5-[5-(trifluoromethyl)-1,2,4-oxadiazol-3-yl]-2-thienyl]ethyl]pyrazole-4-carboxamide | 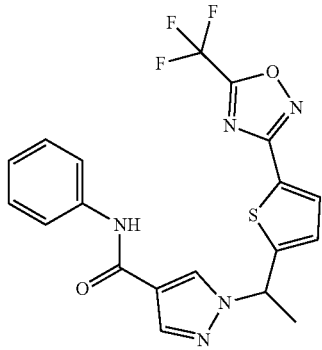 [SMILES: CC(c1ccc(-c2noc(C(F)(F)F)n2)s1)n1cc(C(=O)Nc2ccccc2)cn1] | 1.69 | 434.05 | B | |
| 1.78 | N-benzyl-1-[1-[5-[5-(trifluoromethyl)-1,2,4-oxadiazol-3-yl]-2-thienyl]ethyl]pyrazole-4-carboxamide | 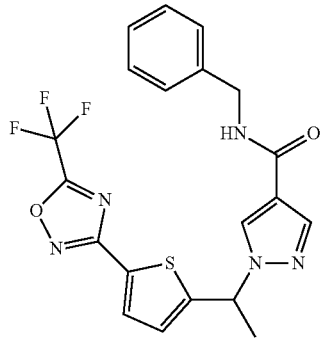 [SMILES: CC(c1ccc(-c2noc(C(F)(F)F)n2)s1)n1cc(C(=O)NCc2ccccc2)cn1] | 1.65 | 448.07 | B | |
| 1.79 | N-cyclobutyl-1-[1-[5-[5-(trifluoromethyl)-1,2,4-oxadiazol-3-yl]-2-thienyl]ethyl]pyrazole-4-carboxamide | 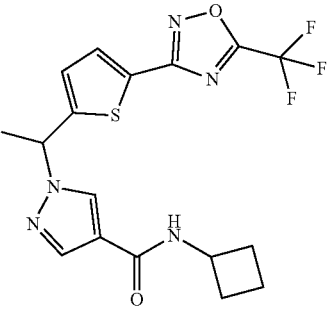 [SMILES: CC(c1ccc(-c2noc(C(F)(F)F)n2)s1)n1cc(C(=O)NC2CCC2)cn1] | 1.57 | 412.07 | B | |
| 1.80 | N-ethoxy-1-[1-[5-[5-(trifluoromethyl)-1,2,4-oxadiazol-3-yl]-2-thienyl]ethyl]pyrazole-4-carboxamide | 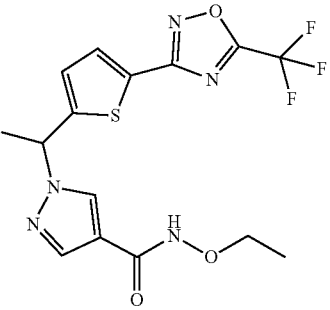 [SMILES: CCONC(=O)c1cnn(C(C)c2ccc(-c3noc(C(F)(F)F)n3)s2)c1] | 1.42 | 402.05 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.81 | N-propyl-1-[1-[5-[5-(trifluoromethyl)-1,2,4-oxadiazol-3-yl]-2-thienyl]ethyl]pyrazole-4-carboxamide | 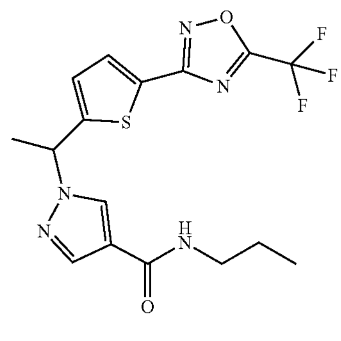 [SMILES: CCCNC(=O)c1cnn(C(C)c2ccc(-c3noc(C(F)(F)F)n3)s2)c1] | 1.52 | 400.07 | B | |
| 1.82 | N-methoxy-1-[1-[5-[5-(trifluoromethyl)-1,2,4-oxadiazol-3-yl]-2-thienyl]ethyl]pyrazole-4-carboxamide | 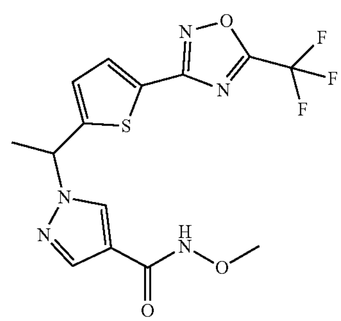 [SMILES: CONC(=O)c1cnn(C(C)c2ccc(-c3noc(C(F)(F)F)n3)s2)c1] | 1.35 | 388.04 | B | |
| 1.83 | N-cyclopentyl-1-[1-[5-[5-(trifluoromethyl)-1,2,4-oxadiazol-3-yl]-2-thienyl]ethyl]pyrazole-4-carboxamide | 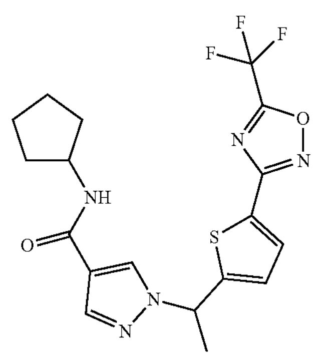 [SMILES: CC(c1ccc(-c2noc(C(F)(F)F)n2)s1)n1cc(C(=O)NC2CCCC2)cn1] | 1.64 | 426.08 | B | |
| 1.84 | morpholino-1-[1-[5-[5-(trifluoromethyl)-1,2,4-oxadiazol-3-yl]-2-thienyl]ethyl]pyrazol-4-yl]methanone | 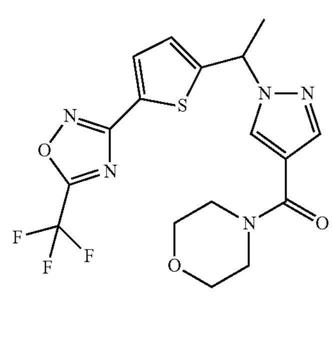 [SMILES: CC(c1ccc(-c2noc(C(F)(F)F)n2)s1)n1cc(C(=O)N2CCOCC2)cn1] | 1.42 | 428.06 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.85 | N-(2-furylmethyl)-1-[1-[5-[5-(trifluoromethyl)-1,2,4-oxadiazol-3-yl]-2-thienyl]ethyl]pyrazole-4-carboxamide | 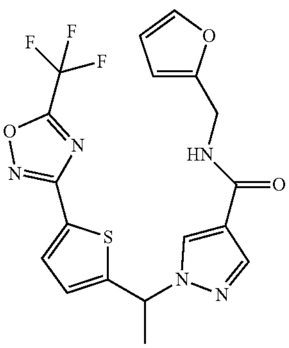 [SMILES: CC(c1ccc(-c2noc(C(F)(F)F)n2)s1)n1cc(C(=O)NCc2ccco2)cn1] | 1.55 | 438.04 | B | |
| 1.86 | N-tert-butyl-1-[1-[5-[5-(trifluoromethyl)-1,2,4-oxadiazol-3-yl]-2-thienyl]ethyl]pyrazole-4-carboxamide | 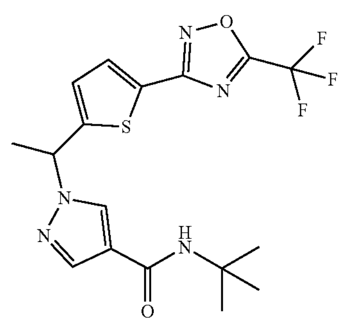 [SMILES: CC(c1ccc(-c2noc(C(F)(F)F)n2)s1)n1cc(C(=O)NC(C)(C)C)cn1] | 1.66 | 414.07 | B | |
| 1.87 | N-prop-2-ynyl-1-[1-[5-[5-(trifluoromethyl)-1,2,4-oxadiazol-3-yl]-2-thienyl]ethyl]pyrazole-4-carboxamide | 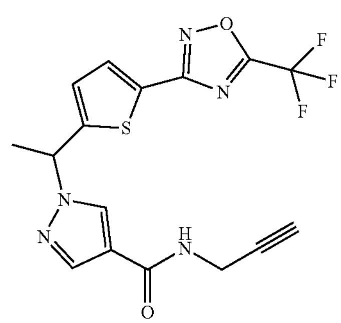 [SMILES: C#CCNC(=O)c1cnn(C(C)c2ccc(-c3noc(C(F)(F)F)n3)s2)c1] | 1.43 | 396.01 | B | |
| 1.88 | N-ethyl-N-methyl-1-[1-[5-[5-(trifluoromethyl)-1,2,4-oxadiazol-3-yl]-2-thienyl]ethyl]pyrazole-4-carboxamide | 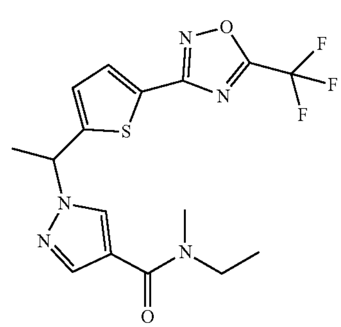 [SMILES: CCN(C)C(=O)c1cnn(C(C)c2ccc(-c3noc(C(F)(F)F)n3)s2)c1] | 1.52 | 400.05 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.89 | N-phenyl-1-[[5-[5-(trifluoromethyl)-1,2,4-oxadiazol-3-yl]-2-thienyl]methyl]-1,2,4-triazole-3-carboxamide | 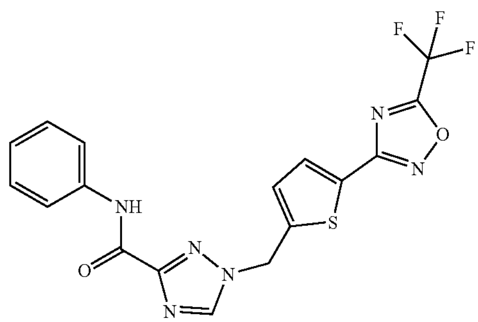 [SMILES: O=C(Nc1ccccc1)c1ncn(Cc2ccc(-c3noc(C(F)(F)F)n3)s2)n1] | 1.56 | 421.00 | B | |
| 1.90 | N-benzyl-1-[[5-[5-(trifluoromethyl)-1,2,4-oxadiazol-3-yl]-2-thienyl]methyl]-1,2,4-triazole-3-carboxamide | 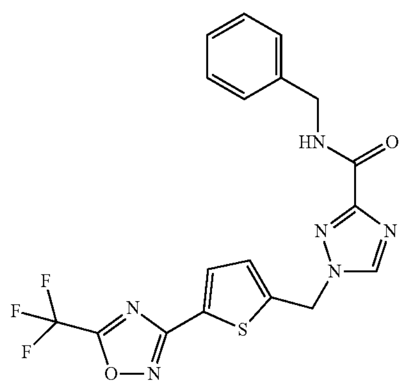 [SMILES: O=C(NCc1ccccc1)c1ncn(Cc2ccc(-c3noc(C(F)(F)F)n3)s2)n1] | 1.55 | 435.01 | B | |
| 1.91 | N-cyclobutyl-1-[[5-[5-(trifluoromethyl)-1,2,4-oxadiazol-3-yl]-2-thienyl]methyl]-1,2,4-triazole-3-carboxamide | 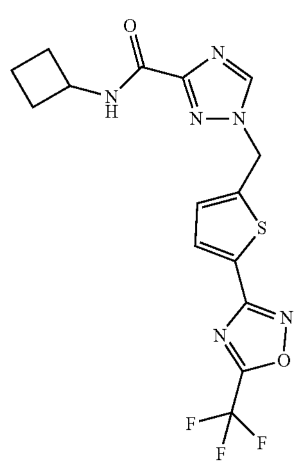 [SMILES: O=C(NC1CCC1)c1ncn(Cc2ccc(-c3noc(C(F)(F)F)n3)s2)n1] | 1.46 | 398.99 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.92 | N-ethoxy-1-[[5-[5-(trifluoromethyl)-1,2,4-oxadiazol-3-yl]-2-thienyl]methyl]-1,2,4-triazole-3-carboxamide | 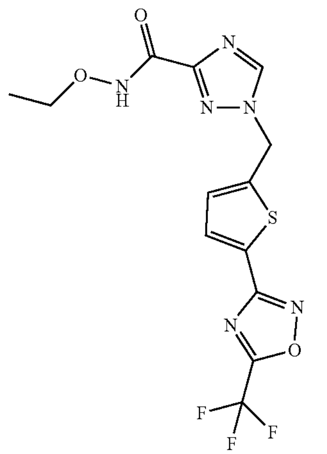 | 1.24 | 388.96 | B | |
| 1.93 | N-propyl-1-[[5-[5-(trifluoromethyl)-1,2,4-oxadiazol-3-yl]-2-thienyl]methyl]-1,2,4-triazole-3-carboxamide | 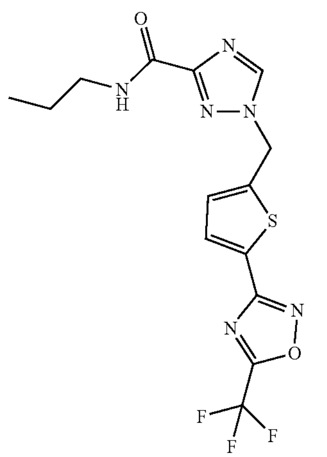 [SMILES: CCCNC(=O)c1ncn(Cc2ccc(-c3noc(C(F)(F)F)n3)s2)n1] | 1.41 | 386.99 | B | |
| 1.94 | N-cyclopentyl-1-[[5-[5-(trifluoromethyl)-1,2,4-oxadiazol-3-yl]-2-thienyl]methyl]-1,2,4-triazole-3-carboxamide | 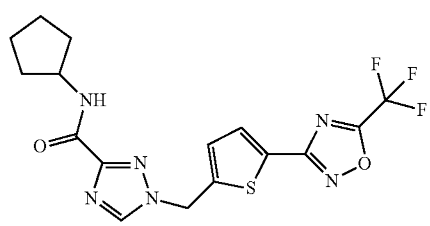 [SMILES: O=C(NC1CCCC1)c1ncn(Cc2ccc(-c3noc(C(F)(F)F)n3)s2)n1] | 1.54 | 413.02 | B | |
| 1.95 | morpholino-1-[[5-[5-(trifluoromethyl)-1,2,4-oxadiazol-3-yl]-2-thienyl]methyl]-1,2,4-triazol-3-yl]methanone | 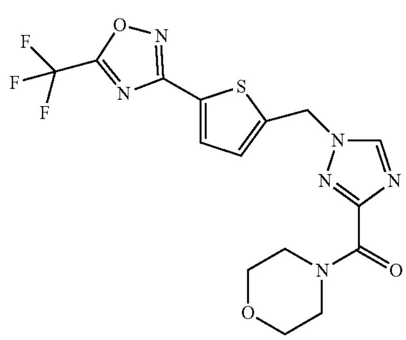 [SMILES: O=C(c1ncn(Cc2ccc(-c3noc(C(F)(F)F)n3)s2)n1)N1CCOCC1] | 1.27 | 414.99 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.96 | N-(2-furylmethyl)-1-[[5-[5-(trifluoromethyl)-1,2,4-oxadiazol-3-yl]-2-thienyl]methyl]-1,2,4-triazole-3-carboxamide | 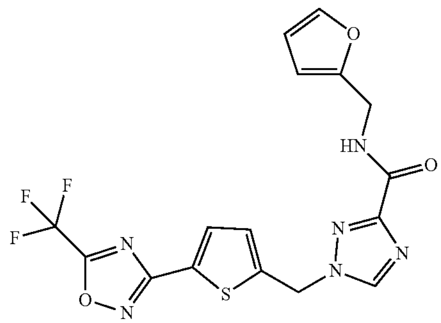 [SMILES: O=C(NCc1ccco1)c1ncn(Cc2ccc(-c3noc(C(F)(F)F)n3)s2)n1] | 1.42 | 424.99 | B | |
| 1.97 | N-tert-butyl-1-[[5-[5-(trifluoromethyl)-1,2,4-oxadiazol-3-yl]-2-thienyl]methyl]-1,2,4-triazole-3-carboxamide | 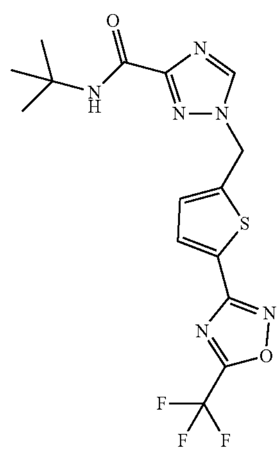 [SMILES: CC(C)(C)NC(=O)c1ncn(Cc2ccc(-c3noc(C(F)(F)F)n3)s2)n1] | 1.54 | 401.01 | B | |
| 1.98 | N-prop-2-ynyl-1-[[5-[5-(trifluoromethyl)-1,2,4-oxadiazol-3-yl]-2-thienyl]methyl]-1,2,4-triazole-3-carboxamide | 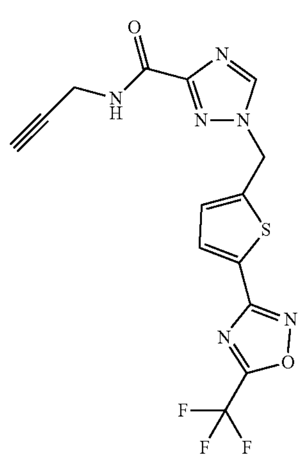 [SMILES: C#CCNC(=O)c1ncn(Cc2ccc(-c3noc(C(F)(F)F)n3)s2)n1] | 1.28 | 382.96 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.99 | N-ethyl-N-methyl-1-[[5-[5-(trifluoromethyl)-1,2,4-oxadiazol-3-yl]-2-thienyl]methyl]-1,2,4-triazole-3-carboxamide | 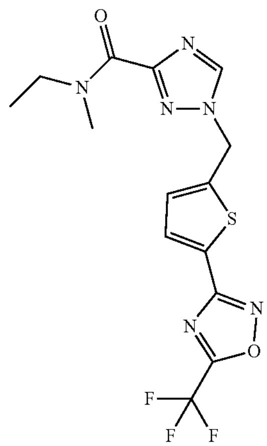 [SMILES: CCN(C)C(=O)c1ncn(Cc2ccc(-c3noc(C(F)(F)F)n3)s2)n1] | 1.38 | 386.99 | B | |
| 1.100 | N-sec-butyl-1-1-[[5-[5-(trifluoromethyl)-1,2,4-oxadiazol-3-yl]-2-thienyl]methyl]pyrazole-4-carboxamide | 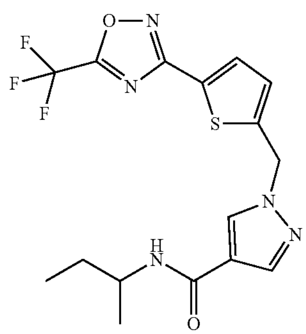 [SMILES: CCC(C)NC(=O)c1cnn(Cc2ccc(-c3noc(C(F)(F)F)n3)s2)c1] | 1.52 | 400.02 | B | |
| 1.101 | N-(2,2-dimethylpropyl)-1-[[5-[5-(trifluoromethyl)-1,2,4-oxadiazol-3-yl]-2-thienyl]methyl]pyrazole-4-carboxamide | 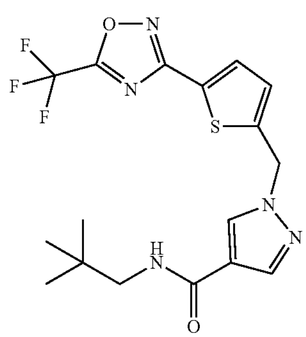 [SMILES: CC(C)(C)CNC(=O)c1cnn(Cc2ccc(-c3noc(C(F)(F)F)n3)s2)c1] | 1.63 | 414.03 | B | |
| 1.102 | N-isopropyl-1-[[5-[5-(trifluoromethyl)-1,2,4-oxadiazol-3-yl]-2-thienyl]methyl]pyrazole-4-carboxamide | 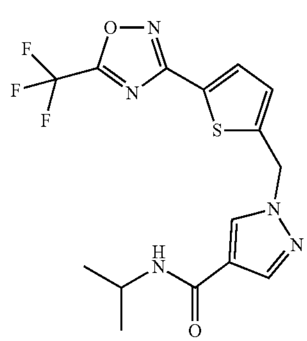 [SMILES: CC(C)NC(=O)c1cnn(Cc2ccc(-c3noc(C(F)(F)F)n3)s2)c1] | 1.44 | 385.99 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.103 | N-methoxy-N-methyl-1-[[5-[5-(trifluoromethyl)-1,2,4-oxadiazol-3-yl]-2-thienyl]methyl]pyrazole-4-carboxamide | 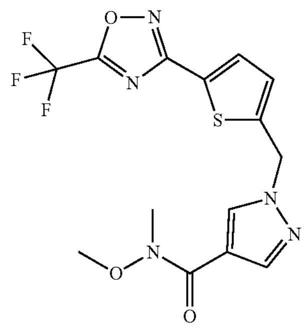 [SMILES: CON(C)C(=O)c1cnn(Cc2ccc(-c3noc(C(F)(F)F)n3)s2)c1] | 1.43 | 387.97 | B | |
| 1.104 | N,N-dimethyl-1-[[5-[5-(trifluoromethyl)-1,2,4-oxadiazd-3-yl]-2-thienyl]methyl]pyrazole-4-carboxamide | 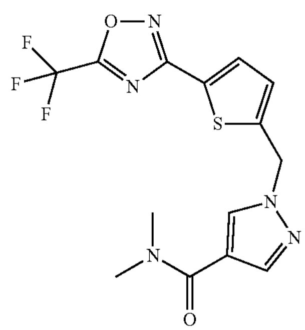 [SMILES: CN(C)C(=O)c1cnn(Cc2ccc(-c3noc(C(F)(F)F)n3)s2)c1] | 1.34 | 371.97 | B | |
| 1.105 | N-cyclohexyl-1-[[5-[5-(trifluoromethyl)-1,2,4-oxadiazol-3-yl]-2-thienyl]methyl]pyrazole-4-carboxamide | 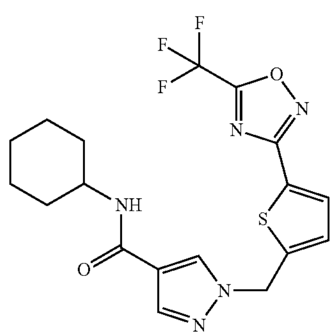 [SMILES: O=C(NC1CCCCC1)c1cnn(Cc2ccc(-c3noc(C(F)(F)F)n3)s2)c1] | 1.65 | 426.04 | B | |
| 1.106 | N-ethyl-1-[[5-[5-(trifluoromethyl)-1,2,4-oxadiazol-3-yl]-2-thienyl]methyl]pyrazole-4-carboxamide | 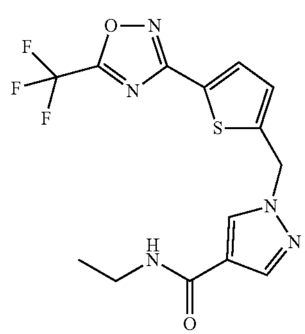 [SMILES: CCNC(=O)c1cnn(Cc2ccc(-c3noc(C(F)(F)F)n3)s2)c1] | 1.34 | 371.97 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.107 | N-allyl-1-[[5-[5-(trifluoromethyl)-1,2,4-oxadiazol-3-yl]-2-thienyl]methyl]pyrazole-4-carboxamide | 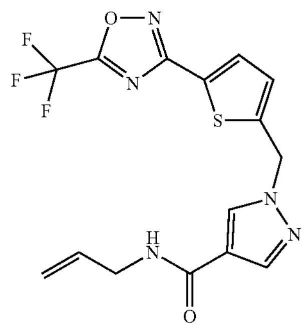 [SMILES: C=CCNC(=O)c1cnn(Cc2ccc(-c3noc(C(F)(F)F)n3)s2)c1] | 1.39 | 383.97 | B | |
| 1.108 | N-sec-butyl-1-[[5-[5-(trifluoromethyl)-1,2,4-oxadiazol-3-yl]-2-thienyl]methyl]pyrazole-3-carboxamide | 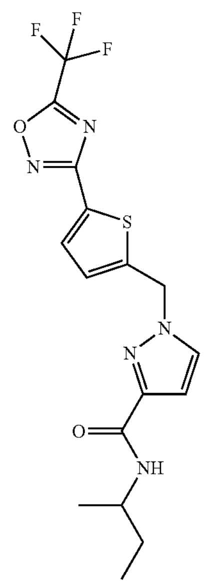 [SMILES: CCC(C)NC(=O)c1ccn(Cc2ccc(-c3noc(C(F)(F)F)n3)s2)n1] | 1.66 | 400.02 | B | |
| 1.109 | N-isobutyl-1-[[5-[5-(trifluoromethyl)-1,2,4-oxadiazol-3-yl]-2-thienyl]methyl]pyrazole-4-carboxamide | 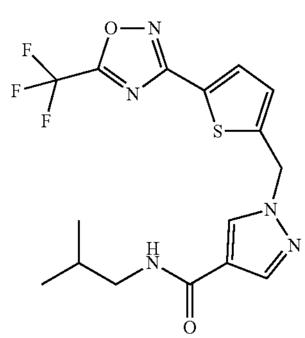 [SMILES: CC(C)CNC(=O)c1cnn(Cc2ccc(-c3noc(C(F)(F)F)n3)s2)c1] | 1.52 | 400.01 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.110 | N-(2,2-dimethylpropyl)-1-[[5-[5-(trifluoromethyl)-1,2,4-oxadiazol-3-yl]-2-thienyl]methyl]pyrazole-3-carboxamide | 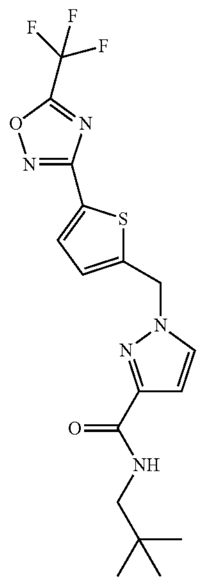 [SMILES: CC(C)(C)CNC(=O)c1ccn(Cc2ccc(-c3noc(C(F)(F)F)n3)s2)n1] | 1.76 | 414.04 | B | |
| 1.111 | N-cyclopropyl-1-[[5-[5-(trifluoromethyl)-1,2,4-oxadiazol-3-yl]-2-thienyl]methyl]pyrazole-4-carboxamide | 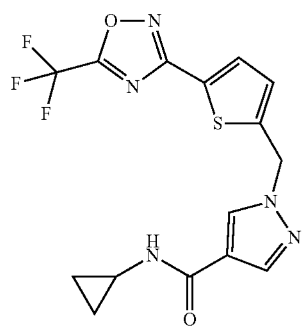 [SMILES: O=C(NC1CC1)c1cnn(Cc2ccc(-c3noc(C(F)(F)F)n3)s2)c1] | 1.36 | 383.97 | B | |
| 1.112 | N-isopropyl-1-[[5-[5-(trifluoromethyl)-1,2,4-oxadiazol-3-yl]-2-thienyl]methyl]pyrazole-3-carboxamide | 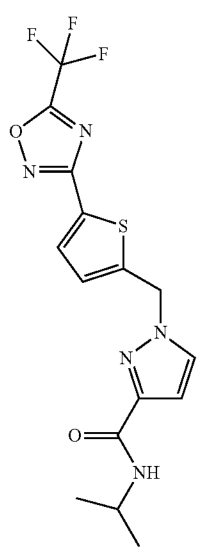 [SMILES: CC(C)NC(=O)c1ccn(Cc2ccc(-c3noc(C(F)(F)F)n3)s2)n1] | 1.57 | 386.00 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.113 | N,N-diethyl-1-[[5-[5-(trifluoromethyl)-1,2,4-oxadiazol-3-yl]-2-thienyl]methyl]pyrazole-4-carboxamide | 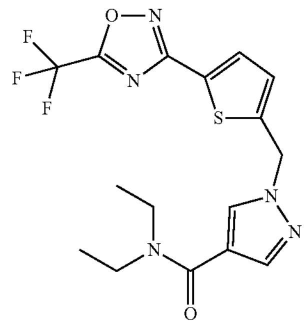 [SMILES: CCN(CC)C(=O)c1cnn(Cc2ccc(-c3noc(C(F)(F)F)n3)s2)c1] | 1.58 | 400.01 | B | |
| 1.114 | N-methoxy-N-methyl-1-[[5-[5-(trifluoromethyl)-1,2,4-oxadiazol-3-yl]-2-thienyl]methyl]pyrazole-3-carboxamide | 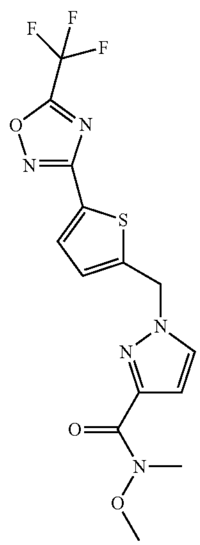 [SMILES: CON(C)C(=O)c1ccn(Cc2ccc(-c3noc(C(F)(F)F)n3)s2)n1] | 1.45 | 387.97 | B | |
| 1.115 | N-phenyl-1-[[5-[5-(trifluoromethyl)-1,2,4-oxadiazol-3-yl]-2-thienyl]methyl]pyrazole-4-carboxamide | 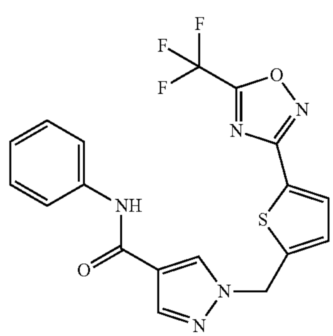 [SMILES: O=C(Nc1ccccc1)c1cnn(Cc2ccc(-c3noc(C(F)(F)F)n3)s2)c1] | 1.61 | 420.00 | B | |
| 1.116 | N-benzyl-1-[[5-[5-(trifluoromethyl)-1,2,4-oxadiazol-3-yl]-2-thienyl]methyl]pyrazole-4-carboxamide | 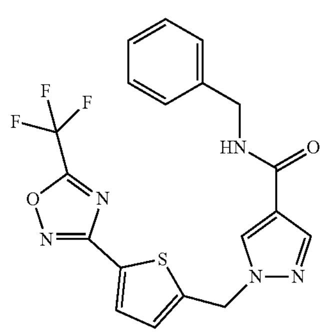 [SMILES: O=C(NCc1ccccc1)c1cnn(Cc2ccc(-c3noc(C(F)(F)F)n3)s2)c1] | 1.55 | 434.01 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.117 | N-cyclobutyl-1-[[5-[5-(trifluoromethyl)-1,2,4-oxadiazol-3-yl]-2-thienyl]methyl]pyrazole-4-carboxamide | 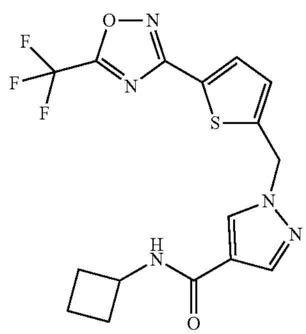 [SMILES: O=C(NC1CCC1)c1cnn(Cc2ccc(-c3noc(C(F)(F)F)n3)s2)c1] | 1.49 | 398.00 | B | |
| 1.118 | N-cyclohexyl-1-[[5-[5-(trifluoromethyl)-1,2,4-oxadiazol-3-yl]-2-thienyl]methyl]pyrazole-3-carboxamide | 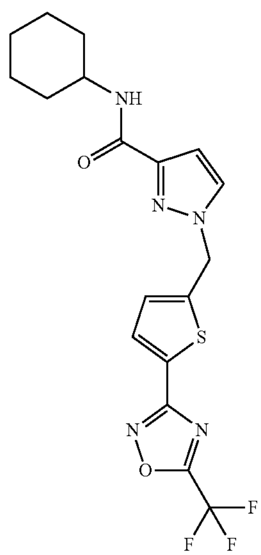 [SMILES: O=C(NC1CCCCC1)c1ccn(Cc2ccc(-c3noc(C(F)(F)F)n3)s2)n1] | 1.80 | 426.05 | B | |
| 1.119 | N-ethoxy-1-[[5-[5-(trifluoromethyl)-1,2,4-oxadiazol-3-yl]-2-thienyl]methyl]pyrazole-4-carboxamide | 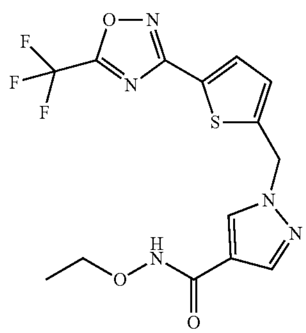 [SMILES: CCONC(=O)c1cnn(Cc2ccc(-c3noc(C(F)(F)F)n3)s2)c1] | 1.33 | 387.97 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.120 | N-ethyl-1-[[5-[5-(trifluoromethyl)-1,2,4-oxadiazol-3-yl]-2-thienyl]methyl]pyrazole-3-carboxamide | 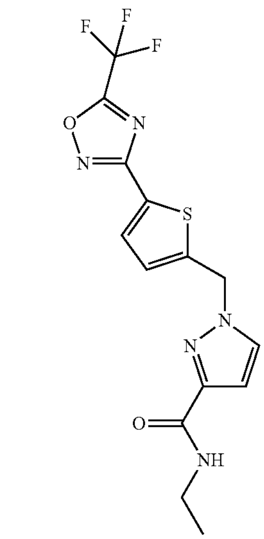 [SMILES: CCNC(=O)c1ccn(Cc2ccc(-c3noc(C(F)(F)F)n3)s2)n1] | 1.46 | 371.97 | B | |
| 1.121 | N-propyl-1-[[5-[5-(trifluoromethyl)-1,2,4-oxadiazol-3-yl]-2-thienyl]methyl]pyrazole-4-carboxamide | 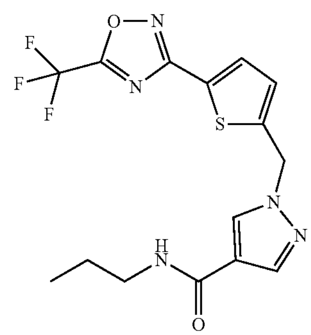 [SMILES: CCCNC(=O)c1cnn(Cc2ccc(-c3noc(C(F)(F)F)n3)s2)c1] | 1.44 | 385.99 | B | |
| 1.122 | N-allyl-1-[[5-[5-(trifluoromethyl)-1,2,4-oxadiazol-3-yl]-2-thienyl]methyl]pyrazole-3-carboxamide | 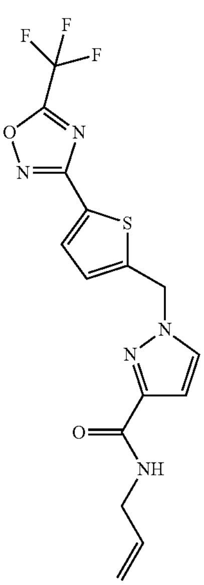 [SMILES: C=CCNC(=O)c1ccn(Cc2ccc(-c3noc(C(F)(F)F)n3)s2)n1] | 1.52 | 383.97 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.123 | N-methoxy-1-[[5-[5-(trifluoromethyl)-1,2,4-oxadiazol-3-yl]-2-thienyl]methyl]pyrazole-4-carboxamide | 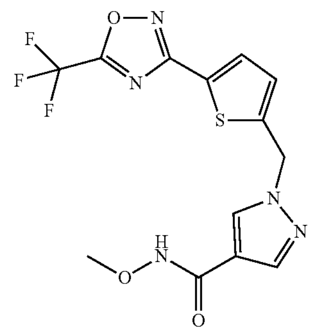 [SMILES: CONC(=O)c1cnn(Cc2ccc(-c3noc(C(F)(F)F)n3)s2)c1] | 1.25 | 373.94 | B | |
| 1.124 | N-isobutyl-1-[[5-[5-(trifluoromethyl)-1,2,4-oxadiazol-3-yl]-2-thienyl]methyl]pyrazole-3-carboxamide | 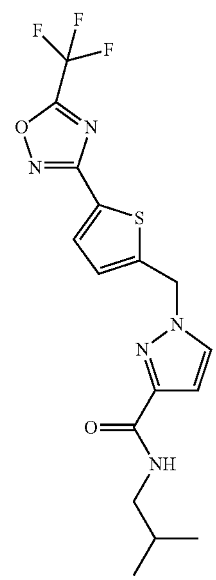 [SMILES: CC(C)CNC(=O)c1ccn(Cc2ccc(-c3noc(C(F)(F)F)n3)s2)n1] | 1.67 | 400.01 | B | |
| 1.125 | N-cyclopentyl-1-[[5-[5-(trifluoromethyl)-1,2,4-oxadiazol-3-yl]-2-thienyl]methyl]pyrazole-4-carboxamide | 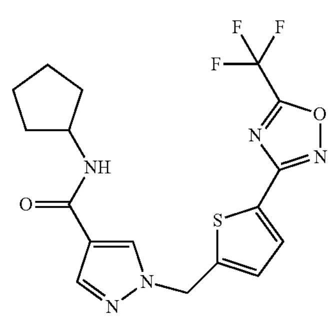 [SMILES: O=C(NC1CCCC1)c1cnn(Cc2ccc(-c3noc(C(F)(F)F)n3)s2)c1] | 1.54 | 412.02 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.126 | N-cyclopropyl-1-[[5-[5-(trifluoromethyl)-1,2,4-oxadiazol-3-yl]-2-thienyl]methyl]pyrazole-3-carboxamide | 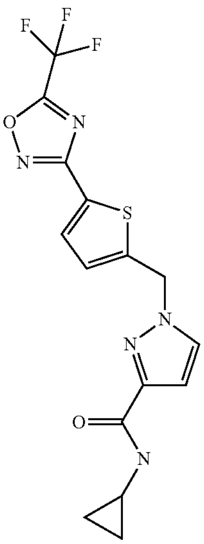 [SMILES: O=C(NC1CC1)c1ccn(Cc2ccc(-c3noc(C(F)(F)F)n3)s2)n1] | 1.47 | 383.97 | B | |
| 1.127 | morpholino-1-[[5-[5-(trifluoromethyl)-1,2,4-oxadiazol-3-yl]-2-thienyl]methyl]pyrazol-4-yl]methanone | 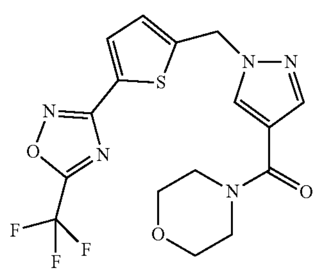 [SMILES: O=C(c1cnn(Cc2ccc(-c3noc(C(F)(F)F)n3)s2)c1)N1CCOCC1] | 1.33 | 414.00 | B | |
| 1.128 | N,N-diethyl-1-[[5-[5-(trifluoromethyl)-1,2,4-oxadiazol-3-yl]-2-thienyl]methyl]pyrazole-3-carboxamide | 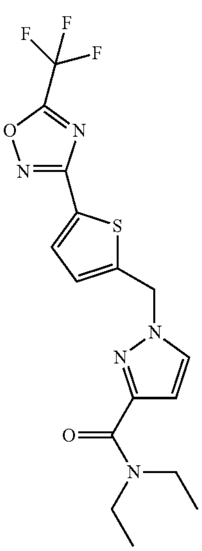 [SMILES: CCN(CC)C(=O)c1ccn(Cc2ccc(-c3noc(C(F)(F)F)n3)s2)n1] | 1.66 | 400.02 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.129 | N-(2-furylmethyl)-1-[[5-[5-(trifluoromethyl)-1,2,4-oxadiazol-3-yl]-2-thienyl]methyl]pyrazole-4-carboxamide | 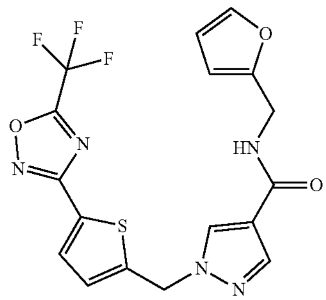 [SMILES: O=C(NCc1ccco1)c1cnn(Cc2ccc(-c3noc(C(F)(F)F)n3)s2)c1] | 1.47 | 423.98 | B | |
| 1.130 | N-phenyl-1-[[5-[5-(trifluoromethyl)-1,2,4-oxadiazol-3-yl]-2-thienyl]methyl]pyrazole-3-carboxamide | 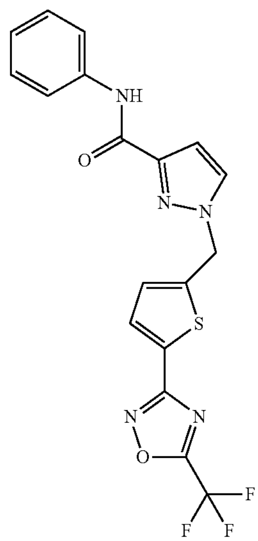 [SMILES: O=C(Nc1ccccc1)c1ccn(Cc2ccc(-c3noc(C(F)(F)F)n3)s2)n1] | 1.75 | 420.00 | B | |
| 1.131 | N-tert-butyl-1-[[5-[5-(trifluoromethyl)-1,2,4-oxadiazol-3-yl]-2-thienyl]methyl]pyrazole-4-carboxamide | 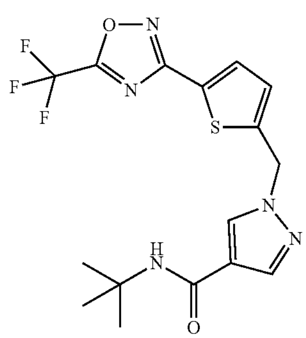 [SMILES: CC(C)(C)NC(=O)c1cnn(Cc2ccc(-c3noc(C(F)(F)F)n3)s2)c1] | 1.58 | 400.01 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.132 | N-benzyl-1-[[5-[5-(trifluoromethyl)-1,2,4-oxadiazol-3-yl]-2-thienyl]methyl]pyrazole-3-carboxamide | 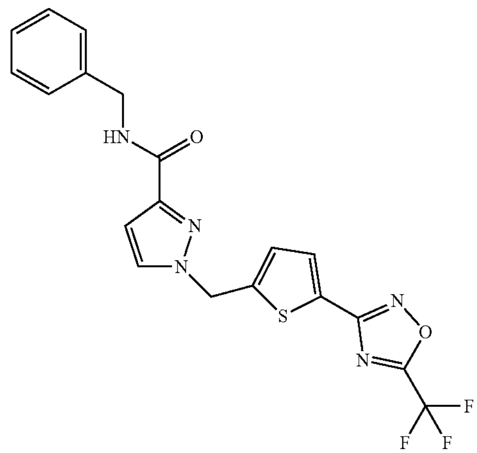 [SMILES: O=C(NCc1ccccc1)c1ccn(Cc2ccc(-c3noc(C(F)(F)F)n3)s2)n1] | 1.69 | 434.02 | B | |
| 1.133 | N-prop-2-ynyl-1-[[5-[5-(trifluoromethyl)-1,2,4-oxadiazol-3-yl]-2-thienyl]methyl]pyrazole-4-carboxamide | 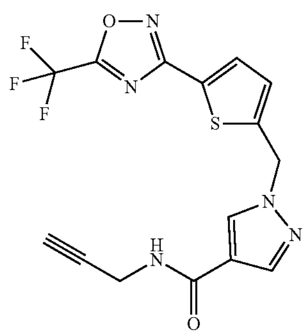 [SMILES: C#CCNC(=O)c1cnn(Cc2ccc(-c3noc(C(F)(F)F)n3)s2)c1] | 1.34 | 381.96 | B | |
| 1.134 | N-cyclobutyl-1-[[5-[5-(trifluoromethyl)-1,2,4-oxadiazol-3-yl]-2-thienyl]methyl]pyrazole-3-carboxamide | 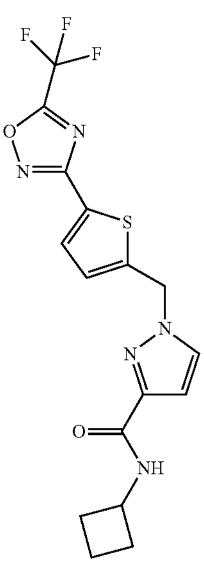 [SMILES: O=C(NC1CCC1)c1ccn(Cc2ccc(-c3noc(C(F)(F)F)n3)s2)n1] | 1.62 | 397.99 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.135 | N-ethyl-N-methyl-1-[[5-[5-(trifluoromethyl)-1,2,4-oxadiazol-3-yl]-2-thienyl]methyl]pyrazole-4-carboxamide | 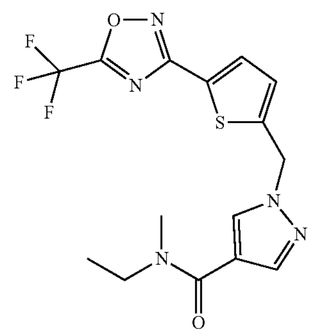 [SMILES: CCN(C)C(=O)c1cnn(Cc2ccc(-c3noc(C(F)(F)F)n3)s2)c1] | 1.43 | 385.99 | B | |
| 1.136 | N-ethoxy-1-[[5-[5-(trifluoromethyl)-1,2,4-oxadiazol-3-yl]-2-thienyl]methyl]pyrazole-3-carboxamide | 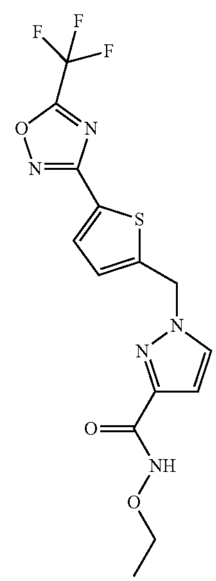 [SMILES: CCONC(=O)c1ccn(Cc2ccc(-c3noc(C(F)(F)F)n3)s2)n1] | 1.40 | 387.98 | B | |
| 1.137 | N-propyl-1-[[5-[5-(trifluoromethyl)-1,2,4-oxadiazol-3-yl]-2-thienyl]methyl]pyrazole-3-carboxamide | 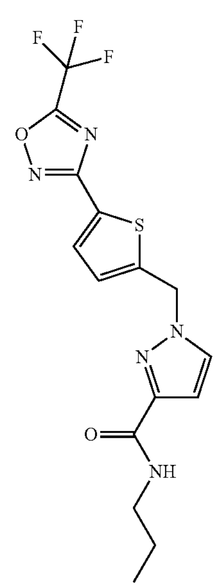 [SMILES: CCCNC(=O)c1ccn(Cc2ccc(-c3noc(C(F)(F)F)n3)s2)n1] | 1.57 | 386.00 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.138 | N-cyclopentyl-1-[[5-[5-(trifluoromethyl)-1,2,4-oxadiazol-3-yl]-2-thienyl]methyl]pyrazole-3-carboxamide | 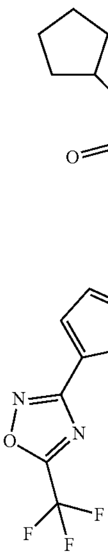 | 1.59 | 424.00 | B | |
| 1.139 | morpholino-[1-[[5-[5-(trifluoromethyl)-1,2,4-oxadiazol-3-yl]-2-thienyl]methyl]pyrazol-3-yl]methanone | 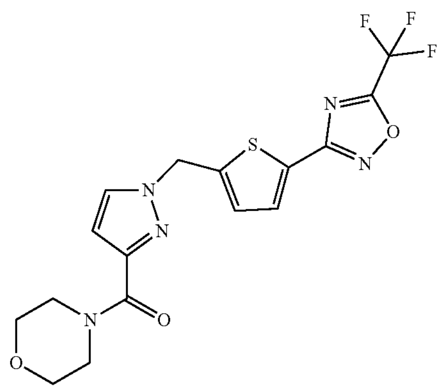 [SMILES: O=C(c1ccn(Cc2ccc(-c3noc(C(F)(F)F)n3)s2)n1)N1CCOCC1] | 1.73 | 400.01 | B | |
| 1.140 | N-(2-furylmethyl)-1-[[5-[5-(trifluoromethyl)-1,2,4-oxadiazol-3-yl]-2-thienyl]methyl]pyrazole-3-carboxamide | 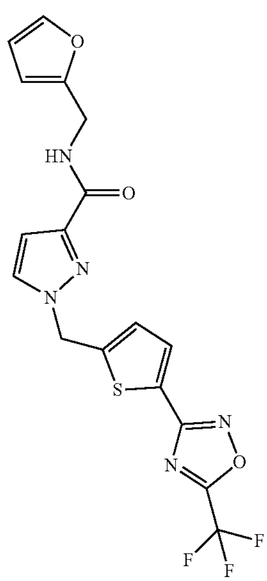 [SMILES: O=C(NCc1ccco1)c1ccn(Cc2ccc(-c3noc(C(F)(F)F)n3)s2)n1] | 1.45 | 381.96 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.141 | N-tert-butyl-1-[[5-[5-(trifluoromethyl)-1,2,4-oxadiazol-3-yl]-2-thienyl]methyl]pyrazole-3-carboxamide | 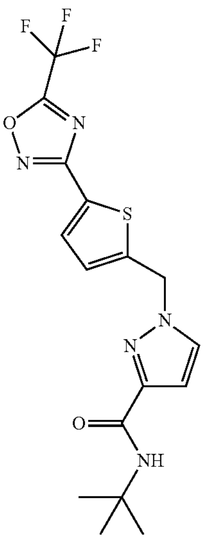 [SMILES: CC(C)(C)NC(=O)c1ccn(Cc2ccc(-c3noc(C(F)(F)F)n3)s2)n1] | 1.59 | 424.00 | B | |
| 1.142 | N-prop-2-ynyl-1-[[5-[5-(trifluoromethyl)-1,2,4-oxadiazol-3-yl]-2-thienyl]methyl]pyrazole-3-carboxamide | 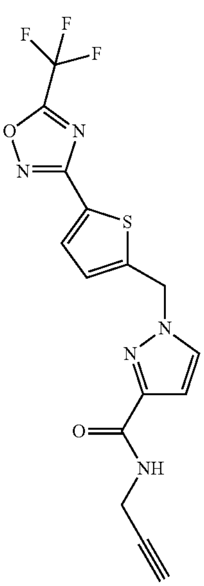 [SMILES: C#CCNC(=O)c1ccn(Cc2ccc(-c3noc(C(F)(F)F)n3)s2)n1] | 1.73 | 400.01 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.143 | N-ethyl-N-methyl-1-[[5-[5-(trifluoromethyl)-1,2,4-oxadiazol-3-yl]-2-thienyl]methyl]pyrazole-3-carboxamide | 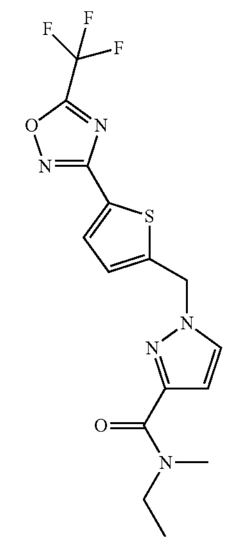 [SMILES: CCN(C)C(=O)c1ccn(Cc2ccc(-c3noc(C(F)(F)F)n3)s2)n1] | 1.53 | 386.00 | B | |
| 1.144 | N-sec-butyl-1-[[5-[5-(trifluoromethyl)-1,2,4-oxadiazol-3-yl]-2-thienyl]methyl]-1,2,4-triazole-3-carboxamide | 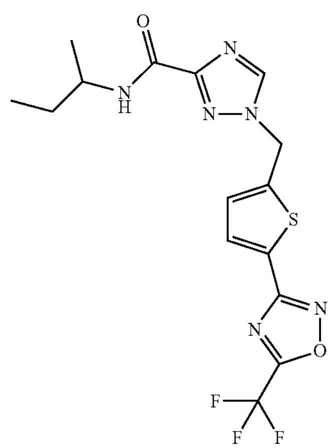 [SMILES: CCC(C)NC(=O)c1ncn(Cc2ccc(-c3noc(C(F)(F)F)n3)s2)n1] | 1.51 | 401.01 | B | |
| 1.145 | N-(2,2-dimethylpropyl)-1-[[5-[5-(trifluoromethyl)-1,2,4-oxadiazol-3-yl]-2-thienyl]methyl]-1,2,4-triazole-3-carboxamide | 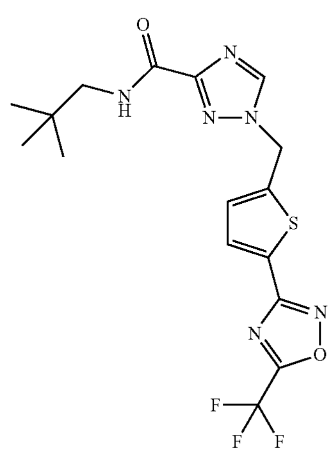 [SMILES: CC(C)(C)CNC(=O)c1ncn(Cc2ccc(-c3noc(C(F)(F)F)n3)s2)n1] | 1.62 | 415.03 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.146 | N-isopropyl-1-[[5-[5-(trifluoromethyl)-1,2,4-oxadiazol-3-yl]-2-thienyl]methyl]-1,2,4-triazole-3-carboxamide | 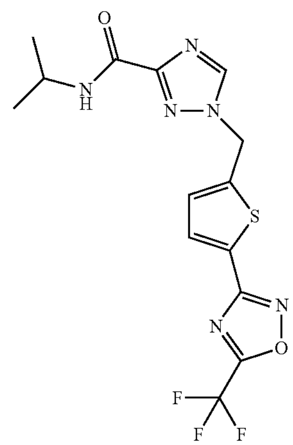 [SMILES: CC(C)NC(=O)c1ncn(Cc2ccc(-c3noc(C(F)(F)F)n3)s2)n1] | 1.41 | 386.99 | B | |
| 1.147 | N-methoxy-N-methyl-1-[[5-[5-(trifluoromethyl)-1,2,4-oxadiazol-3-yl]-2-thienyl]methyl]-1,2,4-triazole-3-carboxamide | 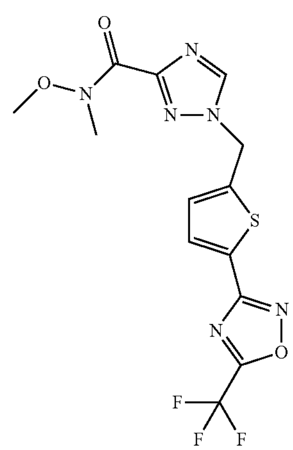 [SMILES: CON(C)C(=O)c1ncn(Cc2ccc(-c3noc(C(F)(F)F)n3)s2)n1] | 1.32 | 388.97 | B | |
| 1.148 | N,N-dimethyl-1-[[5-[5-(trifluoromethyl)-1,2,4-oxadiazol-3-yl]-2-thienyl]methyl]-1,2,4-triazole-3-carboxamide | 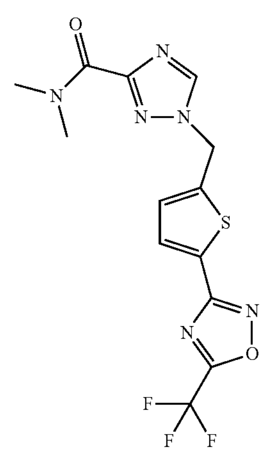 [SMILES: CN(C)C(=O)c1ncn(Cc2ccc(-c3noc(C(F)(F)F)n3)s2)n1] | 1.28 | 372.97 | B | |

TABLE T1-continued

Melting point (mp) data and/or retention times (R_t) for compounds according to Formula (I):

| Entry | Name | Structure | Rt (min) | Mass charge | Method | mp (° C.) |
|---|---|---|---|---|---|---|
| 1.149 | N-cyclohexyl-1-[[5-[5-(trifluoromethyl)-1,2,4-oxadiazol-3-yl]-2-thienyl]methyl]-1,2,4-triazole-3-carboxamide | 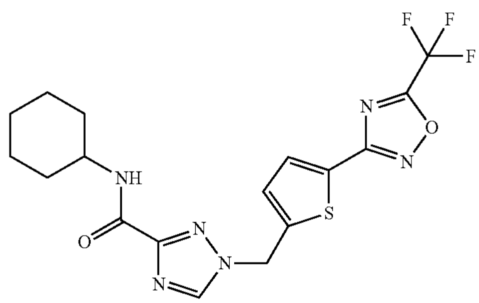 [SMILES: O=C(NC1CCCCC1)c1ncn(Cc2ccc(-c3noc(C(F)(F)F)n3)s2)n1] | 1.64 | 427.04 | B | |
| 1.150 | N-ethyl-1-[[5-[5-(trifluoromethyl)-1,2,4-oxadiazol-3-yl]-2-thienyl]methyl]-1,2,4-triazole-3-carboxamide | 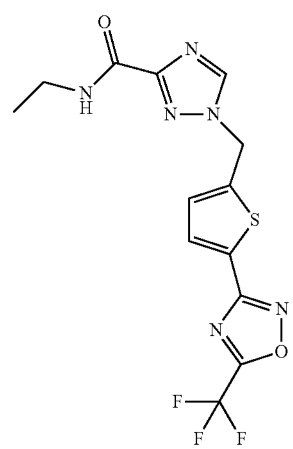 [SMILES: CCNC(=O)c1ncn(Cc2ccc(-c3noc(C(F)(F)F)n3)s2)n1] | 1.30 | 372.97 | B | |
| 1.151 | N-allyl-1-[[5-[5-(trifluoromethyl)-1,2,4-oxadiazol-3-yl]-2-thienyl]methyl]-1,2,4-triazole-3-carboxamide | 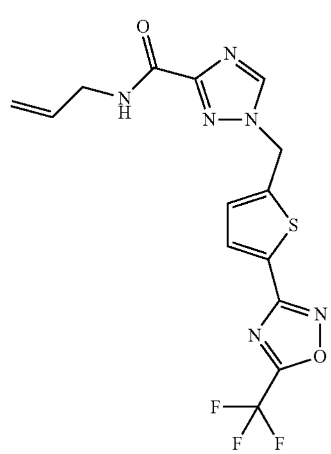 [SMILES: C=CCNC(=O)c1ncn(Cc2ccc(-c3noc(C(F)(F)F)n3)s2)n1] | 1.36 | 384.97 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.152 | N-isobutyl-1-[[5-[5-(trifluoromethyl)-1,2,4-oxadiazol-3-yl]-2-thienyl]methyl]-1,2,4-triazole-3-carboxamide | 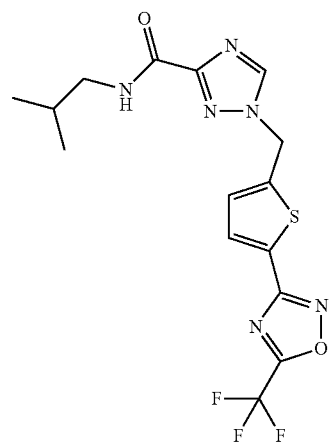 [SMILES: CC(C)CNC(=O)c1ncn(Cc2ccc(-c3noc(C(F)(F)F)n3)s2)n1] | 1.50 | 401.01 | B | |
| 1.153 | N-cyclooropyl-1-[[5-[5-(trifluoromethyl)-1,2,4-oxadiazol-3-yl]-2-thienyl]methyl]-1,2,4-triazole-3-carboxamide | 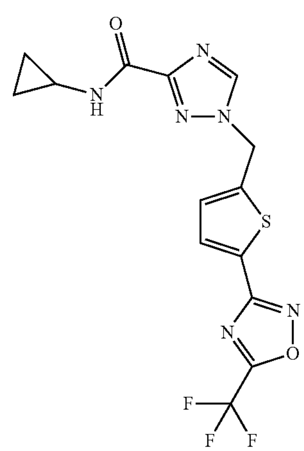 [SMILES: O=C(NC1CC1)c1ncn(Cc2ccc(-c3noc(C(F)(F)F)n3)s2)n1] | 1.32 | 384.97 | B | |
| 1.154 | N,N-diethyl-1-[[5-[5-(trifluoromethyl)-1,2,4-oxadiazol-3-yl]-2-thienyl]methyl]-1,2,4-triazole-3-carboxamide | 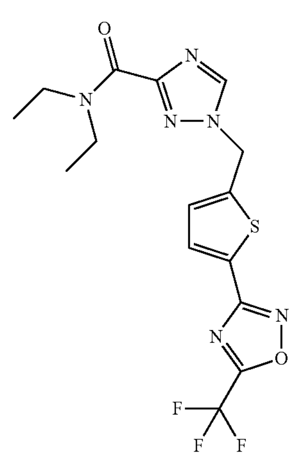 [SMILES: CCN(CC)C(=O)c1ncn(Cc2ccc(-c3noc(C(F)(F)F)n3)s2)n1] | 1.49 | 401.01 | B | |

TABLE T1-continued

Melting point (mp) data and/or retention times (R,) for compounds according to Formula (I):

| Entry | Name | Structure | Rt (min) | Mass charge | Method | mp (° C.) |
|---|---|---|---|---|---|---|
| 1.155 | N-sec-butyl-2-[[5-[5-(trifluoromethyl)-1,2,4-oxadiazol-3-yl]-2-thienyl]methyl]pyrazole-3-carboxamide | 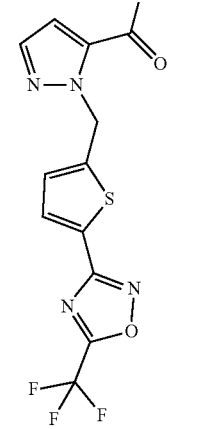 | 1.72 | 400.07 | B | |
| 1.156 | N-(2,2-dimethylpropyl)-2-[[5-[5-(trifluoromethyl)-1,2,4-oxadiazol-3-yl]-2-thienyl]methyl]pyrazole-3-carboxamide | 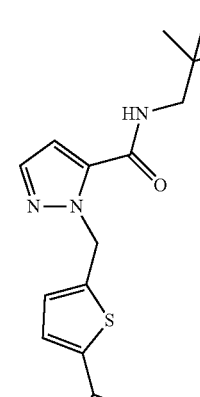 | 1.83 | 414.09 | B | |
| 1.157 | N-isopropyl-2-[[5-[5-(trifluoromethyl)-1,2,4-oxadiazol-3-yl]-2-thienyl]methyl]pyrazole-3-carboxamide | 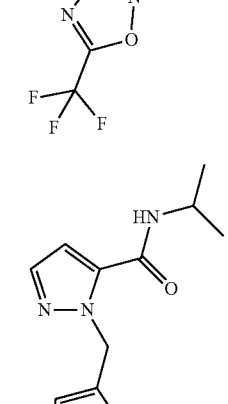 | 1.62 | 386.04 | B | |

TABLE T1-continued

Melting point (mp) data and/or retention times (R,) for compounds according to Formula (I):

| Entry | Name | Structure | Rt (min) | Mass charge | Method | mp (° C.) |
|---|---|---|---|---|---|---|
| 1.158 | N-methoxy-N-methyl-2-[[5-[5-(trifluoromethyl)-1,2,4-oxadiazol-3-yl]-2-thienyl]methyl]pyrazole-3-carboxamide | 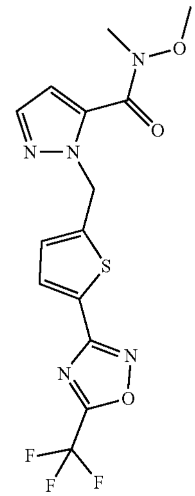 [SMILES: CON(C)C(=O)c1ccnn1Cc1ccc(-c2noc(C(F)(F)F)n2)s1] | 1.58 | 388.02 | B | |
| 1.159 | N-cyclohexyl-2-[[5-[5-(trifluoromethyl)-1,2,4-oxadiazol-3-yl]-2-thienyl]methyl]pyrazole-3-carboxamide | 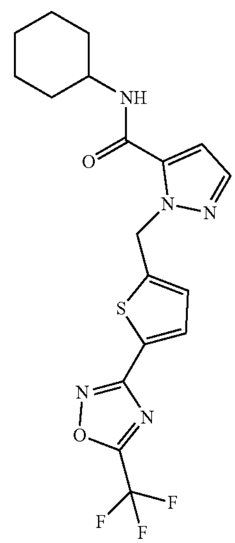 [SMILES: O=C(NC1CCCCC1)c1ccnn1Cc1ccc(-c2noc(C(F)(F)F)n2)s1] | 1.86 | 426.09 | B | |
| 1.160 | N-isobutyl-2-[[5-[5-(trifluoromethyl)-1,2,4-oxadiazol-3-yl]-2-thienyl]methyl]pyrazole-3-carboxamide | 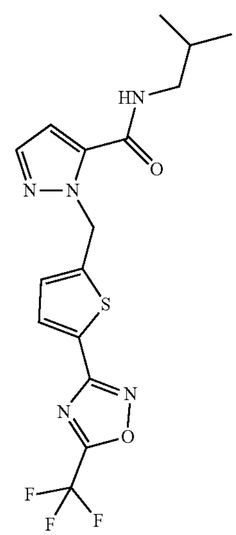 [SMILES: CC(C)CNC(=O)c1ccnn1Cc1ccc(-c2noc(C(F)(F)F)n2)s1] | 1.73 | 400.07 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.161 | N,N-diethyl-2-[[5-[5-(trifluoromethyl)-1,2,4-oxadiazol-3-yl]-2-thienyl]methyl]pyrazole-3-carboxamide | 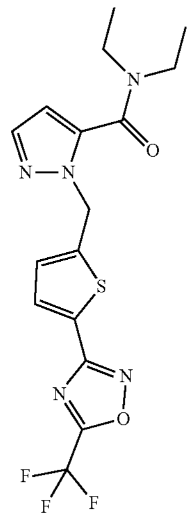 [SMILES: CCN(CC)C(=O)c1ccnn1Cc1ccc(-c2noc(C(F)(F)F)n2)s1] | 1.65 | 400.07 | B | |
| 1.162 | N-phenyl-2-[[5-[5-(trifluoromethyl)-1,2,4-oxadiazol-3-yl]-2-thienyl]methyl]pyrazole-3-carboxamide | 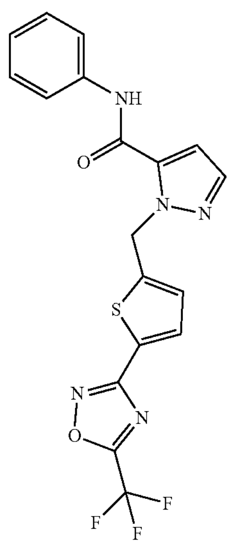 [SMILES: O=C(Nc1ccccc1)c1ccnn1Cc1ccc(-c2noc(C(F)(F)F)n2)s1] | 1.79 | 420.03 | B | |
| 1.163 | N-benzyl-2-[[5-[5-(trifluoromethyl)-1,2,4-oxadiazol-3-yl]-2-thienyl]methyl]pyrazole-3-carboxamide | 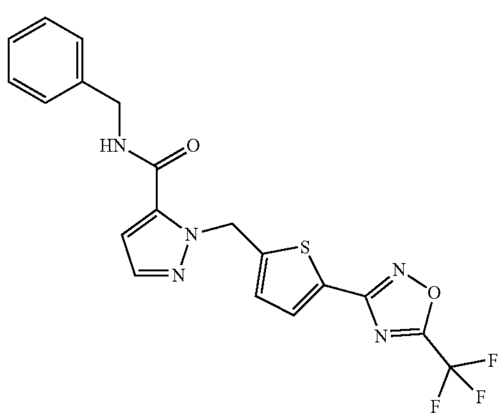 [SMILES: O=C(NCc1ccccc1)c1ccnn1Cc1ccc(-c2noc(C(F)(F)F)n2)s1] | 1.75 | 434.05 | B | |

TABLE T1-continued

Melting point (mp) data and/or retention times ($R_t$) for compounds according to Formula (I):

| Entry | Name | Structure | Rt (min) | Mass charge | Method | mp (° C.) |
|---|---|---|---|---|---|---|
| 1.164 | N-ethoxy-2-[[5-[5-(trifluoromethyl)-1,2,4-oxadiazol-3-yl]-2-thienyl]methyl]pyrazde-3-carboxamide | 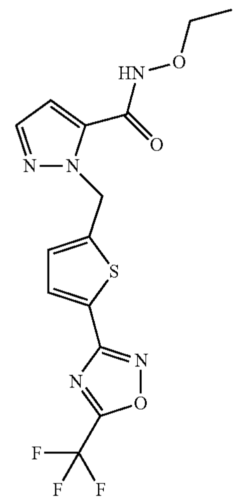 [SMILES: CCONC(=O)c1ccnn1Cc1ccc(-c2noc(C(F)(F)F)n2)s1] | 1.46 | 388.02 | B | |
| 1.165 | N-cyclopentyl-2-[[5-[5-(trifluoromethyl)-1,2,4-oxadiazol-3-yl]-2-thienyl]methyl]pyrazole-3-carboxamide | 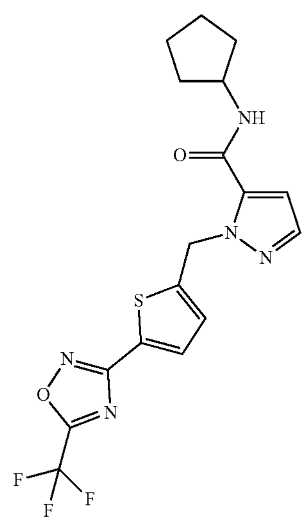 [SMILES: O=C(NC1CCCC1)c1ccnn1Cc1ccc(-c2noc(C(F)(F)F)n2)s1] | 1.76 | 412.08 | B | |
| 1.166 | morpholino-[2-[[5-[5-(trifluoromethyl)-1,2,4-oxadiazol-3-yl]-2-thienyl]methyl]pyrazol-3-yl]methanone | 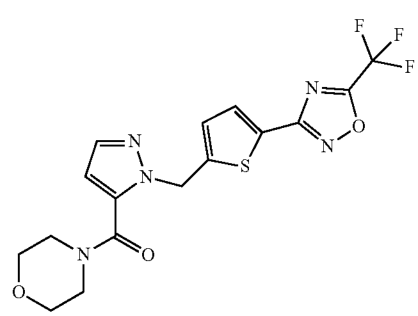 [SMILES: O=C(c1ccnn1Cc1ccc(-c2noc(C(F)(F)F)n2)s1)N1CCOCC1] | 1.43 | 414.05 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.167 | N-tert-butyl-2-[[5-[5-(trifluoromethyl)-1,2,4-oxadiazol-3-yl]-2-thienyl]methyl]pyrazole-3-carboxamide | 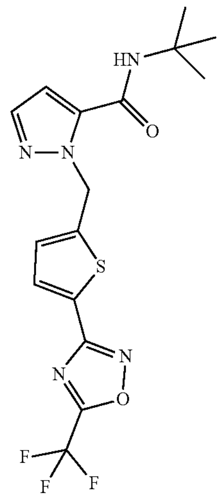 [SMILES: CC(C)(C)NC(=O)c1ccnn1Cc1ccc(-c2noc(C(F)(F)F)n2)s1] | 1.79 | 400.07 | B | |
| 1.168 | N-prop-2-ynyl-2-[[5-[5-(trifluoromethyl)-1,2,4-oxadiazol-3-yl]-2-thienyl]methyl]pyrazole-3-carboxamide | 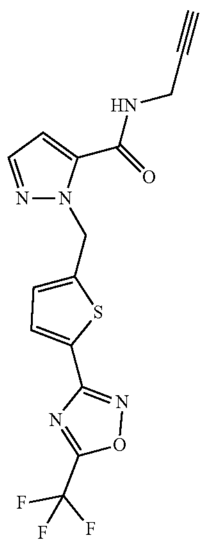 [SMILES: C#CCNC(=O)c1ccnn1Cc1ccc(-c2noc(C(F)(F)F)n2)s1] | 1.50 | 382.02 | B | |
| 1.169 | N-ethyl-N-methyl-2-[[5-[5-(trifluoromethyl)-1,2,4-oxadiazol-3-yl]-2-thienyl]methyl]pyrazole-3-carboxamide | 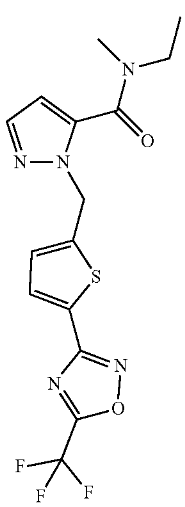 [SMILES: CCN(C)C(=O)c1ccnn1Cc1ccc(-c2noc(C(F)(F)F)n2)s1] | 1.54 | 386.08 | B | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.170 | N-methyl-1-[[5-[5-(trifluoromethyl)-1,2,4-oxadiazoi-3-yl]-2-thienyl]methyl]imidazole-4-carboxamide | 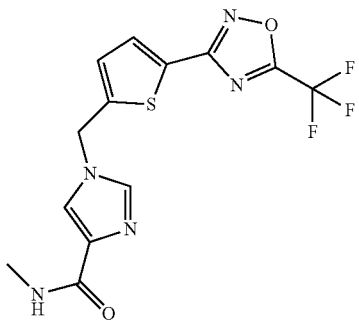 [SMILES: CNC(=O)c1cn(Cc2ccc(-c3noc(C(F)(F)F)n3)s2)cn1] | 1.20 | 358 | C | |
| 1.171 | N-cyclopropyl-1-[[5-[5-(trifluoromethyl)-1,2,4-oxadiazol-3-yl]-2-thienyl]methyl]imidazole-4-carboxamide | 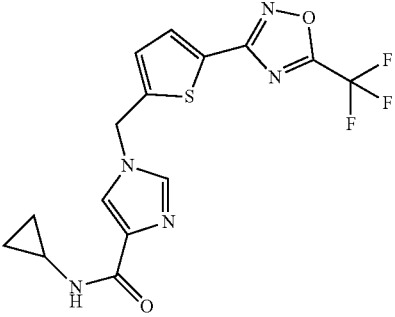 [SMILES: O=C(NC1CC1)c1cn(Cc2ccc(-c3noc(C(F)(F)F)n3)s2)cn1] | | | | |
| 1.172 | N,N-dimethyl-1-[[5-[5-(trifluoromethyl)-1,2,4-oxadiazol-3-yl)-2-thienyl]methyl]imidazole-4-carboxamide | 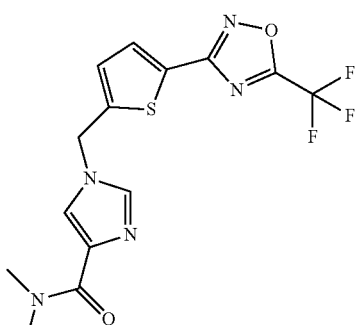 | | | | |
| 1.173 | N-prop-2-ynyl-1-[[5-[5-(trifluoromethyl)-1,2,4-oxadiazol-3-yl]-2-thienyl]methyl]imidazole-4-carboxamide | 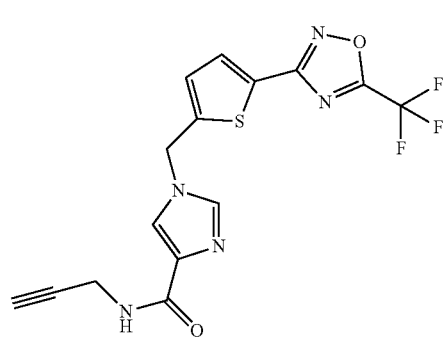 [SMILES: C#CCNC(=O)c1cn(Cc2ccc(-c3noc(C(F)(F)F)n3)s2)cn1] | | | | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.174 | N-methoxy-1-[[5-[5-(trifluoromethyl)-1,2,4-oxadiazol-3-yl]-2-thienyl]methyl]imidazole-4-carboxamide | 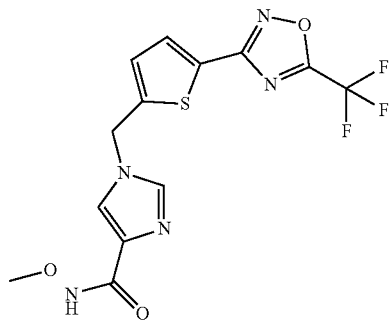 | 1.37 | 374 | C | |
| 1.175 | N-isopropyl-1-[[5-[5-(trifluoromethyl)-1,2,4-oxadiazol-3-yl]-2-thienyl]methyl]imidazole-4-carboxamide | 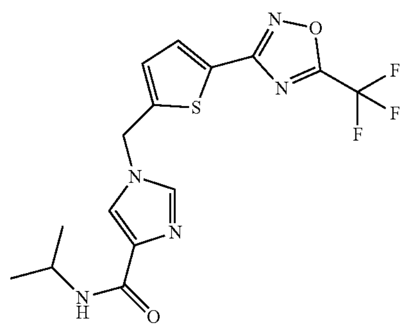 [SMILES: CC(C)NC(=O)c1cn(Cc2ccc(-c3noc(C(F)(F)F)n3)s2)cn1] | | | | |
| 1.176 | N-methyl-1-[[5-[5-(trifluoromethyl)-1,2,4-oxadiazol-3-yl]-2-thienyl]methyl]imidazole-2-carboxamide | 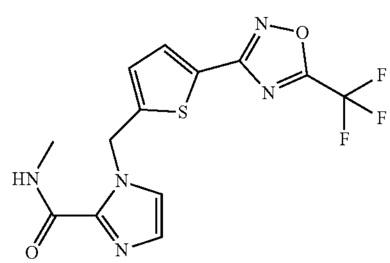 [SMILES: CNC(=O)c1nccn1Cc1ccc(-c2noc(C(F)(F)F)n2)s1] | 1.39 | 358 | C | |
| 1.177 | N-cyclopropyl-1-[[5-[5-(trifluoromethyl)-1,2,4-oxadiazol-3-yl]-2-thienyl]methyl]imidazole-2-carboxamide | 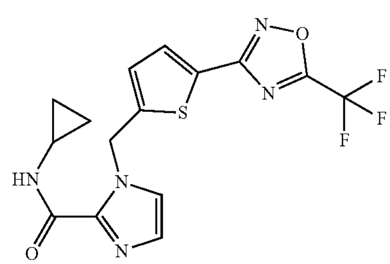 [SMILES: O=C(NC1CC1)c1nccn1Cc1ccc(-c2noc(C(F)(F)F)n2)s1] | 1.46 | 384 | C | |
| 1.178 | N,N-dimethyl-1-[[5-[5-(trifluoromethyl)-1,2,4-oxadiazol-3-yl]-2-thienyl]methyl]imidazole-2-carboxamide | 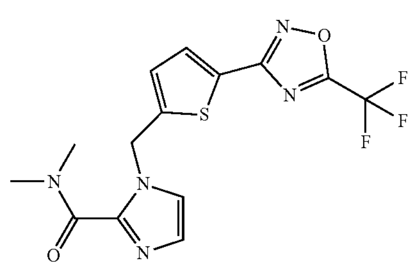 [SMILES: CN(C)C(=O)c1nccn1Cc1ccc(-c2noc(C(F)(F)F)n2)s1] | 1.31 | 372 | C | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.179 | N-prop-2-ynyl-1-[[5-[5-(trifluoromethyl)-1,2,4-oxadiazol-3-yl]-2-thienyl]methyl]imidazole-2-carboxamide | 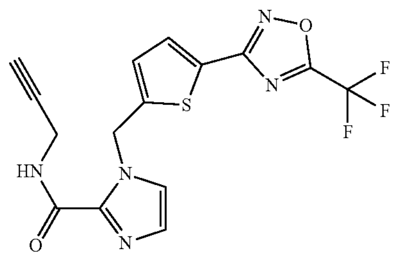 [SMILES: C#CCNC(=O)c1nccn1Cc1ccc(-c2noc(C(F)(F)F)n2)s1] | 1.45 | Not detected | C | |
| 1.180 | N-methoxy-1-[[5-[5-(trifluoromethyl)-1,2,4-oxadiazol-3-yl]-2-thienyl]methyl]imidazole-2-carboxamide | 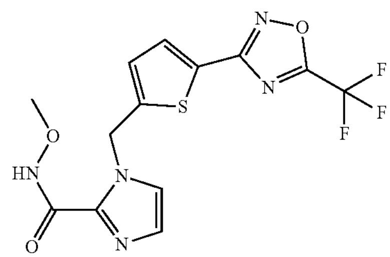 [SMILES: CONC(=O)c1nccn1Cc1ccc(-c2noc(C(F)(F)F)n2)s1] | 1.37 | 374 | C | |
| 1.181 | N-isopropyl-1-[[5-[5-(trifluoromethyl)-1,2,4-oxadiazol-3-yl]-2-thienyl]methyl]imidazole-2-carboxamide | 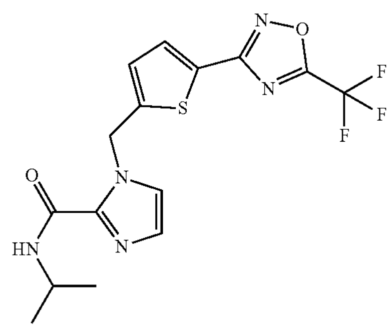 [SMILES: CC(C)NC(=O)c1nccn1Cc1ccc(-c2noc(C(F)(F)F)n2)s1] | | | | |
| 1.182 | N-methyl-3-[[5-[5-(trifluoromethyl)-1,2,4-oxadiazol-3-yl]-2-thienyl]methyl]imidazole-4-carboxamide | 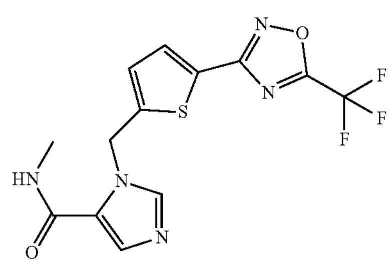 [SMILES: CNC(=O)c1cncn1Cc1ccc(-c2noc(C(F)(F)F)n2)s1] | 0.90 | 358 | C | |
| 1.183 | N-cyclopropyl-3-[[5-[5-(trifluoromethyl)-1,2,4-oxadiazol-3-yl]-2-thienyl]methyl]imidazole-4-carboxamide | 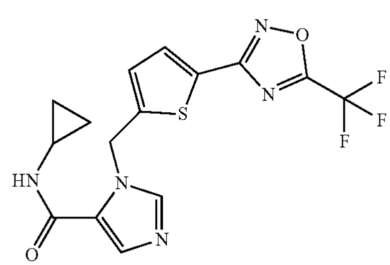 [SMILES: O=C(NC1CC1)c1cncn1Cc1ccc(-c2noc(C(F)(F)F)n2)s1] | | | | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.184 | N,N-dimethyl-3-[[5-[5-(trifluoromethyl)-1,2,4-oxadiazol-3-yl]-2-thienyl]methyl]imidazole-4-carboxamide | 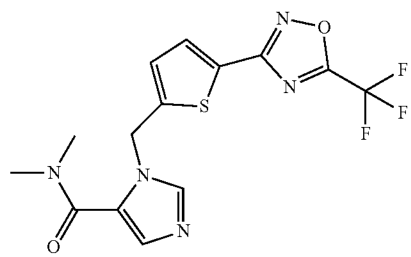 [SMILES: CN(C)C(=O)c1cncn1Cc1ccc(-c2noc(C(F)(F)F)n2)s1] | | | | |
| 1.185 | N-prop-2-ynyl-3-[[5-[5-(trifluoromethyl)-1,2,4-oxadiazol-3-yl]-2-thienyl]methyl]imidazole-4-carboxamide | 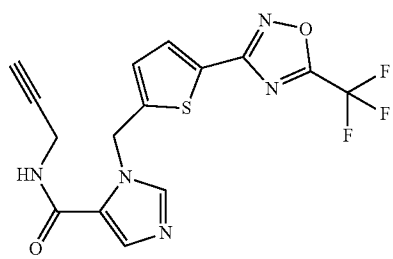 [SMILES: C#CCNC(=O)c1cncn1Cc1ccc(-c2noc(C(F)(F)F)n2)s1] | | | | |
| 1.186 | N-methoxy-3-[[5-[5-(trifluoromethyl)-1,2,4-oxadiazol-3-yl]-2-thienyl]methyl]imidazole-4-carboxamide | 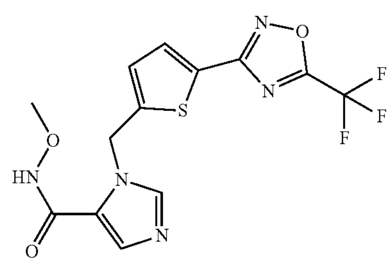 [SMILES: CONC(=O)c1cncn1Cc1ccc(-c2noc(C(F)(F)F)n2)s1] | | | | |
| 1.187 | N-isopropyl-3-[[5-[5-(trifluoromethyl)-1,2,4-oxadiazol-3-yl]-2-thienyl]methyl]imidazole-4-carboxamide | 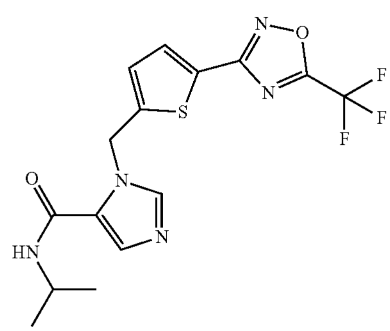 [SMILES: CC(C)NC(=O)c1cncn1Cc1ccc(-c2noc(C(F)(F)F)n2)s1] | | | | |
| 1.188 | methyl 1-[[5-[5-(trifluoromethyl)-1,2,4-oxadiazol-3-yl]-2-thienyl]methyl]imidazole-2-carboxylate | 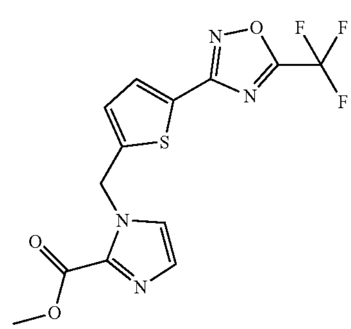 [SMILES: COC(=O)c1nccn1Cc1ccc(-c2noc(C(F)(F)F)n2)s1] | 1.39 | 359 | C | |

TABLE T1-continued

Melting point (mp) data and/or retention times (R$_t$) for compounds according to Formula (I):

| Entry | Name | Structure | Rt (min) | Mass charge | Method | mp (° C.) |
|---|---|---|---|---|---|---|
| 1.189 | methyl 3-[[5-[5-(trifluoromethyl)-1,2,4-oxadiazol-3-yl]-2-thienyl]methyl]imidazole-4-carboxylate | 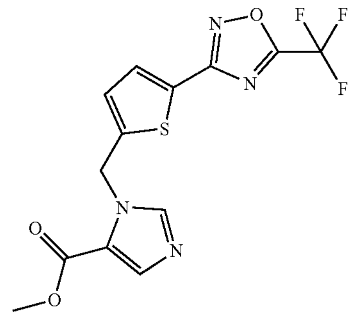 [SMILES: COC(=O)c1cncn1Cc1ccc(-c2noc(C(F)(F)F)n2)s1] | 1.39 | 359 | C | |
| 1.190 | methyl 1-[[5-[5-(trifluoromethyl)-1,2,4-oxadiazol-3-yl]-2-thienyl]methyl]imidazole-4-carboxylate | 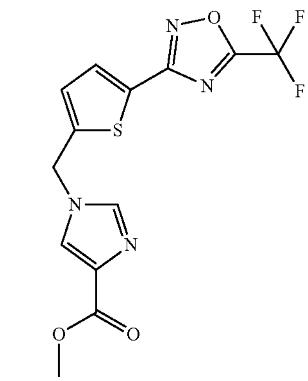 [SMILES: COC(=O)c1cn(Cc2ccc(-c3noc(C(F)(F)F)n3)s2)cn1] | 1.33 | 359 | C | |

BIOLOGICAL EXAMPLES

Leaf disks or leaf segments of various plant species are cut from plants grown in a greenhouse. The cut leaf disks or segments are placed in multiwell plates (24-well format) onto water agar. The leaf disks are sprayed with a test solution before (preventative) or after (curative) inoculation. Compounds to be tested are prepared as DMSO solutions (max. 10 mg/mL) which are diluted to the appropriate concentration with 0.025% Tween20 just before spraying. The inoculated leaf disks or segments are incubated under defined conditions (temperature, relative humidity, light, etc.) according to the respective test system. A single evaluation of disease level is carried out 3 to 14 days after inoculation, depending on the pathosystem. Percent disease control relative to the untreated check leaf disks or segments is then calculated.

General Examples of Liquid Culture Tests in Well Plates:

Mycelia fragments or conidia suspensions of a fungus prepared either freshly from liquid cultures of the fungus or from cryogenic storage, are directly mixed into nutrient broth. DMSO solutions of the test compound (max. 10 mg/mL) are diluted with 0.025% Tween20 by a factor of 50 and 10 µL of this solution is pipetted into a microtiter plate (96-well format). The nutrient broth containing the fungal spores/mycelia fragments is then added to give an end concentration of the tested compound. The test plates are incubated in the dark at 24° C. and 96% relative humidity. The inhibition of fungal growth is determined photometrically after 2 to 7 days, depending on the pathosystem, and percent antifungal activity relative to the untreated check is calculated.

Example 1: Fungicidal Activity Against *Puccinia recondita* f. Sp. *Tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% relative humidity (rh) under a light regime of 12 hours light/12 hours darkness in a climate cabinet and the activity of a compound was assessed as percent disease control compared to untreated when an appropriate level of disease damage appears in untreated check leaf segments (7 to 9 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.3, 1.4, 1.5, 1.6, 1.7, 1.8, 1.9, 1.10, 1.11, 1.12, 1.13, 1.14, 1.16, 1.17, 1.18, 1.19, 1.21, 1.22, 1.23, 1.24, 1.25, 1.26, 1.30, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.66, 1.68, 1.70, 1.71, 1.73, 1.79, 1.82, 1.83, 1.84, 1.85, 1.88, 1.91, 1.94, 1.95, 1.96, 1.98, 1.100, 1.101, 1.102, 1.103, 1.105, 1.106, 1.109, 1.113, 1.115, 1.120, 1.122, 1.126, 1.128, 1.129, 1.130, 1.137, 1.140, 1.144, 1.145, 1.149, 1.151, 1.153, 1.155, 1.156, 1.157, 1.158, 1.159, 1.160, 1.161, 1.162, 1.163, 1.164, 1.165, 1.166, 1.167, 1.168, 1.169, 1.176 and 1.177.

Example 2: Fungicidal Activity Against *Puccinia recondita* f. sp. *Tritici*/Wheat/Leaf Disc Curative (Brown Rust)

Wheat leaf segments cv. Kanzler are placed on agar in multiwell plates (24-well format). The leaf segments are then inoculated with a spore suspension of the fungus. Plates were stored in darkness at 19C and 75% relative humidity. The formulated test compound diluted in water was applied 1 day after inoculation. The leaf segments were incubated at 19° C. and 75% relative humidity under a light regime of 12 hours light/12 hours darkness in a climate cabinet and the activity of a compound was assessed as percent disease control compared to untreated when an appropriate level of disease damage appears in untreated check leaf segments (6 to 8 days after application).

The following compounds at 200 ppm in the applied formulation give at least 80% disease control in this test when compared to untreated control leaf disks under the same conditions, which show extensive disease development.

Compounds (from Table T1) 1.1, 1.2, 1.4, 1.6, 1.8, 1.9, 1.11, 1.13, 1.14, 1.16, 1.17, 1.19, 1.21, 1.22, 1.23, 1.24, 1.25, 1.30, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.63, 1.64, 1.66, 1.68, 1.70, 1.73, 1.79, 1.82, 1.83, 1.84, 1.85, 1.88, 1.91, 1.94, 1.95, 1.96, 1.98, 1.100, 1.101, 1.102, 1.103, 1.105, 1.106, 1.109, 1.113, 1.120, 1.122, 1.126, 1.128, 1.129, 1.130, 1.137, 1.140, 1.144, 1.145, 1.151, 1.153, 1.158, 1.160, 1.161, 1.164, 1.166, 1.168, 1.169, 1.176 and 1.177.

Example 3: Fungicidal Activity Against *Phakopsora pachyrhizi*/Soybean/Leaf Disc Preventative (Asian Soybean Rust)

Soybean leaf disks are placed on water agar in multiwell plates (24-well format) and sprayed with the formulated test compound diluted in water. One day after application leaf discs are inoculated by spraying a spore suspension on the lower leaf surface. After an incubation period in a climate cabinet of 24-36 hours in darkness at 20° C. and 75% rh leaf disc are kept at 20° C. with 12 h light/day and 75% rh. The activity of a compound is assessed as percent disease control compared to untreated when an appropriate level of disease damage appears in untreated check leaf disks (12 to 14 days after application).

The following compounds at 200 ppm in the applied formulation give at least 80% disease control in this test when compared to untreated control leaf disks under the same conditions, which show extensive disease development.

Compounds (from Table T1) 1.1, 1.4, 1.6, 1.13, 1.14, 1.17, 1.19, 121, 1.23, 1.24, 1.25, 1.30, 1.32, 1.33, 1.34, 1.35, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60 and 1.61.

Example 4: Fungicidal Activity Against *Glomerella lagenarium* (*Colletotrichum lagenarium*) Liquid Culture/Cucumber/Preventative (Anthracnose)

Conidia of the fungus from cryogenic storage are directly mixed into nutrient broth (PDB—potato dextrose broth). After placing a (DMSO) solution of test compound into a microtiter plate (96-well format), the nutrient broth containing the fungal spores is added. The test plates are incubated at 24° C. and the inhibition of growth is measured photometrically 3 to 4 days after application.

The following compounds at 20 ppm in the applied formulation give at least 80% disease control in this test when compared to untreated control under the same conditions, which show extensive disease development.

Compounds (from Table T1) 1.1, 1.2, 1.3, 1.4, 1.5, 1.6, 1.7, 1.8, 1.9, 1.10, 1.11, 1.12, 1.13, 1.14, 1.15, 1.16, 1.17, 1.18, 1.19, 1.20, 1.21, 1.22, 1.23, 1.24, 1.25, 126, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.59, 1.60, 1.61, 1.62, 1.64, 1.66, 1.68, 1.70, 1.71, 1.73, 1.79, 1.82, 1.84, 1.85, 1.88, 1.91, 1.94, 1.95, 1.96, 1.98, 1.100, 1.101, 1.102, 1.103, 1.105, 1.106, 1.109, 1.115, 1.120, 1.122, 1.126, 1.128, 1.129, 1.130, 1.137, 1.140, 1.144, 1.145, 1.149, 1.151, 1.153, 1.155, 1.156, 1.157, 1.158, 1.159, 1.160, 1.161, 1.162, 1.163, 1.164, 1.165, 1.166, 1.167, 1.168 and 1.169.

What is claimed is:
1. A compound of Formula (I):

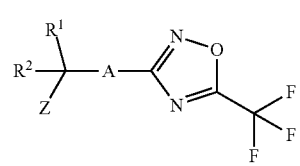

(I)

wherein
A is selected from A-1, A-2 or A-3;

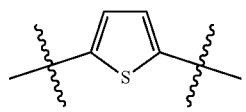

(A-1)

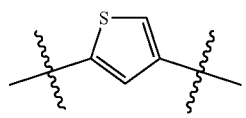

(A-2)

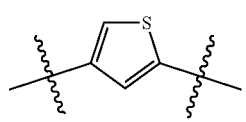

(A-3)

$R^1$ and $R^2$ independently represent hydrogen, methyl, ethyl, fluoro, cyano, difluoromethyl or trifluoromethyl; and Z is selected from $Z^1$, $Z^2$ or $Z^3$; wherein
$Z^1$ represents a 5- or 6-membered non-aromatic heterocyclyl ring selected from

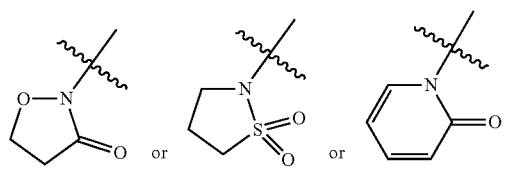 [SMILES: *N1OCCC1=O ; *N1CCCS1(=O)=O ; *n1ccccc1=O]

wherein the heterocyclyl is optionally substituted by 1 or 2 substituents, which may be the same or different, selected from $R^4$;

$R^4$ represents cyano, halogen, hydroxy, amino, methyl, ethyl, difluoromethyl, trifluoromethyl, methoxy, N-methylamino or N,N-dimethylamino;

$Z^2$ represents a 5- or 6-membered heteroaryl ring containing 1 ring nitrogen, wherein the heteroaryl optionally comprises 1, 2 or 3 additional ring members independently selected from O, S, or N, and wherein the heteroaryl is optionally substituted by: 1 or 2 substituents selected from $R^5$, 1 substituent selected from $R^6$, or 1 substituent selected from $R^5$ and 1 substituent selected from $R^6$, and wherein further the heteroaryl is bound to the rest of the molecule through a ring nitrogen;

$R^5$ represents hydroxyl, amino, cyano, halogen, formyl, nitro, $C_{1-4}$alkyl, $C_{1-4}$alkoxy, $C_{3-4}$alkenyl, $C_{3-4}$alkynyl, $C_{3-4}$alkenyloxy, $C_{3-4}$alkynyloxy, cyano$C_{1-2}$alkyl, $C_{1-2}$haloalkyl, hydroxy$C_{1-2}$alkyl, $C_{1-2}$alkoxy$C_{1-2}$alkyl, $C_{1-2}$alkoxy$C_{1-2}$alkoxy$C_{1-2}$alkyl, N,N-dimethylamino, $C_{1-3}$alkoxycarbonyl$C_{1-2}$alkyl, $C_{1-3}$alkylcarbonyloxy$C_{1-2}$alkyl, N—$C_{1-3}$alkylaminocarbonyl$C_{1-2}$alkyl, N,N-di$C_{1-3}$alkylaminocarbonyl$C_{1-2}$alkyl, $C_{1-2}$alkylsulfonyl, $C_{1-3}$alkylcarbonyl, $C_{1-3}$alkyldicarbonyl, $C_{1-3}$alkoxydicarbonyl, N—$C_{1-3}$alkylaminodicarbonyl, or N,N-di$C_{1-3}$alkylaminodicarbonyl; or $R^5$ represents —C(O)N($R^a$)($R^b$), wherein:

$R^a$ represents hydrogen, $C_{1-6}$alkyl, $C_{3-4}$alkenyl, $C_{3-4}$alkynyl, $C_{1-3}$haloalkyl, $C_{3-4}$haloalkenyl, $C_{1-4}$alkoxy, $C_{1-2}$alkoxy$C_{1-3}$alkyl, $C_{2-3}$haloalkoxy, $C_{3-4}$alkenyloxy, $C_{3-4}$alkynyloxy, N—$C_{1-3}$alkylamino, or N,N-di$C_{1-2}$alkylamino; or $R^a$ represents $C_{3-5}$cycloalkyl, $C_{3-5}$cycloalkyl$C_{1-2}$alkyl, phenyl, phenyl$C_{1-2}$alkyl, heterocyclyl, wherein the heterocyclyl moiety is a 4- to 6-membered non-aromatic ring which comprises 1 or 2 heteroatoms independently selected from N, O or S, with the proviso that the heterocyclyl cannot contain 2 contiguous atoms selected from O and S, heteroaryl or heteroaryl$C_{1-2}$alkyl, wherein the heteroaryl moiety is a 5- or 6-membered aromatic ring which comprises 1, 2, 3, or 4 heteroatoms individually selected from N, O and S; wherein the cycloalkyl, phenyl, heterocyclyl or heteroaryl is optionally substituted by 1 or 2 substituents, which may be the same or different, selected from hydroxyl, amino, formyl, acyl, cyano, halogen, methyl, trifluoromethyl, methoxy, or N,N-dimethylamino, and wherein when $R^a$ represents cycloalkyl or heterocyclyl, these cycles optionally contain 1 group selected from C(O) or S(O)$_2$; and $R^b$ represents hydrogen, methyl, ethyl, propyl, prop-2-enyl, prop-2-ynyl, cyclopropyl, or cyclopropylmethyl; or $R^a$ and $R^b$, together with the nitrogen atom they share, form an azetidinyl, pyrrolidinyl, isooxazolidinyl, morpholino, piperazin-4-yl, or piperidinyl ring optionally substituted by 1 or 2 groups selected from halogen, methyl, ethyl or methoxy; or $R^5$ represents —C(O)O—$R^c$, wherein:

$R^c$ represents hydrogen, $C_{1-6}$alkyl, $C_{3-5}$alkenyl, $C_{3-5}$alkynyl, $C_{1-3}$haloalkyl, $C_{3-4}$haloalkenyl, N,N-di$C_{1-3}$alkylamino$C_{1-3}$alkyl, $C_{3-6}$cycloalkyl, $C_{3-4}$cycloalkyl$C_{1-2}$alkyl, phenyl, heterocyclyl, wherein the heterocyclyl moiety is a 4- to 6-membered non-aromatic ring which comprises 1 or 2 heteroatoms independently selected from O, S and N, with the proviso that the heterocyclyl cannot contain 2 contiguous atoms selected from O and S, heteroaryl, wherein the heteroaryl moiety is a 5- or 6-membered aromatic ring which comprises 1, 2 or 3 heteroatoms individually selected from N, O and S; and wherein the cycloalkyl, phenyl, heterocyclyl or heteroaryl is optionally substituted by 1 or 2 substituents, which may be the same or different, selected from hydroxyl, amino, formyl, methylcarbonyl, cyano, halogen, methyl, trifluoromethyl, methoxy, or N,N-dimethylamino, and wherein when $R^c$ represents cycloalkyl or heterocyclyl, these cycles optionally contain 1 group selected from C(O) or S(O)$_2$; or $R^5$ represents —N($R^d$)($R^e$) or —$C_{1-2}$alkyl-N($R^d$)($R^e$), wherein $R^d$ represents $C_{1-3}$alkyl, $C_{3-4}$alkenyl, $C_{3-4}$alkynyl, methylcarbonyl, methoxycarbonyl, N-methylaminocarbonyl, N,N-dimethylaminocarbonyl, N-methoxyaminocarbonyl, N-methyl-N-methoxy-aminocarbonyl, methyl sulfonyl, N-methylaminosulfonyl, N,N-dimethylaminosulfonyl, methyldicarbonyl, N-methylaminodicarbonyl, or N,N-dimethylaminodicarbonyl; and $R^e$ represents hydrogen, methyl, ethyl, or propyl; or $R^d$ and $R^e$, together with the nitrogen atom they share, form an azetidinyl, pyrrolidinyl, isooxazolidinyl, morpholino, piperazin-4-yl, or piperidinyl ring optionally substituted by 1 or 2 groups selected from halogen, methyl, ethyl or methoxy; or $R^5$ represents —CH=N($R^f$), wherein $R^f$ represents $C_{1-4}$alkyl, $C_{1-4}$alkoxy, $C_{2-4}$alkenoxy, or $C_{2-4}$alkynoxy;

$R^6$ represents $C_{3-6}$cycloalkyl, phenyl, heteroaryl, wherein the heteroaryl moiety is a 5- or 6-membered aromatic ring which comprises 1, 2, 3 or 4 heteroatoms individually selected from N, O and S, heterocyclyl, wherein the heterocyclyl moiety is a 4- to 6-membered non-aromatic ring which comprises 1 or 2 heteroatoms individually selected from N, O and S, and wherein the cycloalkyl, phenyl, heteroaryl and heterocyclyl is optionally substituted by 1 or 2 substituents, which may be the same or different, selected from hydroxyl, amino, formyl, acyl, cyano, halogen, methyl, trifluoromethyl, methoxy, N,N-dimethylamino, and wherein when $R^6$ represents cycloalkyl or heterocyclyl, these cycles optionally contain 1 group selected from C(O) or S(O)$_2$;

and $Z^3$ represents a heterobicyclyl which is a 7- to 9-membered saturated, partially saturated, or aromatic fused ring or saturated spirocyclic ring system containing 1 nitrogen, wherein the heterobicyclyl optionally comprises 1 or 2 additional ring members independently selected from N, O, S, C(O) and S(O)$_2$ with the proviso that the heterobicyclyl cannot contain 2 contiguous atoms selected from O and S, wherein the heterobicyclyl is optionally substituted by 1 substituent selected from $R^7$, and wherein further the heterobicyclyl is bound to the rest of the molecule through a ring nitrogen; and $R^7$ is cyano, fluoro, chloro, amino, hydroxy, methyl, difluoromethyl, trifluoromethyl, methoxy, N,N-dimethylamino, formyl, methylcarbonyl, methoxycarbonyl, N-methylaminocarbonyl, or N,N-dimethylaminocarbonyl;

or a salt or N-oxide thereof.

2. A compound according to claim 1, wherein A is A-1.

3. A compound according to claim 1, wherein $R^1$ and $R^2$ are hydrogen.

4. A compound according to claim 1, wherein R⁴ is selected from methyl or ethyl.

5. A compound according to claim 1, wherein Z is Z² selected from:

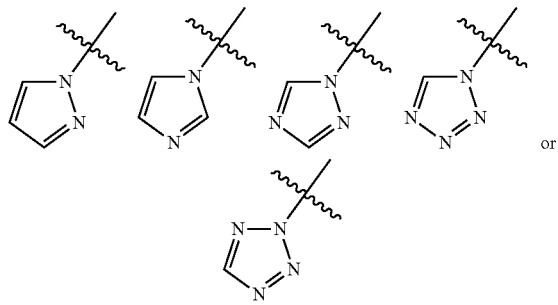

or wherein Z² is optionally substituted by: 1 or 2 substituents selected from R⁵, 1 substituent selected from R⁶, or 1 substituent selected from R⁵ and 1 substituent selected from R⁶.

6. A compound according to claim 5, wherein R⁵ is independently selected from hydroxy, amino, cyano, halogen, formyl, nitro, $C_{1-4}$alkyl, $C_{1-4}$alkoxy, $C_{1-2}$haloalkyl, $C_{1-2}$alkoxy$C_{1-2}$alkyl, N,N-dimethylamino, —C(O)O—R$^c$ wherein R$^c$ is $C_{1-4}$alkyl and —C(O)N(R$^a$)(R$^b$), wherein R$^a$ is selected from hydrogen, $C_{1-4}$alkyl or $C_{1-4}$alkoxy, and R$^b$ is selected from hydrogen or methyl; and R⁶ is phenyl optionally substituted by 1 or 2 substituents, which may be the same or different, selected from hydroxyl, methyl, methoxy, cyano, fluoro, chloro or bromo.

7. A compound according to claim 6, wherein R⁵ is selected from amino, cyano, chloro, fluoro, formyl, nitro, methyl, ethyl, difluoromethyl, methoxymethyl, N,N-dimethylamino, methoxycarbonyl, ethoxycarbonyl or n-propoxycarbonyl; and R⁶ is phenyl optionally substituted by 1 or 2 substituents, which may be the same or different, selected from fluoro, chloro or bromo.

8. A compound according to claim 1, wherein Z² is optionally substituted by 1 or 2 substituents selected from R⁵.

9. A compound according to claim 1, wherein Z is Z³ selected from:

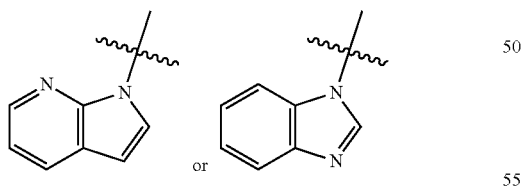

or wherein Z³ is optionally substituted by 1 substituent selected from R⁷.

10. A compound according to claim 9, wherein R⁷ is selected from hydroxyl, methoxy, methyl, cyano, fluoro or chloro.

11. An agrochemical composition comprising a fungicidally effective amount of a compound of Formula (I) according to claim 1.

12. The composition according to claim 11, further comprising at least one additional active ingredient and/or an agrochemically-acceptable diluent or carrier.

13. A method of controlling or preventing infestation of useful plants by phytopathogenic microorganisms, comprising, applying a fungicidally effective amount of a compound of Formula (I) according to claim 1, or a composition comprising compound of Formula (I) according to claim 1 as an active ingredient, to the plants, to parts thereof or the locus thereof.

14. A compound selected from:

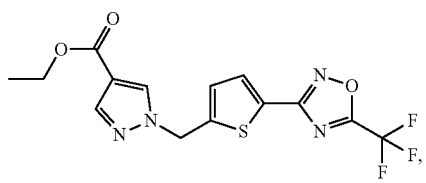

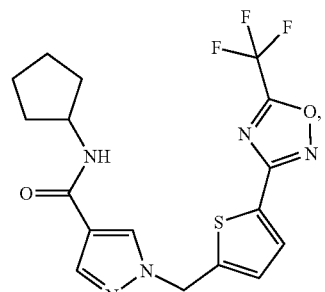

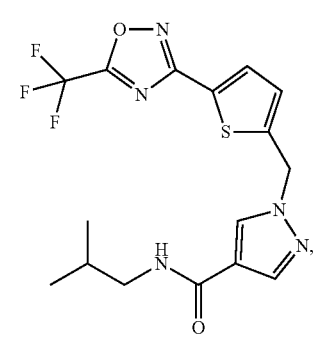

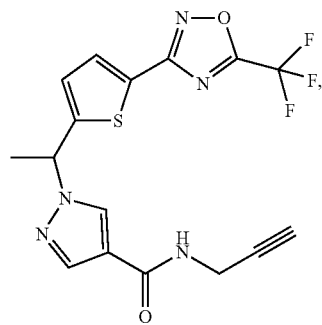

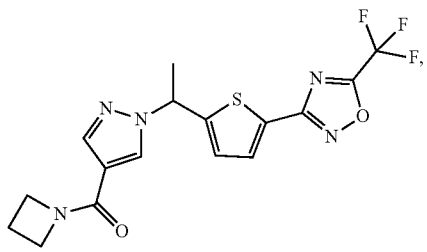

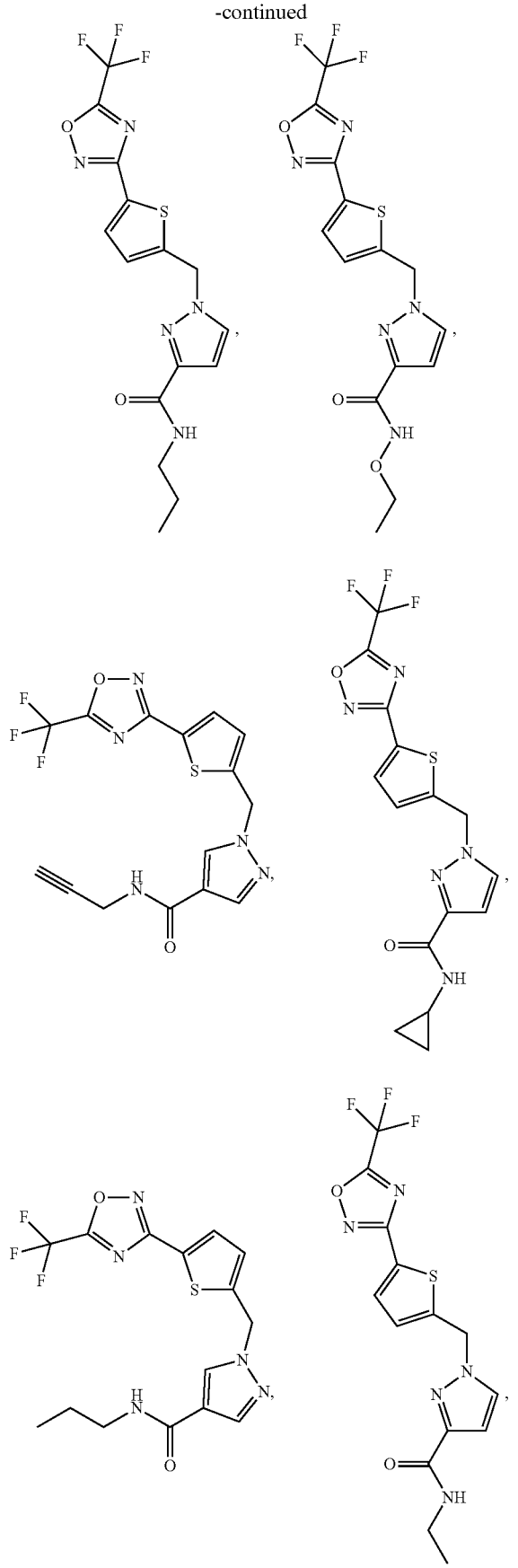
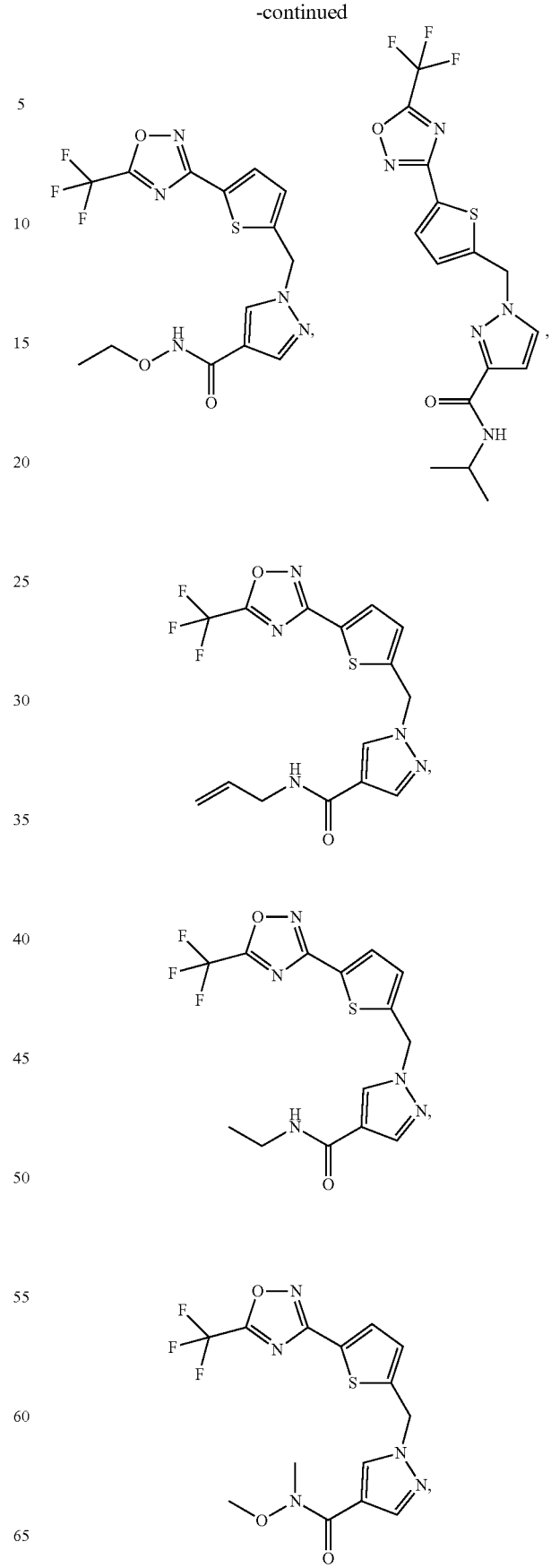

-continued
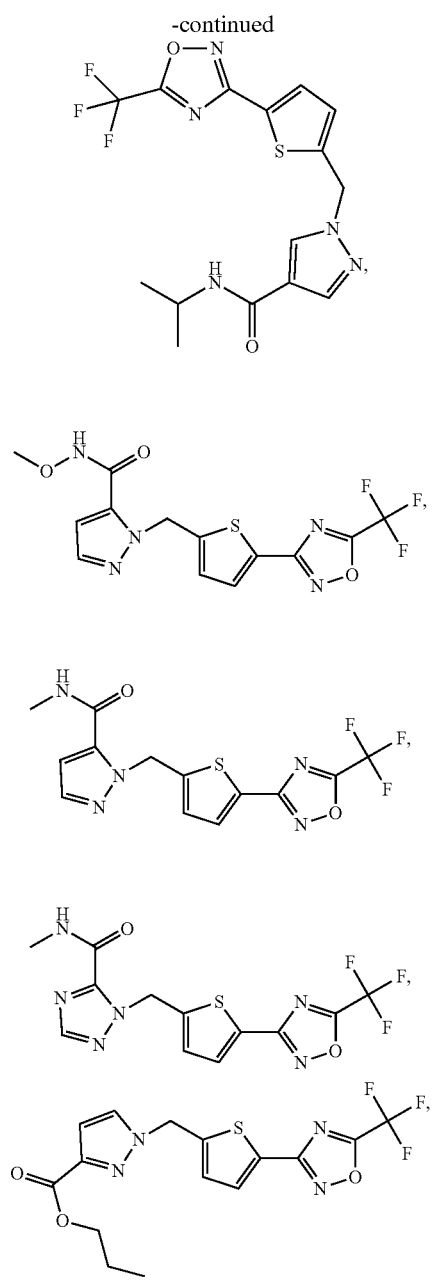
-continued
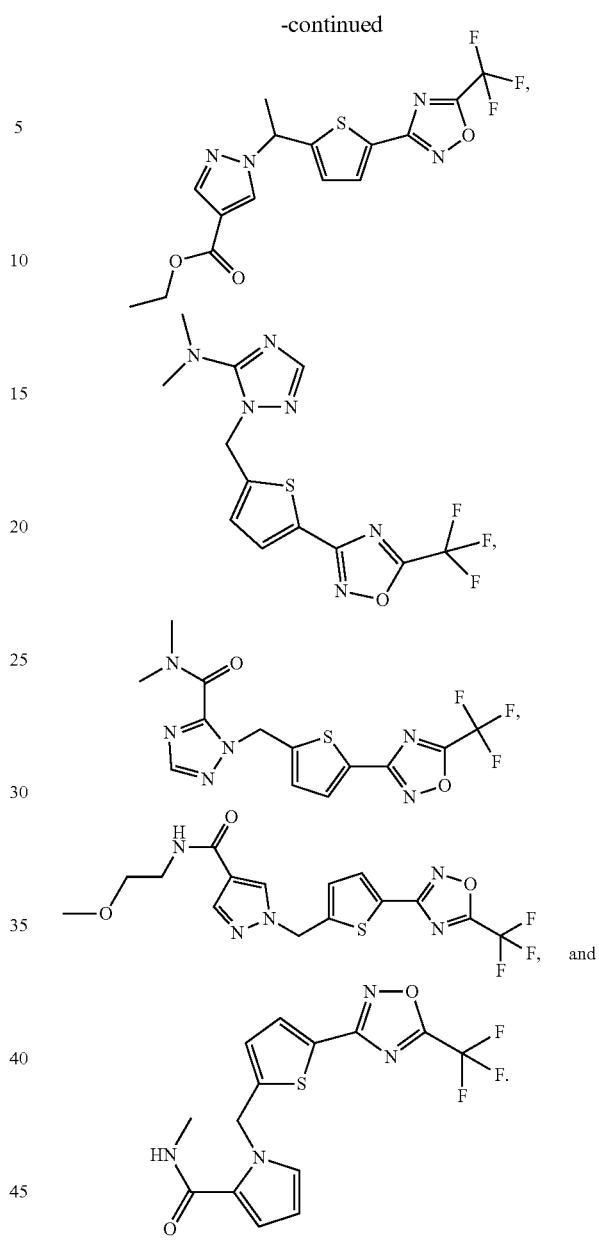
and
* * * * *